(12) United States Patent
Durrant et al.

(10) Patent No.: US 10,835,618 B2
(45) Date of Patent: Nov. 17, 2020

(54) SIALYL-DI-LEWIS$^a$ AS EXPRESSED ON GLYCOPROTEINS BUT NOT GLYCOLIPIDS AS A FUNCTIONAL CANCER TARGET AND ANTIBODIES THERETO

(71) Applicant: The University of Nottingham, Nottingham (GB)

(72) Inventors: Lindy Gillian Durrant, Nottingham (GB); Mireille Vankemmelbeke, Nottingham (GB); Silvana Tivadar, Nottingham (GB); Tina Parsons, Nottingham (GB); Richard McIntosh, Nottingham (GB)

(*) Notice: Subject to any disclaimer, the term of this patent is extended or adjusted under 35 U.S.C. 154(b) by 105 days.

(21) Appl. No.: 15/754,882

(22) PCT Filed: Aug. 25, 2016

(86) PCT No.: PCT/GB2016/052647
§ 371 (c)(1),
(2) Date: Feb. 23, 2018

(87) PCT Pub. No.: WO2017/033020
PCT Pub. Date: Mar. 2, 2017

(65) Prior Publication Data
US 2018/0236095 A1 Aug. 23, 2018

(30) Foreign Application Priority Data
Aug. 25, 2015 (GB) .................................. 1515094.9

(51) Int. Cl.
| | | |
|---|---|---|
| C07K 16/30 | (2006.01) | |
| A61K 47/68 | (2017.01) | |
| C07K 16/28 | (2006.01) | |
| A61P 35/00 | (2006.01) | |
| A61K 39/00 | (2006.01) | |

(52) U.S. Cl.
CPC ...... *A61K 47/6849* (2017.08); *A61K 47/6803* (2017.08); *A61K 47/6857* (2017.08); *A61K 47/6859* (2017.08); *A61K 47/6863* (2017.08); *A61K 47/6869* (2017.08); *A61P 35/00* (2018.01); *C07K 16/2896* (2013.01); *C07K 16/30* (2013.01); *C07K 16/303* (2013.01); *C07K 16/3023* (2013.01); *C07K 16/3046* (2013.01); *C07K 16/3069* (2013.01); *A61K 2039/505* (2013.01); *C07K 2317/24* (2013.01); *C07K 2317/30* (2013.01); *C07K 2317/622* (2013.01); *C07K 2317/732* (2013.01); *C07K 2317/734* (2013.01); *C07K 2317/77* (2013.01); *C07K 2317/92* (2013.01)

(58) Field of Classification Search
CPC .......................... A61K 47/6849; C07K 16/30
USPC ........................................ 424/133.1, 178.1
See application file for complete search history.

(56) References Cited

U.S. PATENT DOCUMENTS

| | | | | |
|---|---|---|---|---|
| 7,527,789 B2* | 5/2009 | Loibner | ............... | A61K 39/395 424/143.1 |
| 2009/0181030 A1* | 7/2009 | Loibner | ............... | A61K 39/395 424/139.1 |
| 2016/0264652 A1 | 9/2016 | Durrant et al. | | |

FOREIGN PATENT DOCUMENTS

WO  WO 2015/053871 A2  4/2015

OTHER PUBLICATIONS

George et al. (Circulation. 1998; 97: 900-906).*
Millipore/Sigma product sheet for FH7 antibody (pp. 1-3 (Nov. 19, 2019)).*
Nudelman et al., (J Biol Chem. 261(12):5487-95 (Apr. 25, 1986)).*
Bergquist et al., "Carbohydrate Antigen 19-9 Elevation in Anatomically Resectable, Early Stage Pancreatic Cancer Is Independently Associated with Decreased Overall Survival and an Indication for Neoadjuvant Therapy: A National Cancer Database Study," *Journal of the American College of Surgeons*, vol. 223, No. 1, pp. 52-65, 2016.
Heimburg-Molinaro et al., "Cancer vaccines and carbohydrate epitopes," *Vaccine*, vol. 29, No. 48, pp. 8802-8826, 2011 (57 pages, Author Manuscript version).
Miyazaki, "Loss of Disialyl Lewis$^a$, the Ligand for Lymphocyte Inhibitory Receptor Sialic Acid-Binding Immunoglobulin-Like Lectin-7 (Siglec-7) Associated with Increased Sialyl Lewis$^a$ Expression on Human Colon Cancers," *Cancer Research*, vol. 64, No. 13, pp. 4498-4505, 2004.
Noble, "Characterisation of anti-glucan monoclonal antibodies," Ph.D. Thesis, University of Nottingham, retrieved from http://eprints.nottingham.ac.uk/12071/1/Final_Thesis_for_Submission_16.6.11.pdf, on Nov. 15, 2016, 262 pages, 2011.
Tsuchida et al., "Synthesis of Disialyl Lewis a (Le$^a$ ) Structure in Colon Cancer Cell Lines by a Sialyltransferase, ST6GalNAc VI, Responsible for the Synthesis of α-Series Gangliosides," *Journal of Biological Chemistry*, vol. 278, No. 25, pp. 22787-22794, 2003.

* cited by examiner

*Primary Examiner* — Lynn A Bristol
(74) *Attorney, Agent, or Firm* — Klarquist Sparkman, LLP

(57) ABSTRACT

The present invention relates to an isolated specific binding member capable of binding sialyl-di-Lewis$^a$, and associated treatments and pharmaceutical compositions for treatment of cancer.

17 Claims, 34 Drawing Sheets
Specification includes a Sequence Listing.

Figure 1a

```
FG129_29H                                                                    -19 ·M· ·L· ·L· ·G·
                                                                                 atg ctg ttg ggg LEADER
              ·L· ·K· ·W· ·V· ·F· ·F· ·V· ·F· ·Y· ·Q· ·G· ·V· ·H· ·C·
FG129_29H     ctg aag tgg gtt ttc ttt gtt ttt tat caa ggt gtg cat tgt <------------------- FR1 - IMGT ------------------->
               E   V   Q   L   V   E   S   G   G       G   L   V   Q   P
FG129_29H   1  gag gtg cag ctt gtt gag tct gga ... gga ttg gtg cag cct -------------------                   <--- CDR1 - IMGT ---
               K   G   S   L   K   L   S   C   A   A   S   G   F   T   F
FG129_29H  16  aaa ggg tca ttg aaa ctc tca tgt gca gcc tct gga ttc acc ttc ---                  <------- FR2 - IMGT -------
                                     N   T   Y   A   M   N   W   V   R   Q   A
FG129_29H  31  ___ ___ ___ ___ ___ aat acc tac gcc atg aac tgg gtc cgc cag gct ----------- FR2 - IMGT -------->   <--- CDR2 - IMGT ---
               P   G   K   G   L   E   W   V   A   R   I   R   S   K   S
FG129_29H  46  cca gga aag ggt ttg gaa tgg gtt gct cgc ata aga agt aaa agt ---   <--------- CDR2 - IMGT --------->   <--- FR3 - IMGT ---
               N   N   Y   A   T   Y   Y   A   D   S   V   K       D   R
FG129_29H  61  aat aat tat gca aca tat tat gcc gat tca gtg aaa ... gac agg

-------------------- FR3 - IMGT -----------------
```

Figure 1a continued

| | | | | | | | | | | | | | | |
|---|---|---|---|---|---|---|---|---|---|---|---|---|---|---|
FG129_29H 76 | F | T | I | S | R | D | D | S | Q | S | M | L | Y | L | Q
| | ttc | acc | ata | tcc | aga | gat | gat | tca | caa | agc | atg | ctc | tat | ctg | caa
| | | | | | ----- | FR3 - IMGT | | | | | | | | -----> |
FG129_29H 91 | M | N | N | L | K | K | E | D | T | A | M | Y | Y | C | V
| | atg | aac | aac | ttg | aaa | aag | gag | gac | aca | gcc | atg | tac | tac | tgt | gta
| | ----- | CDR3 - IMGT | | | | | | | | | | | | |
FG129_29H 106 | G | Y | G | S | G | G | N | Y | W | G | Q | G | . | . | .
| | ggg | tac | ggt | agt | ggg | gga | aac | tac | tgg | ggt | caa | gga | . | . | .
FG129_29H 121 | T | S | V | .T. | .V. | .S. | .S. | A | K | T | T | P | P | S | V
| | acc | tca | gtc | .T. | .V. | .S. | tca | gcc | aaa | acg | aca | cca | ccc | tct | gtc
FG129_29H 136 | Y | P | L | A | P | C | S | A | Q | T | N | S | M | V | T
| | tat | cca | ctg | gcc | cct | tgc | tca | gct | caa | act | aac | tcc | atg | gtg | aca
FG129_29H 151 | L | G | C | L | V | K | G | Y | F | P | E | P | V | T | V
| | ctg | gga | tgc | ctg | gtc | aag | ggc | tat | ttc | cct | gag | cct | gtg | act | gtg
FG129_29H 166 | T | W | N | S | G | S | L | S | S | S | V | H | T | F | P
| | acc | tgg | aac | tct | gga | tcc | ctg | tcc | agc | agt | gtg | cac | acc | ttc | cca
FG129_29H 181 | A | V | L | Q | S | D | L | Y | T | L | S | S | S | V | T
| | gct | gtc | ctg | cag | tct | gac | ctc | tac | act | ctg | agc | agc | tca | gtg | act
FG129_29H 196 | V | P | S | S | T | W | P | S | Q | T | V | T | C | N | V
| | gta | ccc | tcc | agc | acc | tgg | ccc | agc | cag | acc | gtc | acc | tgc | aac | gtt
FG129_29H 211 | A | H | P | A | S | S | T | K | V | D | K | K | I | V | P
| | gcc | cac | ccg | gcc | agc | agc | acc | aag | gtg | gac | aag | aaa | att | gtt | cca
FG129_29H 226 | R | D | C | G | C | K | P | C | I | C | T | V | P | E | V

Figure 1a continued

```
FG129_29H  241  ccc agg gat tgt ggt tgt aag cct tgc aca gtc cca gaa
                 P   R   D   C   G   C   K   P   C   T   V   P   E
FG129_29H  256  gta tca tct gtc ttc atc ttc ccc ccc ata tgt aca gtc
                 V   S   S   V   F   I   F   P   P   K   P   K   D   V
FG129_29H  271  acc att act ctg act cct aag gtc acg tgt gtt gtg gtg gat gtg
                 T   I   T   L   T   P   K   V   T   C   V   V   V   D   V
FG129_29H  286  agc aag gat gat ccc gag gtc cag ttc agc tgg ttt gta gat gat
                 S   K   D   D   P   E   V   Q   F   S   W   F   V   D   D
FG129_29H  301  gtg gag gtg cac aca gct caa aca cag acg cag cca cgg gag gag
                 V   E   V   H   T   A   Q   T   Q   T   H   R   E   E
FG129_29H  316  aac agt act ttc cgc tca gtc agt ctt ctc acc gtc cgg gag cag
                 N   S   T   F   R   S   V   S   L   L   T   V   R   H   Q
FG129_29H  331  gac tgg ctc aat ggc aag gag tac aag tgc aag gtc tcc aac aag
                 D   W   L   N   G   K   E   Y   K   C   K   V   S   N   K
FG129_29H  346  gct ctc cct gcc ccc atc gag aaa acc atc tcc aaa acc aaa
                 A   L   P   A   P   I   E   K   T   I   S   K   T   K
FG129_29H  361  aga cca aag gct cag gtc cga tgt gtc aaa acc ccc cct ccc gag
                 R   P   K   A   Q   V   R   C   V   K   T   P   P   E
FG129_29H  376  cag atg gcc aag gat cag gtc agc ctg acc tgc atg ata aca gac
                 Q   M   A   K   D   Q   V   S   L   T   C   M   I   T   D
FG129_29H  391  ttc ttc cct gaa gac att act gtg gag tgg cag tgg aat ggg cag
                 F   F   P   E   D   I   T   V   E   W   Q   W   N   G   Q
                 P   A   E   N   Y   K   N   T   P   I   M   N   T   N
```

Figure 1a continued

```
FG129_29H      cca gcg gag aac aag tac aag aac act cag ccc atc atg aac acg aat
                                                                              N
                G   S   E   N   K   Y   V   S   K   L   N   V   Q   K   S
FG129_29H  406  ggc tct tac ttc gtc agc tac agc aag ctc aat gtg cag aag agc aac W   E   A   G   N   T   F   C   S   V   L   H   E   G
FG129_29H  421  tgg gag gca gga aat act act ttc tgc tct gtg tta cat gag ggc L   H   N   H   H   T   E   K   S   L   S   H   P   G
FG129_29H  436  ctg cac aac cat cac act gag aag agc ctc tcc cac cct ggt K
FG129_29H  451  aaa
```

Figure 1b

```
                                LEADER                    |
                -20  M   E   S   Q   V   L   M   S   L   L   E   W   V   S   G   T
FG129_29K            atg gaa tca cag gtc ctc atg tcc ctg ctg tgg gta tct ggt acc

|<------ FR1 - IMGT ------
                -15  Q   V   Q   L   V   Q   S   G   T                            
FG129_29K            cag gtc cag ctg gta cag tct gga

|<----- CDR1 - IMGT
                  1  A   E   V   K   K   P   G   E   S   L   K   I   S   C        
FG129_29K            gca gag gtg aag aag cct ggg gag tcc ctg aag atc tcc ----->|<------- FR2 - IMGT ------->|<-- CDR2 - IMGT
                 16  K   G   S   G   Y   S   F   T   S   Y   W   I   G            
FG129_29K            aag gga tcc gga tac agt ttc acc agc tac tgg atc gga ------>|<-------- FR3 - IMGT
                 31  W   V   R   Q   M   P   G   K   G   L   E   W   M   G        
FG129_29K            tgg gtg cgc cag atg ccc ggg aaa ggc ctg gag tgg atg gga      
```

(sequence alignment figure; text partially reconstructed)

Figure 1b continued

```
                  <-----------------------  FR3 - IMGT  ---------------------->
             I   S   S   V   Q   A   E   D   L   A   V   Y   Y   C   Q
FG129_29K  91 atc agc agt gtg cag gct gaa gac ctg gca gtt tat tac tgt cag
                         CDR3 - IMGT
              N   D   Y   S   S   P   F   T   F   G   S   G   T   K   L
FG129_29K 106 aat gat tat agt tct cca ttc acg ttc ggc tcg ggg aca aag ttg
              E   I   K   R   A   D   A   A   P   T   V   S   I   F   P
FG129_29K 121 gaa ata aaa cgg gct gat gca gca cca act gta tcc atc ttc cca
              P   S   S   E   Q   L   T   S   G   G   A   S   V   V   C
FG129_29K 136 cca tcc agt gag cag tta aca tct gga ggt gcc tca gtc gtg tgc
              F   L   N   N   F   Y   P   K   D   I   N   V   K   W   K
FG129_29K 151 ttc ttg aac aac ttc tac ccc aaa gac atc aat gtc aag tgg aag
              I   D   G   S   E   R   Q   N   G   V   L   N   S   W   T
FG129_29K 166 att gat ggc agt gaa cga caa aat ggc gtc ctg aac agt tgg act
              D   Q   D   S   K   D   S   T   Y   S   M   S   S   T   L
FG129_29K 181 gat cag gac agc aaa gac agc acc tac agc atg agc agc acc ctc
              T   L   T   K   D   E   Y   E   R   H   N   S   Y   T   C
FG129_29K 196 acg ttg acc aag gac gag tat gaa cga cat aac agc tat acc tgt
              E   A   T   H   K   T   S   T   S   P   I   V   K   S   F
FG129_29K 211 gag gcc act cac aag aca tca act tca ccc att gtc aag agc ttc
              N   R   N   E   C
FG129_29K 226 aac agg aat gag tgt
```

Figure 2a

```
Ch129_29H           -19  ·M·  ·L·  ·L·  ·G·
                         atg  ctg  ttg  ggg
                         ─────── LEADER ───────
Ch129_29H        ·L·  ·K·  ·W·  ·V·  ·F·  ·F·  ·Y·  ·Q·  ·G·  ·V·  ·H·  ·C·
                 ctg  aag  tgg  gtt  ttc  ttt  gtt  ttt  tat  caa  ggt  gtg  cat  tgt
                 <─────────────────────── FR1 - IMGT ───────────────────────
Ch129_29H     1   E    V    Q    L    V    E    S    G    G         G    L    V    Q    P
                 gag  gtg  cag  ctt  gtt  gag  tct  gga  gga  ...  gga  ttg  gtg  cag  cct
                 ──────── FR1 - IMGT ────────────────>  <─────── CDR1 - IMGT
Ch129_29H    16   K    G    S    L    K    L    S    C    A    A    S    G    F    T    F
                 aaa  ggg  tca  ttg  aaa  ctc  tca  tgt  gca  gcc  tct  gga  ttc  acc  ttc
                 ─── CDR1 - IMGT ───>                 <────────── FR2 - IMGT ──────────
Ch129_29H    31   ·    ·    ·    N    T    Y    A    M    N    W    V    R    Q    A
                           ...  aat  acc  tac  gcc  atg  aac  tgg  gtc  cgc  cag  gct
                                                     ────── FR2 - IMGT ──────────────>
Ch129_29H    46   P    G    K    G    L    E    W    V    A    R    I    R    S    K    S
                 cca  gga  aag  ggt  ttg  gaa  tgg  gtt  gct  cgc  ata  aga  agt  aaa  agt
                                                                  <──────── CDR2 - IMGT
Ch129_29H    61   N    Y    A    T    Y    Y    A    D    S    V    K         D    R
                 aat  tat  gca  aca  tat  tat  gcc  gat  tca  gtg  aaa  ...  gac  agg
                 ─ CDR2 - IMGT ──>                 <──────── FR3 - IMGT
                                                             FR3 - IMGT
```

```
Ch129_29H        tgg gag agc aat ggg cag ccg gag aac tac aag acc acg cct
                  W   E   S   N   G   Q   P   E   N   Y   K   T   T   P
Ch129_29H   406   P   V   L   D   S   G   D   S   F   F   L   Y   S   K   L
                  ccc gtg ctg gac tcc ggc gac tcc ttc ttc ctc tac agc aag ctc
Ch129_29H   421   T   V   D   K   S   R   W   Q   Q   G   N   V   F   S   C
                  acc gtg gac aag agc agg tgg cag cag ggg aac gtc ttc tca tgc
Ch129_29H   436   S   V   M   H   E   A   L   H   N   H   Y   T   Q   K   S
                  tcc gtg atg cat gag gct ctg cac aac cac tac acg cag aag agc
Ch129_29H   451   L   S   L   S   P   G   K
                  ctc tcc ctg tct ccg ggt aaa
```

```
                    LEADER
          -20  M   E   S   Q   T
               atg gaa tca cag act
          -15  Q   V   L   M   S   L   L   F   W   V   S   G   T   C   G
Ch129_29K      cag gtc ctc atg tcc ctg ctg ttc tgg gta tct ggt acc tgt ggg
               <------------------ FR1 - IMGT ----------------------->
            1  D   I   V   M   T   Q   S   P   S   S   L   T   V   T   A
Ch129_29K      gac att gtg atg aca cag tct cca tcc tcc ctg act gtg aca gca
                                              <----- CDR1 - IMGT -----
           16  G   E   K   V   T   M   S   C   K   S   S   Q   S   L   L
Ch129_29K      gga gag aag gtc act atg agc tgc aag tcc agt cag agt ctg tta
               -------->  <--------- FR2 - IMGT -----------> 
           31  N   S   G   N   Q   K   N   Y   L   T   W   Y   Q   Q   K
Ch129_29K      aac agt gga aat caa aag aac tac ttg acc tgg tac cag cag aaa
                                              <----- CDR2 - IMGT
           46  P   G   Q   P   P   K   V   L   I   Y   W   A   . . .
Ch129_29K      cca ggg cag cct cct aaa gtg ttg atc tac tgg gca . . .
               --->   <-------------- FR3 - IMGT
           61                S   T   R   E   S   G   V   P   D   R
Ch129_29K      . . .         tcc act agg gaa tct ggg gtc cct . . . gat cgc
               ------------------------- FR3 - IMGT ----------------------
```

Figure 2b continued

```
              F   T   G   S   G       S   G   T   D   F   T   L   T
Ch129_29K  76 ttc aca ggc agt gga ... tct gga aca gat ttc act ctc acc
                                              FR3 - IMGT -------->
              I   S   S   V   Q       A   E   D   L   A   Y   Y   C   Q
Ch129_29K  91 atc agc agt gtg cag gct gaa gac ctg gca gtt tat tgt cag
                              CDR3 - IMGT
              N   D   Y   S   S   P   F   T   F   G   S   G   T   K   L
Ch129_29K 106 aat gat tat agt tct cca acg ttc ggg tca aag ttg
              E   I   K   R   T   V   A   A   P   S   V   F   I   F   P
Ch129_29K 121 gaa ata aaa cgt acg gta gcg gcc cca tct gtc ttc atc ttc ccg
              P   S   D   E   Q   L   K   S   G   T   A   S   V   V   C
Ch129_29K 136 cca tct gat gag cag ttg aaa tct gga act gcc tct gtt gtg tgc
              L   L   N   N   F   Y   P   R   E   A   K   V   Q   W   K
Ch129_29K 151 ctg ctg aat aac ttc tat ccc aga gag gcc aaa gta cag tgg aag
              V   D   N   A   L   Q   S   G   N   S   Q   E   S   V   T
Ch129_29K 166 gtg gat aac gcc ctc caa tcg ggt aac tcc cag gag agt gtc aca
              E   Q   D   S   K   D   S   T   Y   S   L   S   S   T   L
Ch129_29K 181 gag cag gac agc aag gac agc acc tac agc ctc agc agc acc ctg
              T   L   S   K   A   D   Y   E   K   H   K   V   Y   A   C
Ch129_29K 196 acg ctg agc aaa gca gac tac gag aaa cac aaa gtc tac gcc tgc
              E   V   T   H   Q   G   L   S   S   P   V   T   K   S   F
Ch129_29K 211 gaa gtc acc cat cag ggc ctg agc tcg ccc gtc aca aag agc ttc
              N   R   G   E   C
Ch129_29K 226 aac aga ggg gag tgt
```

Figure 13a

```
FG129-scFv    <--------------------- Leader --------------------->
              atgctgtgggctgaagtggtttcttgttttatcaagtgtgcatctatcg
              MetLeuLeuGlyLeuLysTrpValPhePheValValLeuSerValHisLeuSer FG129-scFv    <--------------- heavy chain variable region --------->
              atggaggtgcagcttgttgagtctgtagaggattgtgcagcctaaaggtcattgaaa
              MetGluValGlnLeuValGluSerGlyGlyLeuValGlnProLysGlySerLeuLys FG129-scFv    <--------------- heavy chain variable region --------->
              ctctcatgtgcagcctctggattcaccttcaatacctacgccatgaactgggtccgccag
              LeuSerCysAlaAlaSerGlyPheThrPheAsnThrTyrAlaMetAsnTrpValArgGln FG129-scFv    <--------------- heavy chain variable region --------->
              gctccaggaaaggttttggaatggttgctccgcataagaagtaaagtaataattatgca
              AlaProGlyLysGlyLeuGluTrpValAlaArgIleSerLysSerAsnAsnTyrAla FG129-scFv    <--------------- heavy chain variable region --------->
              acatattatgccgattcagtgaaagacaggttcaccatatccagagatgattcacaaagc
              ThrTyrTyrAlaAspSerValLysAspArgPheThrIleSerArgAspAspSerGlnSer FG129-scFv    <--------------- heavy chain variable region --------->
              atgctctatctgcaaatgaacaacttgaaaaggaggacacagccatgtattactgtgta
              MetLeuTyrLeuGlnMetAsnAsnLeuLysGluAspThrAlaMetTyrTyrCysVal FG129-scFv    <------------------------><--------- 3 x GGGGS linker --------->
              gggtacggtagtggggaaaactactgggtcaaggaacctcagtcaccgtctcctcaagt
              GlyTyrGlySerGlyGlyAsnTyrTrpValThrSerValThrValSerSerGly FG129-scFv    <--------- 3 x GGGGS linker ---------><----
              ggaggcggttcaggcggaggtggctctggcggtggcggatcagacattgtgatgacacag
              GlyGlyGlySerGlyGlyGlyGlySerGlyGlyGlyGlySerAspIleValMetThrGln FG129-scFv    <--------------- light chain variable region --------->
              tctccatctctccctgactgtgtcagcagaggaaggtcactatgagctgcaagtccagt
              SerProSerLeuThrValSerAlaGlyGluLysValThrMetSerCysLysSerSer
```

Figure 13a continued

```
              <------------ light chain variable region ------------>
FG129-scFv   caagagtctgttaaacagtcagaaatcaaaagaactactgacctgtaccagcagaaacca
             GlnSerLeuLeuAsnSerGlyAsnGlnLysGlnLysAsnTyrLeuThrTrpTyrGlnGlnLysPro <------------ light chain variable region ------------>
FG129-scFv   gggcagcctcctaaagtgttgatctactgtggcatcctggatggaatctgggtgtccctgat
             GlyGlnProProLysValLeuIleTyrTrpAlaSerThrArgGluSerGlyValProAsp <------------ light chain variable region ------------>
FG129-scFv   cgcttcacaggcagtggatctgggaacagattccactctcaccatcagcagtgtgcagct
             ArgPheThrGlySerGlySerGlyAsnArgPheThrLeuThrIleSerSerValGlnAla <------------ light chain variable region ------------>
FG129-scFv   gaagacctggcagtttattactgtcagaatgattatagttctccattcacgttcggctcg
             GluAspLeuAlaValTyrTyrCysGlnAsnAspTyrSerSerProPheThrPheGlySer ><------ poly-Ala and 6 x His tag ------>
FG129-scFv   gggacaaagttggaaataaaacgggcggccgctgcagcggcatcaccatcaccatcactaa
             GlyThrLysLeuGluIleLysArgAlaAlaAlaAlaAlaHisHisHisHisHisHisOc*
```

SIALYL-DI-LEWIS$^a$ AS EXPRESSED ON GLYCOPROTEINS BUT NOT GLYCOLIPIDS AS A FUNCTIONAL CANCER TARGET AND ANTIBODIES THERETO

CROSS REFERENCE TO RELATED APPLICATIONS

This is the § 371 U.S. National Stage of International Application No. PCT/GB2016/052647, filed Aug. 25, 2016, which was published in English under PCT Article 21(2), which in turn claims the benefit of GB Application No. 1515094.9, filed Aug. 25, 2015, which is incorporated by reference herein in its entirety.

The present invention relates to targeting of sialyl-di-Lewis$^a$ in cancer and binding members, such as monoclonal antibodies (mAbs), which bind this glycan as expressed on glycoproteins but not lipids.

Glycan structures are present on both protein and glycolipid backbones and can be massively over-expressed in cancer due to altered expression of glycosyltransferases. During N-linked glycosylation, proteins in the ER are decorated with a branched 9 mannose sugar (man)$_9$ complex. When the protein exits the ER, mannosidase I removes 4 of the mannose sugars (man)$_5$ and then mannosidases II removes a further 2 (man)$_3$. Glycosyltransferases then build complex glycan structures on this mannose core. These glycans are vital for folding and the function of the proteins. Generating mAbs to glycans expressed on proteins is a problem, as the mAbs rarely see just the small glycan but usually recognise the glycan on the specific protein giving a very restrictive expression.

During oncogenesis, the glycosylation processes are highly dysregulated leading to altered glycan expression at the surface of cancer cells which results in tumour-associated carbohydrate antigens (TACAs). In tumours, TACAs are not only aberrantly expressed and have a dense distribution compared to normal tissue, but they are also involved in many physiological processes such as protein folding and trafficking, adhesion, and cell proliferation, making them attractive targets for therapeutic mAbs.

Lewis carbohydrates are ideal candidates for mAb therapy as they have a very limited distribution on normal tissues and are over-expressed in cancers that originated from epithelial cells, particularly in pancreatic and gastrointestinal cancer. They are formed by the sequential addition of fucose onto oligosaccharide precursor chains on glycoproteins and glycolipids, through the action of glycosyltransferases and can be divided in type I chains—which form Le$^a$ and Le$^b$ and type II chains—which form Lewis$^x$ and Lewis$^y$.

Sialyl-Lewis$^a$ is a ligand of E-selectin involved in endothelial leukocyte adhesion and is over-expressed in cancers of the hepato-biliary system, pancreas and gastrointestinal tract, while its natural form, di-sialyl-Lewis$^a$ which has an extra sialic acid sugar, is found in non-malignant epithelial cells. Expression of sialyl-Lewis$^a$ was found to increase metastatic potential in pancreatic adenocarcinoma (16, 27) and colon cancer (14, 15). In pancreatic and colon cancer, sialyl-Lewis$^a$ is also used as a tumour marker to monitor responses to therapy (13,17,18). Sialyl-di-Lewis$^a$ (this has the single sialic acid found in cancers but also has the Lewis$^a$ duplicated and is only found on proteins), is expressed by a wide range of pancreatic tumours but has a very restricted normal tissue expression. More recently, human sialyl-Lewis$^a$ mAbs were produced using a patient vaccination strategy that showed specific binding to sialyl-Lewis$^a$ and exhibited ADCC, CDC and anti-tumour activity in a xenograft model (20). One of these mabs, 5B1, is a human IgG1 which predominantly binds Sialyl Lewis$^a$ whether the neuraminic acid is endogenously produced (N-acetyl-neuraminic acid) or exogenously derived (N-glycolyl-neuraminic acid) and whether it is on a long or short spacer. Binding to Sialyl-di-lewis$^a$ or Sialyl lewis$^{a-x}$ is weak and insignificant. The second mab 7E3 is a human IgM which binds equally to Sialyl lewis$^a$ whether the neuraminic acid is endogenously produced (N acetyl neuraminic acid) or exogenously derived (N-glycolyl-neuraminic acid) and whether it is on a long or short spacer, and to Sialyl-di-lewis$^a$ or Sialyl lewis$^{a-x}$. Such anti-Sialyl Lewis$^a$ mabs would have an unacceptable normal distribution, which is supported by the observation that GivaRex (a mouse monoclonal antibody) and its patent (WO0191792) has been abandoned in preclinical studies.

An aim of the present invention is to provide an improved binding member for sialyl-di-Lewis$^a$.

According to a first aspect of the invention, there is provided an isolated specific binding member capable of binding sialyl-di-Lewis$^a$.

The binding member may be specific for sialyl-di-Lewis$^a$. In one embodiment, the binding member may be specific for sialyl-di-Lewis$^a$ and sialyl-Lewis$^{a-x}$. The binding member may be specific for sialyl-di-Lewis$^a$. In one embodiment, the binding member may be specific for sialyl-di-Lewis$^a$ and sialyl-Lewis$^{a-x}$ present in tumour tissue. The binding member may not bind, or may not significantly bind, mono-sialyl-Lewis$^a$ bound to a glycolipid. Additionally or alternatively, the binding member may not bind, or may not significantly bind, di-sialyl-Lewis$^a$. The binding member may not bind, or may not significantly bind, di-sialyl-Lewis$^a$ present in healthy (non-tumour) tissue.

Synthetic (i.e. non-natural) molecules may be provided for characterizing the binding member binding specificity. Such forms may comprise any one of sialyl-di-Lewis$^a$, sialyl-Lewis$^{a-x}$, di-sialyl-Lewis$^a$ or mono-sialyl-Lewis$^a$ molecules presented on a protein or lipid (e.g. a glycoprotein or glycolipid). The synthetic molecule may comprise sialyl-Lewis$^a$ with exogenously derived N-glycolyl-neuraminic acid or endogenously derived N-acetyl-neuraminic acid. In one embodiment, the binding member may bind mono-sialyl-Lewis$^a$, wherein the mono-sialyl-Lewis$^a$ is presented on a glycoprotein. The binding member may be specific for sialyl-di-Lewis$^a$, sialyl-Lewis$^{a-x}$ and mono-sialyl-Lewis$^a$, wherein the mono-sialyl-Lewis$^a$ is presented on a glycoprotein. In an embodiment wherein the binding member binds to mono-sialyl-Lewis$^a$ presented on a glycoprotein, the mono-sialyl-Lewis$^a$ may be linked to the protein by a spacer, such as a polymer. The polymer may comprise any natural or synthetic molecule that allows sialyl-Lewis$^a$ to bind into a groove of the binding member. The polymer chain may comprise a glycan chain or amino acid (i.e. a polypeptide). The glycan chain linking the mono-sialyl-Lewis$^a$ to the glycoprotein may comprise at least 4 glycan monomer units. Alternatively, the glycan chain linking the mono-sialyl-Lewis$^a$ to the glycoprotein may comprise at least 5 glycan monomer units. Alternatively, the glycan chain linking the mono-sialyl-Lewis$^a$ to the glycoprotein may comprise at least 6 glycan monomer units. Alternatively, the glycan chain linking the mono-sialyl-Lewis$^a$ to the glycoprotein may comprise at least 7 glycan monomer units. Alternatively, the glycan chain linking the mono-sialyl-Lewis$^a$ to the glycoprotein may comprise at least 8 glycan monomer units. The polypeptide linking the mono-sialyl-Lewis$^a$ to the glycoprotein may comprise at least 4 amino acids. Alternatively, the polypeptide linking the mono-sialyl-Lewis$^a$ to the glycoprotein may comprise at least 5 amino acids. Alternatively, the polypeptide linking the mono-sialyl-Lewis$^a$ to the glycoprotein may comprise at least 6 amino acids. Alternatively, the polypeptide linking the mono-sialyl-Lewis$^a$ to the glycoprotein may comprise at least 7 amino acids. Alternatively, the polypeptide linking the mono-sialyl-Lewis$^a$ to the glycoprotein may comprise at least 8 amino acids.

The present invention advantageously provides a binding member, such as a monoclonal antibody, that shows a high specificity for sialyl-di-Lewis$^a$ and sialyl-Lewis$^{a-x}$. It can also bind to mono-sialyl-Lewis$^a$ when it is linked to a glycoprotein by a glycan chain, suggesting that it requires at least 4 carbohydrates presented in the correct conformation to bind and a spacer (such as a glycan chain) to allow insertion into the antibody groove. This constraint, in contrast to other mono-sialyl-Lewis$^a$ binding maAbs, gives it the unique ability to bind to glycoproteins but not glycolipids. In contrast to the other mabs, its inability to recognize Sialyl lewis$^a$ alone prevents it from binding to this sugar on glycolipids and gives it a unique and very restrictive normal (i.e. non-cancerous) tissues binding profile. Without being bound by theory, the binding member may not bind to glycolipid bound Sialyl lewis$^a$ as the lipid is too hyrophobic to allow insertion of the glycan into the deep antibody groove.

The invention herein has provided, characterised and chimerised a binding member, such as FG129 mAb. This mAb targets the novel glycan, sialyl-di-Lewis$^a$ (this has the single sialic acid found in cancers but also has the Lewis$^a$ duplicated and is only found on proteins), which is expressed by a wide range of pancreatic tumours but has a very restricted normal tissue expression. Chimeric FG129 (CH129) induces strong ADCC and CDC responses on tumours, suggesting the antigen is a good target for immune mediated killing. This can be further potentiated by redirecting T cell killing by recombination of FG129 with a second mAb recognising and activating T cells. Thus, in addition to the antibody inducing ADCC, a further application of the humanised mAb is in the generation of a bispecific mAb targeting the FG129 and CD3 antigens. The indication for such a bispecific could be but is not restricted to pancreatic cancer. The mAb FG129 also internalised and delivered drugs which efficiently killed tumour cells, demonstrating its ADC potential.

The invention also provides isolated specific binding member capable of binding sialyl-di-Lewis$^a$ and sialyl-Lewis$^{a-x}$ Neu5Aca2-3Galb1-3(Fuca1-4)GlcNAcb1-3Galb1-4(Fuca1-3)GlcNAcb- and mono-sialyl-Lewis$^a$ Neu5Aca2-3Galb1-3(Fuca1-4)GlcNAcb-only attached to a glycoprotein. Such binding members may be for use in a method for treating cancer. The invention also provides for the use of such a binding partner in the manufacture of a medicament for the treatment of cancer. The invention also provides a method of treating cancer, comprising administering a binding partner of the invention to a subject in need of such treatment.

In one aspect, the present invention provides the mAb FG129 which binds to sialyl-di-Lewis$^a$ and sialyl-Lewis$^{a-x}$ and mono-sialyl-Lewis$^a$ only attached to a glycoprotein.

In another aspect, the present invention provides the chimeric hIgG1 129 which binds to sialyl-di-Lewis$^a$ and sialyl-Lewis$^{a-x}$ and mono-sialyl-Lewis$^a$ only attached to a glycoprotein.

In this invention we show a murine IgG1k mAb, FG129, which binds to sialyl-di-Lewis$^a$ and was generated by immunising Balb/c mice with tumour plasma membrane lipid extracts. They bind to the cell surface of a range of tumour cell lines but do not bind to any blood or endothelial cells.

The binding member may be capable of binding to some pancreatic tumours, for example at least 70% or 74% of pancreatic tumours in a population of patients. The binding member may be capable of binding to some gastric tumours, for example at least 45% or 50% of gastric tumours in a population of patients. The binding member may be capable of binding to some colorectal tumours, for example at least 30% or 36% of colorectal tumours in a population of patients. The binding member may be capable of binding to some ovarian tumours, for example at least 25% or 27% of ovarian tumours in a population of patients. The binding member may be capable of binding to some non small cell lung cancers, for example at least 5% or 7% of non small cell lung cancers in a population of patients. The tumour tissue binding of the binding member may be assessed by immunohistochemistry (IHC) on tumour tissue microarrays (TMAs).

In one embodiment, the binding member does not bind, or does not significantly bind to non-cancerous tissue, such as non-cancerous heart, brain, stomach, or kidney tissue. Additionally or alternatively, the binding member has low affinity for, or does not significantly bind to non-cancerous tissue of the gallbladder, ileum, liver, lung, oesophagus, pancreas, skin or thymus.

The binding member may be capable of binding to glycoprotein-presented sialyl-Lewis$^a$ with an affinity (KD) of less than about $10^{-6}$M. The binding member may be capable of binding to glycoprotein-presented sialyl-Lewis$^a$ with an affinity (KD) of less than about $10^{-7}$M. The binding member may be capable of binding to glycoprotein-presented sialyl-Lewis$^a$ with an affinity (KD) of less than about $10^{-8}$M, $10^{-9}$M, $10^{-10}$M, $10^{-11}$M or $10^{-12}$M. The binding member may be capable of binding to glycoprotein-presented sialyl-Lewis$^a$ with an affinity (KD) of less than about $10^{-13}$M. The binding member may be capable of binding to glycoprotein-presented sialyl-Lewis$^a$ with a dissociation rate (Kd) of $10^{-8}$ 1/s or less. The binding member may be capable of binding to glycoprotein-presented sialyl-Lewis$^a$ with an association rate (Ka) of at least about $10^4$ 1/Ms. Binding affinity may be measured by surface plasmon resonance Biacore X.

A further aspect of the invention provides an isolated specific binding member comprising heavy chain binding domains CDR1, CDR2 and CDR3, and light chain binding domains CDR1, CDR2, and CDR3. The invention may provide an isolated specific binding member comprising one or more binding domains selected from the amino acid sequence of residues 26 to 33 (CDRH1) (SEQ ID NO: 1), 50-59 (CDRH2) (SEQ ID NO: 2) and 98 to 106 (CDRH3) (SEQ ID NO: 3) of FIG. 1a or 2a.

The binding domain may comprise an amino acid sequence substantially as set out as 1-117 (VH) (SEQ ID NO: 4) of FIG. 1a or 2a. In one embodiment, the member comprises a binding domain which comprises an amino acid sequence substantially as set out as residues 98 to 106 (CDRH3) (SEQ ID NO: 3) of the amino acid sequence of FIG. 1a or 2a. In this embodiment, the isolated specific binding member may additionally comprise one or both, preferably both, of the binding domains substantially as set out as residues 26 to 33 (CDRH1) (SEQ ID NO: 1) and residues 50-59 (CDRH2) (SEQ ID NO: 2) of the amino acid sequence shown in FIGS. 1a and 2a.

In another aspect, the present invention provides an isolated specific binding member comprising one or more binding domains selected from the amino acid sequence of residues 27 to 38 (CDRL1) (SEQ ID NO: 5), 56-58 (CDRL2) and 95 to 103 (CDRL3) (SEQ ID NO: 6) of FIG. 1b or 2b.

The binding domain may comprise an amino acid sequence substantially as set out as residues 95 to 103 (CDRL3) (SEQ ID NO: 6) of the amino acid sequence of FIGS. 1b and 2b. In this embodiment, the isolated specific binding member may additionally comprise one or both, preferably both, of the binding domains substantially as set out as residues 27 to 38 and (CDRL1) (SEQ ID NO: 5) residues 56 to 58 of (CDRL2) the amino acid sequence shown in FIGS. 1b and 2b.

In one embodiment, the variable heavy and/or light chain may comprise HCDR1-3 and LCDR1-3 of antibody FG129. In another embodiment, the variable heavy and/or light chain may comprise HCDR1-3 and LCDR1-3 of antibody FG129, and framework regions of FG129.

Specific binding members which comprise a plurality of binding domains of the same or different sequence, or combinations thereof, are included within the present invention. Each binding domain may be carried by a human antibody framework. For example, one or more framework regions may be substituted for the framework regions of a whole human antibody or of the variable region thereof.

One isolated specific binding member of the invention comprises the sequence substantially as set out as residues 1 to 114 (VL) (SEQ ID NO: 7) of the amino acid sequence shown in FIG. 1b or 2b.

In some embodiments binding members having sequences of the CDRs of FIG. 1a or FIG. 2a may be combined with binding members having sequences of the CDRs of FIG. 1b or 2b.

In one embodiment, the binding member may comprise a light chain variable sequence comprising LCDR1, LCDR2 and LCDR3, wherein
    LCDR1 comprises QSLLNSGNQKNY (SEQ ID NO: 5),
    LCDR2 comprises WAS, and
    LCDR3 comprises QNDYSSPFT (SEQ ID NO: 6); and a heavy chain variable sequence comprising HCDR1, HCDR2 and HCDR3, wherein
    HCDR1 comprises GFTFNTYA (SEQ ID NO: 1)
    HCDR2 comprises IRSKSNNYAT (SEQ ID NO: 2), and
    HCDR3 comprises VGYGSGGNY (SEQ ID NO: 3).

In a further aspect, the invention provides a binding member comprising a VH domain comprising residues 1 to 117 (SEQ ID NO: 4) of the amino acid sequence of FIG. 1a or 2a, and a VL domain comprising residues 1 to 114 (SEQ ID NO: 7) of the amino acid sequence of FIG. 1b or 2b.

The invention also encompasses binding partners as described above, but in which the sequence of the binding domains are substantially as set out in FIG. 1 or 2. Thus, binding partners as described above are provided, but in which in one or more binding domains differ from those depicted in FIG. 1 or 2 by from 1 to 5, from 1 to 4, from 1 to 3, 2 or 1 substitution.

The invention also encompasses binding partners having the capability of binding to the same epitopes as the VH (SEQ ID NO: 4) and VL (SEQ ID NO: 7) sequences depicted in FIGS. 1 and 2. The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 50% but preferably 75%, 90% or even 99% as measured in a competitive binding assay compared to a control lacking the competing antibody (see, e.g., Junghans et al., Cancer Res. 50:1495, 1990, which is incorporated herein by reference).

The invention therefore further provides a binding member which competes for binding to sialyl-di-Lewis$^a$ and sialyl-Lewis$^{a\text{-}x}$ and mono-sialyl-Lewis$^a$ only attached to a glycoprotein with an antibody comprising a VH chain having the amino acid sequence of residues 1 to 117 (SEQ ID NO: 4) of FIG. 1a or 2a and a VL chain having the amino acid sequence of residues 1 to 114 (SEQ ID NO: 7) of FIG. 1b or 2b.

In a preferred embodiment the competing binding partner competes for binding to sialyl-di-Lewis$^a$ only attached to a glycoprotein with an antibody comprising a VH chain having the amino acid sequence of residues 1 to 117 (SEQ ID NO: 4) of FIG. 1a or 2a and a VL chain having the amino acid sequence of residues 1 to 114 (SEQ ID NO: 7) of FIG. 1b or 2b.

In a further embodiment the competing binding partner competes for binding to sialyl-di-Lewis$^a$ and sialyl-Lewis$^{a\text{-}x}$ and mono-sialyl-Lewis$^a$ only attached to a glycoprotein with an antibody comprising a VH chain having the amino acid sequence of residues 1 to 117 (SEQ ID NO: 4) of FIG. 1a and a VL chain having the amino acid sequence of residues 1 to 114 (SEQ ID NO: 7) of FIG. 1b, or with an antibody comprising a VH chain having the amino acid sequence of residues 1 to 117 (SEQ ID NO: 4) of FIG. 2a and a VL chain having the amino acid sequence of residues 1 to 114 (SEQ ID NO: 7) of FIG. 2b.

Preferably, competing binding partners are antibodies, for example monoclonal antibodies, or any of the antibody variants or fragments mentioned throughout this document.

Once a single, archtypal mAb, for example an FG129 mAb, has been isolated that has the desired properties described herein, it is straightforward to generate other mAbs with similar properties, by using art-known methods. For example, the method of Jespers et al., Biotechnology 12:899, 1994, which is incorporated herein by reference, may be used to guide the selection of mAbs having the same epitope and therefore similar properties to the archtypal mAb. Using phage display, first the heavy chain of the archtypal antibody is paired with a repertoire of (preferably human) light chains to select a glycan-binding mAb, and then the new light chain is paired with a repertoire of (preferably human) heavy chains to select a (preferably human) glycan-binding mAb having the same epitope as the archtypal mAb.

MAbs that are capable of binding sialyl-di-Lewis$^a$ and sialyl-Lewis$^{a\text{-}x}$ and mono-sialyl-Lewis$^a$ only attached to a glycoprotein and induce ADCC or internalize and are at least 90%, 95% or 99% identical in the VH (SEQ ID NO: 4) and/or VL (SEQ ID NO: 7) domain to the VH (SEQ ID NO: 4) or VL (SEQ ID NO: 7) domains of FIG. 1 or 2, are included in the invention. Reference to the 90%, 95%, or 99% identity may be to the framework regions of the VH (SEQ ID NO: 4) and/or VL (SEQ ID NO: 7) domains. In particular, the CDR regions may be identical, but the framework regions may vary by up to 1%, 5%, or 10%. Preferably such antibodies differ from the sequences of FIG. 1 or 2 by a small number of functionally inconsequential amino acid substitutions (e.g., conservative substitutions), deletions, or insertions. In any embodiment of the invention, the specific binding pair may be an antibody or an antibody fragment, Fab, (Fab')2, scFv, Fv, dAb, Fd or a diabody. In some embodiments the antibody is a polyclonal antibody. In other embodiments the antibody is a monoclonal antibody. Antibodies of the invention may be humanised, chimeric or veneered antibodies, or may be non-human antibodies of any species. In one embodiment the specific binding partner of the invention is mouse antibody FG129 which comprises a heavy chain as depicted in FIG. 1a and a light chain as depicted in FIG. 1b.

In another embodiment the specific binding partner of the invention is chimeric antibody FG129 which comprises a heavy chain as depicted in FIG. 2a and a light chain as depicted in FIG. 2b.

Specific binding members of the invention may carry a detectable or functional label.

In further aspects, the invention provides an isolated nucleic acid which comprises a sequence encoding a specific binding member of the aspects of the invention, and methods of preparing specific binding members of the invention which comprise expressing said nucleic acids under conditions to bring about expression of said binding member, and recovering the binding member.

Specific binding members according to the invention may be used in a method of treatment or diagnosis of the human or animal body, such as a method of treatment of a tumour in a patient (preferably human) which comprises administering to said patient an effective amount of a specific binding member of the invention. The invention also provides a specific binding member of the present invention for use in medicine, as well as the use of a specific binding member of the present invention in the manufacture of a medicament for the diagnosis or treatment of a tumour.

The invention also provides the antigen to which the specific binding members of the present invention bind. In one embodiment, a sialyl-di-Lewis$^a$ which is capable of being bound, preferably specifically, by a specific binding member of the present invention is provided. The sialyl-di-Lewis$^a$ may be provided in isolated form, and may be used in a screen to develop further specific binding members therefor. For example, a library of compounds may be screened for members of the library which bind specifically to the sialyl-di-Lewis$^a$. The sialyl-di-Lewis$^a$ may on a protein backbone. When on a protein backbone, it may have a molecular weight of about 50-150 kDa, as determined by SDS-PAGE.

In a further aspect the invention provides an isolated specific binding member capable of specifically binding sialyl-di-Lewis$^a$ and sialyl-Lewis$^{a-x}$ for use in the diagnosis or prognosis of colorectal, gastric, pancreatic, lung, ovarian and breast tumours. In a further aspect the invention provides an isolated specific binding member capable of specifically binding sialyl-di-Lewis$^a$ and sialyl-Lewis$^{a-x}$ and mono-sialyl-Lewis$^a$ only attached to a glycoprotein for use in the diagnosis or prognosis of colorectal, gastric, pancreatic, lung, ovarian and breast tumours.

The invention further provides a method for diagnosis of cancer comprising using a specific binding partner of the invention to detect sialyl-di-Lewis$^a$ and sialyl-Lewis$^{a-x}$ and mono-sialyl-Lewis$^a$ only attached to a glycoprotein in a sample from an individual. In some embodiments, in the diagnostic method the pattern of glycans detected by the binding partner is used to stratify therapy options for the individual.

These and other aspects of the invention are described in further detail below.

As used herein, a "specific binding member" is a member of a pair of molecules which have binding specificity for one another. The members of a specific binding pair may be naturally derived or wholly or partially synthetically produced. One member of the pair of molecules has an area on its surface, which may be a protrusion or a cavity, which specifically binds to and is therefore complementary to a particular spatial and polar organisation of the other member of the pair of molecules. Thus, the members of the pair have the property of binding specifically to each other. Examples of types of specific binding pairs are antigen-antibody, biotin-avidin, hormone-hormone receptor, receptor-ligand, enzyme-substrate. The present invention is generally concerned with antigen-antibody type reactions, although it also concerns small molecules which bind to the antigen defined herein.

As used herein, "treatment" includes any regime that can benefit a human or non-human animal, preferably mammal. The treatment may be in respect of an existing condition or may be prophylactic (preventative treatment).

As used herein, a "tumour" is an abnormal growth of tissue. It may be localised (benign) or invade nearby tissues (malignant) or distant tissues (metastatic). Tumours include neoplastic growths which cause cancer and include oesophageal, colorectal, gastric, breast and endometrial tumours, as well as cancerous tissues or cell lines including, but not limited to, leukaemic cells. As used herein, "tumour" also includes within its scope endometriosis.

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies. Antibodies may be polyclonal or monoclonal. A monoclonal antibody may be referred to as a "mAb".

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, humanised antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023. A humanised antibody may be a modified antibody having the variable regions of a non-human, e.g., murine, antibody and the constant region of a human antibody. Methods for making humanised antibodies are described in, for example, U.S. Pat. No. 5,225,539.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment [25] which consists of a VH domain; (v) isolated CDR regions; (vi) F(ab')2 fragments, a bivalent fragment comprising two linked Fab fragments; (vii) single chain Fv molecules (scFv), wherein a VH domain and a VL domain are linked by a peptide linker which allows the two domains to associate to form an antigen binding site [26, 27]; (viii) bispecific single chain Fv dimers (PCT/US92/09965) and; (ix) "diabodies", multivalent or multispecific fragments constructed by gene fusion (WO94/13804; [28]).

Diabodies are multimers of polypeptides, each polypeptide comprising a first domain comprising a binding region of an immunoglobulin light chain and a second domain comprising a binding region of an immunoglobulin heavy chain, the two domains being linked (e.g., by a peptide linker) but unable to associated with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways [29], e.g., prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction.

Other forms of bispecific antibodies include the single chain "Janusins" described in [30].

Bispecific diabodies, as opposed to bispecific whole antibodies, may also be useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

The term "sialyl-di-Lewis$^a$" refers to the structure:
Neu5Acα2-3 Galβ1-3 (Fucα1-4)GlcNAcβ1-3 Galβ 1-3 (Fucα1-4)GlcNAcβ.

The term "mono sialyl-Lewis$^a$" refers to the structure:
Neu5Acα2-3Galb1-3 (Fuca1-4)GlcNAcb.

The term "sialyl-Lewis$^{a-x}$" refers to the structure:
Neu5Acα2-3Galb1-3(Fucα1-4)GlcNAcb1-3Galb1-4 (Fucα1-3)GlcNAcb.

An "antigen binding domain" is the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. An antigen binding domain may comprise an antibody light chain variable region (VL) and an antibody heavy chain variable region (VH).

"Specific" is generally used to refer to the situation in which one member of a specific binding pair will not show any significant binding to molecules other than its specific binding partner(s), and, e.g., has less than about 30% cross reactivity with any other molecule. In other embodiments it has less than 20%, 10%, or 1% cross reactivity with any other molecule. The term is also applicable where e.g., an antigen binding domain is specific for a particular epitope which is carried by a number of antigens, in which case, the specific binding member carrying the antigen binding domain will be able to bind to the various antigens carrying the epitope.

"Isolated" refers to the state in which specific binding members of the invention or nucleic acid encoding such binding members will preferably be, in accordance with the present invention. Members and nucleic acid will generally be free or substantially free of material with which they are naturally associated such as other polypeptides or nucleic acids with which they are found in their natural environment, or the environment in which they are prepared (e.g., cell culture) when such preparation is by recombinant DNA technology practised in vitro or in vivo. Specific binding members and nucleic acid may be formulated with diluents or adjuvants and still for practical purposes be isolated—for example, the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells, or they may be (for example if produced by expression in a prokaryotic cell) unglycosylated.

By "substantially as set out" it is meant that the CDR regions of the invention will be either identical or highly homologous to the specified regions of FIG. 1 or 2. By "highly homologous" it is contemplated that from 1 to 5, from 1 to 4, from 1 to 3, 2 or isubstitutions may be made in the CDRs.

The invention also includes within its scope polypeptides having the amino acid sequence as set out in FIG. 1 or 2, polynucleotides having the nucleic acid sequences as set out in Figure A or B and sequences having substantial identity thereto, for example, 70%, 80%, 85%, 90%, 95% or 99% identity thereto. The percent identity of two amino acid sequences or of two nucleic acid sequences is generally determined by aligning the sequences for optimal comparison purposes (e.g., gaps can be introduced in the first sequence for best alignment with the second sequence) and comparing the amino acid residues or nucleotides at corresponding positions. The "best alignment" is an alignment of two sequences that results in the highest percent identity. The percent identity is determined by comparing the number of identical amino acid residues or nucleotides within the sequences (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) [31], modified as in Karlin and Altschul (1993) [32]. The NBLAST and XBLAST programs of Altschul et al. (1990) [33] have incorporated such an algorithm. BLAST nucleotide searches can be performed with the NBLAST program, score=100, word length=12 to obtain nucleotide sequences homologous to a nucleic acid molecules of the invention. BLAST protein searches can be performed with the XBLAST program, score=50, word length=3 to obtain amino acid sequences homologous to a protein molecules of the invention. To obtain gapped alignments for comparison purposes, Gapped BLAST can be utilized as described in Altschul et al. (1997) [34]. Alternatively, PSI-Blast can be used to perform an iterated search that detects distant relationships between molecules (Id.). When utilizing BLAST, GappedBLAST, and PSI-Blast programs, the default parameters of the respective programs (e.g., XBLAST and NBLAST) can be used. See http://www.ncbi.nlm.nih.gov. Another example of a mathematical algorithm utilized for the comparison of sequences is the algorithm of Myers and Miller, [35]. The ALIGN program (version 2.0) which is part of the GCG sequence alignment software package has incorporated such an algorithm. Other algorithms for sequence analysis known in the art include ADVANCE and ADAM as described in Torellis and Robotti (1994) [36]; and FASTA described in Pearson and Lipman (1988) [37]. Within FASTA, ktup is a control option that sets the sensitivity and speed of the search.

Isolated specific binding members of the present invention are capable of binding to a sialyl-di-Lewis$^a$ carbohydrate, which may be a sialyl-di-Lewis$^a$ on a protein moiety. In one embodiment, the CDR3 regions, comprising the amino acid sequences substantially as set out as residues 98-106 (CDRH3) of FIGS. 1a and 2a and 95 to 103 of FIGS. 1b and 2b, are carried in a structure which allows the binding of these regions to a sialyl-di-Lewis$^a$ carbohydrate.

The structure for carrying the CDR3s of the invention will generally be of an antibody heavy or light chain sequence or substantial portion thereof in which the CDR3 regions are located at locations corresponding to the CDR3 region of naturally-occurring VH and VL antibody variable domains encoded by rearranged immunoglobulin genes. The structures and locations of immunoglobulin variable domains may be determined by reference to the web site imgt.org. The amino acid sequence substantially as set out as residues 98-106 (SEQ ID NO: 3) of FIGS. 1a and 2a may be carried as the CDR3 in a human heavy chain variable domain or a substantial portion thereof, and the amino acid sequence substantially as set out as residues and 95-103 (SEQ ID NO: 6) of FIGS. 1b and 2b may be carried as the CDR3 in a human light chain variable domain or a substantial portion thereof.

The variable domains may be derived from any germline or rearranged human variable domain, or may be a synthetic variable domain based on consensus sequences of known human variable domains. The CDR3-derived sequences of the invention may be introduced into a repertoire of variable domains lacking CDR3 regions, using recombinant DNA technology.

For example, Marks et al., (1992) [38] describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. (1992) [38] further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide specific binding members of the invention. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members.

Analogous shuffling or combinatorial techniques are also disclosed by Stemmer (1994) [39] who describes the technique in relation to a β-lactamase gene but observes that the approach may be used for the generation of antibodies. A further alternative is to generate novel VH or VL regions carrying the CDR3-derived sequences of the invention using random mutagenesis of, for example, the FG129 VH or VL genes to generate mutations within the entire variable domain. Such a technique is described by Gram et al., (1992) [40], who used error-prone PCR.

Another method which may be used is to direct mutagenesis to CDR regions of VH or VL genes. Such techniques are disclosed by Barbas et al., (1994) [41] and Schier et al., (1996) [42].

A substantial portion of an immunoglobulin variable domain will generally comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps, including the introduction of linkers to join variable domains of the invention to further protein sequences including immunoglobulin heavy chains, other variable domains (for example in the production of diabodies) or protein labels as discussed in more detail below.

One embodiment of the invention provides specific binding members comprising a pair of binding domains based on the amino acid sequences for the VL and VH regions substantially as set out in FIG. 1, i.e. amino acids 1 to 117 (VH) (SEQ ID NO: 4) of FIGS. 1a and 2a and amino acids 1 to 114 (VL) (SEQ ID NO: 7) of FIGS. 1b and 2b. Single binding domains based on either of these sequences form further aspects of the invention. In the case of the binding domains based on the amino acid sequence for the VH region (SEQ ID NO: 4) substantially set out in FIGS. 1a and 2a, such binding domains may be used as targeting agents since it is known that immunoglobulin VH domains are capable of binding target antigens in a specific manner.

In the case of either of the single chain specific binding domains, these domains may be used to screen for complementary domains capable of forming a two-domain specific binding member which has in vivo properties as good as or equal to the FG88 antibodies disclosed herein.

This may be achieved by phage display screening methods using the so-called hierarchical dual combinatorial approach as disclosed in WO92/01047 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al., [38].

Specific binding members of the present invention may further comprise antibody constant regions or parts thereof. For example, specific binding members based on the VL region (SEQ ID NO: 7) shown in FIGS. 1b and 2b may be attached at their C-terminal end to antibody light chain constant domains including human Cκ or Cλ chains. Similarly, 5 specific binding members based on VL region (SEQ ID NO: 7) shown in FIGS. 1b and 2b may be attached at their C-terminal end to all or part of an immunoglobulin heavy chain derived from any antibody isotype, e.g., IgG, IgA, IgE and IgM and any of the isotype sub-classes, particularly IgG1, IgG2 and IgG4.

In one embodiment, the binding member is an scFv comprising, in the following order 1) a leader sequence, 2) a heavy chain variable region, 3) 3×GGGGS spacer, 4) a light chain variable region, and 5) poly-Ala and a 6×His tag for purification. In another embodiment, the binding member is an scFv comprising, in the following order 1) a leader sequence, 2) a light chain variable region, 3) 3×GGGGS spacer, and 4) a heavy chain variable region, optionally further comprising either 5' or 3' purification tags. In another embodiment, the binding member is provided in the form of a chimeric antigen receptor (CAR). CARs may also be known as artificial T cell receptors, chimeric T cell receptors, or chimeric immunoreceptors. In an embodiment, where the binding member is an scFv provided in the form of a chimeric antigen receptor (CAR), it may be provided in either the heavy chain-light chain orientation or the light chain-heavy chain orientation.

Specific binding members of the present invention can be used in methods of diagnosis and treatment of tumours in human or animal subjects. When used in diagnosis, specific binding members of the invention may be labelled with a detectable label, for example a radiolabel such as $^{131}$I or $^{99}$Tc, which may be attached to specific binding members of the invention using conventional chemistry known in the art of antibody imaging. Labels also include enzyme labels such as horseradish peroxidase. Labels further include chemical moieties such as biotin which may be detected via binding to a specific cognate detectable moiety, e.g., labelled avidin.

Although specific binding members of the invention have in themselves been shown to be effective in killing cancer cells, they may additionally be labelled with a functional label. Functional labels include substances which are designed to be targeted to the site of cancer to cause destruction thereof. Such functional labels include toxins such as ricin and enzymes such as bacterial carboxypeptidase or nitroreductase, which are capable of converting prodrugs into active drugs. In addition, the specific binding members may be attached or otherwise associated with chemotherapeutic or cytotoxic agents, such as maytansines (DM1 and DM4), onides, auristatins, calicheamicin, duocamycin, doxorubicin or radiolabels, such as $^{90}$Y or $^{131}$I.

Furthermore, the specific binding members of the present invention may be administered alone or in combination with other treatments, either simultaneously or sequentially, dependent upon the condition to be treated. Thus, the present invention further provides products containing a specific binding member of the present invention and an active agent as a combined preparation for simultaneous, separate or sequential use in the treatment of a tumour. Active agents may include chemotherapeutic or cytotoxic agents including, 5-Fluorouracil, cisplatin, Mitomycin C, oxaliplatin and tamoxifen, which may operate synergistically with the binding members of the present invention. Other active agents may include suitable doses of pain relief drugs such as non-steroidal anti-inflammatory drugs (e.g., aspirin, paracetamol, ibuprofen or ketoprofen) or opitates such as morphine, or anti-emetics.

Whilst not wishing to be bound by theory, the ability of the binding members of the invention to synergise with an active agent to enhance tumour killing may not be due to immune effector mechanisms but rather may be a direct consequence of the binding member binding to cell surface bound to sialyl-di-Lewis$^a$ and sialyl-Lewis$^{a-x}$ and mono-sialyl-Lewis$^a$ only attached to a glycoprotein.

Specific binding members of the present invention will usually be administered in the form of a pharmaceutical composition, which may comprise at least one component in addition to the specific binding member.

The pharmaceutical composition may comprise, in addition to active ingredient, a pharmaceutically acceptable excipient, diluent, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g., intravenous.

It is envisaged that injections will be the primary route for therapeutic administration of the compositions although delivery through a catheter or other surgical tubing is also used. Some suitable routes of administration include intravenous, subcutaneous, intraperitoneal and intramuscular administration. Liquid formulations may be utilised after reconstitution from powder formulations.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Where the formulation is a liquid it may be, for example, a physiologic salt solution containing non-phosphate buffer at pH 6.8-7.6, or a lyophilised powder.

The composition may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Implantable or microcapsular sustained release matrices include polylactides (U.S. Pat. No. 3,773,919; EP-A-0058481) copolymers of L-glutamic acid and gamma ethyl-L-glutamate [43], poly (2-hydroxyethyl-methacrylate). Liposomes containing the polypeptides are prepared by well-known methods: DE 3,218, 121A; Epstein et al, PNAS USA, 82: 3688-3692, 1985; Hwang et al, PNAS USA, 77: 4030-4034, 1980; EP-A-0052522; EP-A-0036676; EP-A-0088046; EP-A-0143949; EP-A-0142541; JP-A-83-11808; U.S. Pat. Nos. 4,485,045 and 4,544,545. Ordinarily, the liposomes are of the small (about 200-800 Angstroms) unilamellar type in which the lipid content is greater than about 30 mol. % cholesterol, the selected proportion being adjusted for the optimal rate of the polypeptide leakage.

The composition may be administered in a localised manner to a tumour site or other desired site or may be delivered in a manner in which it targets tumour or other cells.

The compositions are preferably administered to an individual in a "therapeutically effective amount", this being sufficient to show benefit to the individual. The actual amount administered, and rate and time-course of administration, will depend on the nature and severity of what is being treated. Prescription of treatment, e.g., decisions on dosage etc, is within the responsibility of general practitioners and other medical doctors, and typically takes account of the disorder to be treated, the condition of the individual patient, the site of delivery, the method of administration and other factors known to practitioners. The compositions of the invention are particularly relevant to the treatment of existing tumours, especially cancer, and in the prevention of the recurrence of such conditions after initial treatment or surgery. Examples of the techniques and protocols mentioned above can be found in Remington's Pharmaceutical Sciences, 16$^{th}$ edition, Oslo, A. (ed), 1980 [45].

The optimal dose can be determined by physicians based on a number of parameters including, for example, age, sex, weight, severity of the condition being treated, the active ingredient being administered and the route of administration. In general, a serum concentration of polypeptides and antibodies that permits saturation of receptors is desirable. A concentration in excess of approximately 0.1 nM is normally sufficient. For example, a dose of 100 mg/m$^2$ of antibody provides a serum concentration of approximately 20 nM for approximately eight days.

As a rough guideline, doses of antibodies may be given weekly in amounts of 10-300 mg/m$^2$. Equivalent doses of antibody fragments should be used at more frequent intervals in order to maintain a serum level in excess of the concentration that permits saturation of the LecLe$^x$ carbohydrate.

The dose of the composition will be dependent upon the properties of the binding member, e.g., its binding activity and in vivo plasma half-life, the concentration of the polypeptide in the formulation, the administration route, the site and rate of dosage, the clinical tolerance of the patient involved, the pathological condition afflicting the patient and the like, as is well within the skill of the physician. For example, doses of 300 □g of antibody per patient per administration are preferred, although dosages may range from about 10 µg to 6 mg per dose. Different dosages are utilised during a series of sequential inoculations; the practitioner may administer an initial inoculation and then boost with relatively smaller doses of antibody.

This invention is also directed to optimise immunisation schedules for enhancing a protective immune response against cancer.

The binding members of the present invention may be generated wholly or partly by chemical synthesis. The binding members can be readily prepared according to well-established, standard liquid or, preferably, solid-phase peptide synthesis methods, general descriptions of which are broadly available (see, for example, in J. M. Stewart and J. D. Young, (1984) [46], in M. Bodanzsky and A. Bodanzsky, (1984) [47]; or they may be prepared in solution, by the liquid phase method or by any combination of solid-phase, liquid phase and solution chemistry, e.g., by first completing the respective peptide portion and then, if desired and appropriate, after removal of any protecting groups being present, by introduction of the residue X by reaction of the respective carbonic or sulfonic acid or a reactive derivative thereof.

Another convenient way of producing a binding member according to the present invention is to express the nucleic acid encoding it, by use of nucleic acid in an expression system.

The present invention further provides an isolated nucleic acid encoding a specific binding member of the present invention. Nucleic acid includes DNA and RNA. In a preferred aspect, the present invention provides a nucleic acid which codes for a specific binding member of the invention as defined above. Examples of such nucleic acid are shown in FIGS. 1 and 2. The skilled person will be able to determine substitutions, deletions and/or additions to such nucleic acids which will still provide a specific binding member of the present invention.

The present invention also provides constructs in the form of plasmids, vectors, transcription or expression cassettes which comprise at least one nucleic acid as described above. The present invention also provides a recombinant host cell which comprises one or more constructs as above. As mentioned, a nucleic acid encoding a specific binding member of the invention forms an aspect of the present invention, as does a method of production of the specific binding member which method comprises expression from encoding nucleic acid therefor. Expression may conveniently be achieved by culturing under appropriate conditions recombinant host cells containing the nucleic acid. Following production by expression, a specific binding member may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*. The expression of antibodies and antibody fragments in prokaryotic cells such as *E. coli* is well established in the art. For a review, see for example Plückthun (1991) [48]. Expression in eukaryotic cells in culture is also available to those skilled in the art as an option for production of a specific binding member, see for recent review, for example Reff (1993) [49]; Trill et al., (1995) [50].

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g., 'phage, or phagemid, as appropriate. For further details see, for example, Sambrook et al., (1989) [51]. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al., (1992)[52].

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g., by culturing host cells under conditions for expression of the gene.

In one embodiment, the nucleic acid of the invention is integrated into the genome (e.g., chromosome) of the host cell. Integration may be promoted by inclusion of sequences which promote recombination with the genome, in accordance with standard techniques.

According to another aspect of the present invention, there is provided a binding member which competes for binding to the same epitope as a binding member according to the invention. The competing binding member is in the same format as the binding member according to the invention described herein, but with different CDR or variable region sequences.

The present invention also provides a method which comprises using a construct as stated above in an expression system in order to express a specific binding member or polypeptide as above.

Preferred features of each aspect of the invention are as for each of the other aspects mutatis mutandis. The prior art documents mentioned herein are incorporated to the fullest extent permitted by law.

BRIEF DESCRIPTION OF THE DRAWINGS

Figure Legends

FIG. 1a: Amino acid and nucleotide sequence for the mouse IgG1 heavy chain of the FG129 mAb (SEQ ID NO: 1). Numbers refer to the standardised IMGT system for the numbering of antibody sequences [59]. FIG. 1b: Amino acid and nucleotide sequence for the mouse kappa chain of the FG129 mAb. Numbers refer to the standardised IMGT system for the numbering of antibody sequences [59].

Figure 2A:
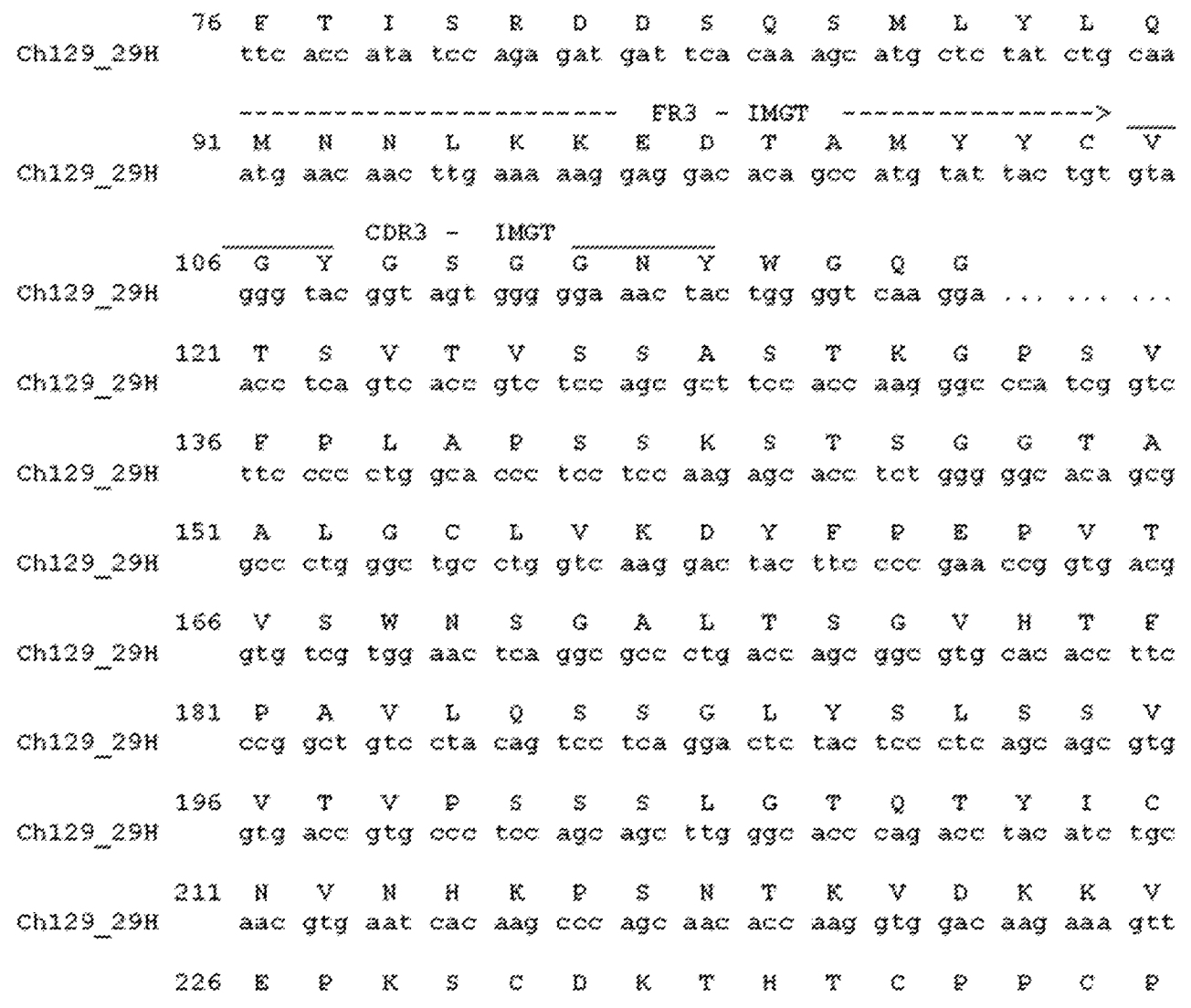
Figure 2A:
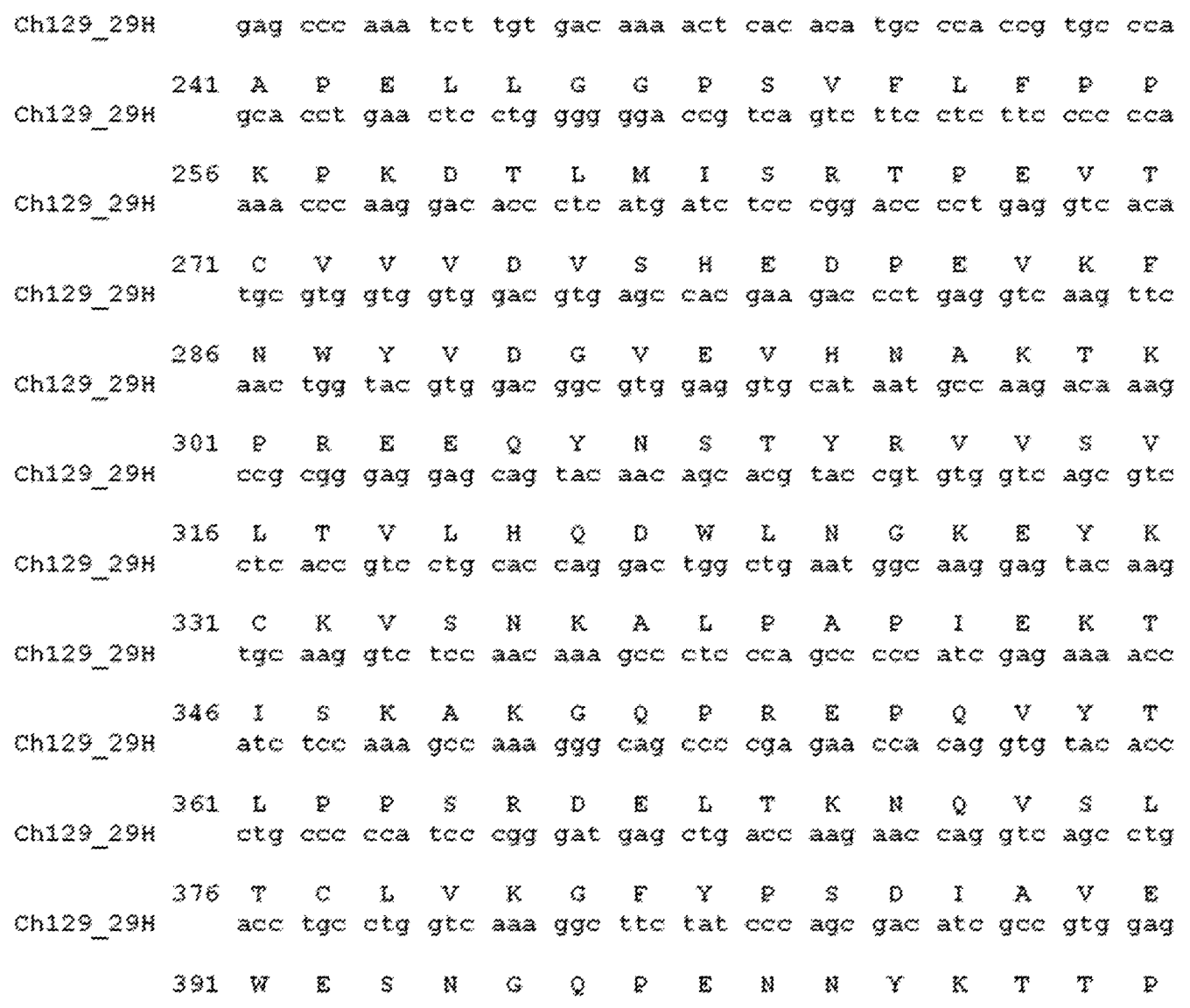

FIG. 2: The chimeric version of the FG129 mAb (original murine variable regions linked to human constant region sequence), produced by a transfected cell line, binds the target cell line (HCT-15). FIG. 2a: Amino acid and nucleotide sequence for the human IgG1 heavy chain of the FG129 mAb. Numbers refer to the standardised IMGT system for the numbering of antibody sequences [59]. FIG. 2b: Amino acid and nucleotide sequence for the human kappa chain of the FG129 mAb. Numbers refer to the standardised IMGT system for the numbering of antibody sequences [59].

FIG. 13a: Sequence of FG129-scFv, comprised of 1) leader sequence, 2) heavy chain variable region, 3) 3×GGGGS spacer, 4) light chain variable region, 5) poly-Ala and 6×His tag for purification.

DETAILED DESCRIPTION OF THE INVENTION

Figure 3A:
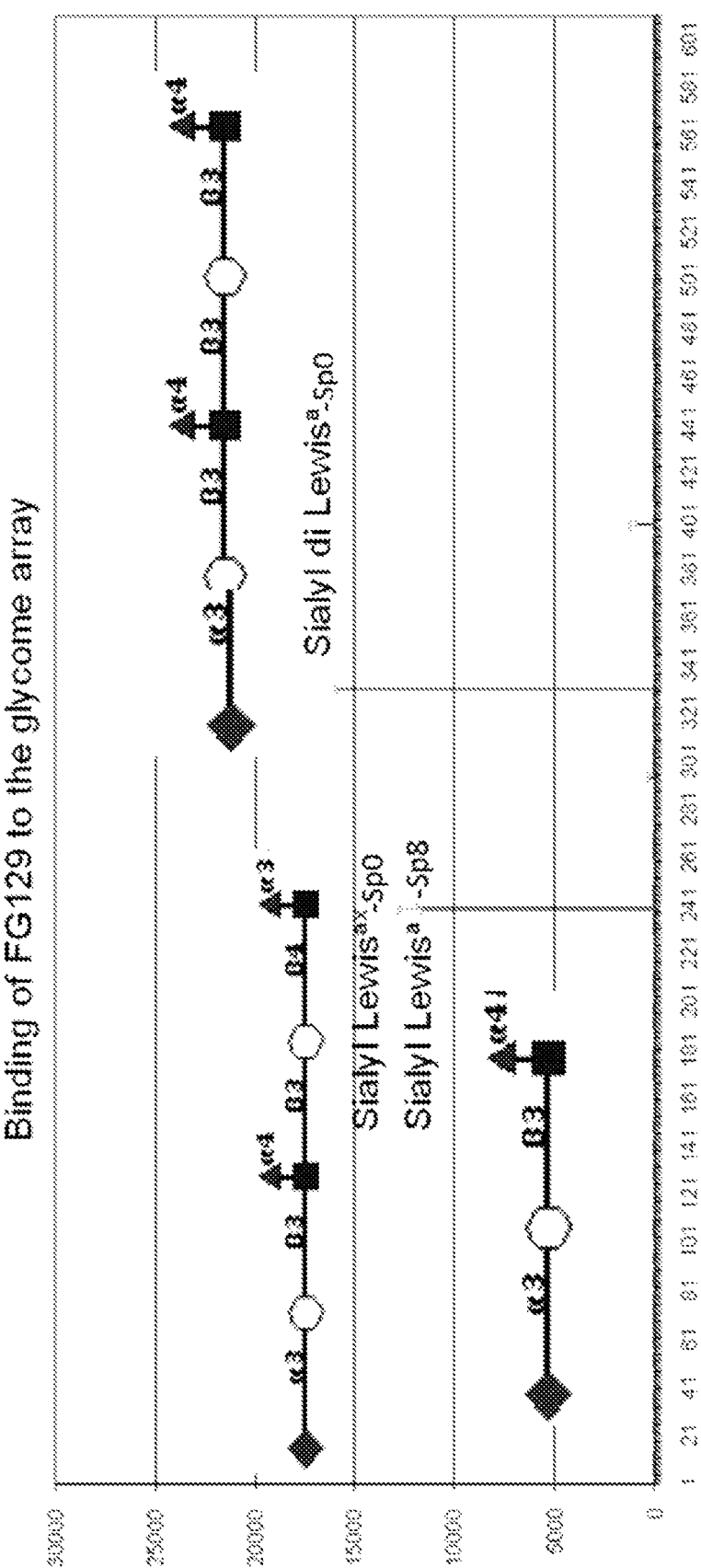
FIG. 3a: ELISA screening of FG129 to over 600 glycans arrayed on a glass slide by the CFG. Square represents glucosylamine, circle represents galactose, triangle represents fucose and diamond represents sialic acid.

The invention will now be described further in the following non-limiting examples and accompanying drawings.
Methods
Binding to Tumour Cell Lines:

$1\times10^5$ cancer cells were incubated with 50 µl of primary antibodies at 4° C. for 1 hr. Cells were washed with 200 µl of RPMI 10% new born calf serum (NBCS: Sigma, Poole, UK) and spun at 1,000 rpm for 5 min. Supernatant was discarded and 50 µl of FITC conjugated anti-mouse IgG Fc specific mab (Sigma; 1/100 in RPMI 10% NBCS) was used as secondary antibody. Cells were incubated at 4° C. in dark for 1 hr then washed with 200 µl RPMI 10% NBCS and spun at 1,000 rpm for 5 min. After discarding supernatant, 0.4% formaldehyde was used to fix the cells. Samples were analysed on a Beckman coulter FC-500 flow cytometer (Beckman Coulter, High Wycombe, UK). To analyse and plot raw data, WinMDI 2.9 software was used. Cellular antibody binding sites for FG129 (used at 30 µg/ml) were calculated using the QIFIKIT® (Dako UK Ltd) according to the manufacturer's recommendations. Specific antibody binding capacity (SABC) was obtained by subtracting the non-specific binding of an isotype control.

Binding to Blood:

50 µl of healthy donor blood was incubated with 50 µl primary antibody at 4° C. for 1 hr. The blood was washed with 150 µl of RPMI 10% NBCS and spun at 1,000 rpm for 5 min. Supernatant was discarded and 50 µl FITC conjugated anti-mouse IgG Fc specific mAb (1/100 in RPMI 10% NBCS) was used as the secondary antibody. Cells were incubated at 4° C. in the dark for 1 hr then washed with 150 µl RPMI 10% NBCS and spun at 1,000 rpm for 5 min. After discarding the supernatant, 50 µl/well Cal-Lyse (Invitrogen, Paisley, UK) was used followed by 500 µl/well distilled water to lyse red blood cells. The blood was subsequently spun at 1,000 rpm for 5 min. Supernatant was discarded and 0.4% formaldehyde was used to fix the cells. Samples were analysed on a FC-500 flow cytometer (Beckman Coulter). To analyse and plot raw data, WinMDI 2.9 software was used.

Plasma Membrane Glycolipid Extraction:

Colo205 cell pellet ($5\times10^7$ cells) was resuspended in 500 µl of Mannitol/HEPES buffer (50 mM Mannitol, 5 mM HEPES, pH7.2, both Sigma) and passed through 3 needles (23G, 25G, 27G) each with 30 pulses. 5 µl of 1M $CaCl_2$ was added to the cells and passed through 3 needles each with 30 pulses as above. Sheared cells were incubated on ice for 20 min then spun at 3,000 g for 15 min at room temperature. Supernatant was collected and spun at 48,000 g for 30 min at 4° C. and the supernatant was discarded. The pellet was resuspended in 1 ml methanol followed by 1 ml chloroform and incubated with rolling for 30 min at room temperature. The sample was then spun at 1,200 g for 10 min to remove precipitated protein. The supernatant, containing plasma membrane glycolipids, was collected and stored at −20° C.

Glycome Analysis:

To clarify the fine specificities of the FG129 mAbs further, the antibodies were sent to the Consortium for Functional Glycomics where they were screened against ≥600 natural and synthetic glycans. Briefly, synthetic and mammalian glycans with amino linkers were printed onto N-hydroxysuccinimide (NHS)-activated glass microscope slides, forming amide linkages. Printed slides were incubated with 1 µg/ml of antibody for 1 hr before the binding was detected with Alexa488-conjugated goat anti-mouse IgG. Slides were then dried, scanned and the screening data compared to the Consortium for Functional Glycomics database.

Affinity Analysis

Surface Plasmon Resonance (SPR, Biacore X or 3000, GE Healthcare) analysis was used to investigate real-time binding kinetics of the FG129 mAbs. Polyvalent sialyl Le$^a$-HSA (Isosep AB, Tullinge, Sweden) was coupled onto a CM5 biosensor chip according to the manufacturer's instructions and a reference cell was treated in a similar manner, but omitting the sialyl Le$^a$ conjugate. FG129, CH129 and scFv129 mAbs diluted in HBS-P buffer (10 mmol/L HEPES, pH 7.4, 150 mmol/L NaCl, 0.005% (v/v) surfactant P20) were run across the chip at a flow rate of 50 µl/min and BIAevaluation software 4.1 was used to determine the kinetic binding parameters from which affinities are calculated.

Lewis Antigen and Saliva Sandwich ELISA

ELISA plates were coated overnight at 4° C. with 100 ng/well Lewis-HSA antigens (Isosep), blocked with PBS/BSA and incubated with primary mAbs (direct ELISA).

Antibody or Lewis antigen binding was detected using biotinylated secondary mAb (Sigma). Plates were read at 450 nm by Tecan Infinite F50 after incubation with Streptavidin Horseradish Peroxidase (HRPO) conjugate (Invitrogen).

SDS-PAGE and Western Blot Analysis:

Briefly, $1 \times 10^5$ or $10^6$ cell equivalents of Colo205 cell lysate, plasma membrane, total lipid extract, plasma membrane lipid extract or HCT-15 cell lysates were analysed for FG129 binding. Tumour cell total and plasma membrane lipid extracts and cell lysates were reduced with dithiothreitol (DTT; Pierce Biotechnology, ThermoFisher, Loughborough, UK) and subjected to SDS-PAGE using NOVEX 4% to 12% Bis-Tris gels (Invitrogen), and transferred to Immobilon-FL PVDF membrane (Merck Millipore, Watford, UK) using 1× transfer buffer (20×, Invitrogen) and 20% (v/v) methanol at 30V for 1 hr. Membranes were blocked with 5% (w/v) non-fat dry milk in 0.05% (v/v) Tween-PBS for 1 hr then probed with primary antibodies diluted in Tween-PBS, 2% BSA for 1 hr. Primary antibody binding was detected using biotin-conjugated anti-mouse IgG Fc specific secondary antibody (Sigma; 1/2000 dilution in Tween-PBS, 2% BSA) for 1 hr, and visualized using IRDye 800CW streptavidin (LICOR Biosciences, UK; 1/1000 in Tween-PBS 2% BSA).

Identification of FG129 Heavy and Light Chain Variable Regions.

Cell Source and Total RNA Preparation:

Approximately $5 \times 10^6$ cells from hybridomasFG129 were taken from tissue culture, washed once in PBS, and the cell pellet treated with 500 µl Trizol (Invitrogen). After the cells had been dispersed in the reagent, they were stored at −80° C. until RNA was prepared following manufacturer's protocol. RNA concentration and purity were determined by Nanodrop. Prior to cDNA synthesis, RNA was DNase I treated to remove genomic DNA contamination (DNase I recombinant, RNase-free, Roche Diagnostics, Burgess Hill, UK) following manufacturer's recommendations.

cDNA Synthesis:

First-strand cDNA was prepared from 3 µg of total RNA using a first-strand cDNA synthesis kit and AMV reverse transcriptase following manufacturer's protocol (Roche Diagnostics). After cDNA synthesis, reverse transcriptase activity was destroyed by incubation at 90° C. for 10 mins and cDNA stored at −20° C.

GAPDH PCR to Assess cDNA Quality:

A PCR was used to assess cDNA quality; primers specific for the mouse GAPDH house-keeping gene (5'-TTAGCAC-CCCTGGCCAAGG-3' (SEQ ID NO: 16) and 5'-CT-TACTCCCTTGGAGGCCATG-3' (SEQ ID NO: 17)) were used with a hot-start Taq polymerase (AmpliTaq Gold 360, Invitrogen) for 35 cycles (95° C., 3 mins followed by 35 cycles of 94° C./30 secs, 55° C./30 secs, 72° C./1 min; final polishing step of 10 mins at 72° C.). Amplified products were assessed by agarose gel electrophoresis.

PCR Primer Design for Cloning FG129 Variable Regions:

Primers were designed to amplify the heavy and light chain variable regions based upon the PCR product sequence data. Primers were designed to allow cloning of the relevant chain into unique restriction enzyme sites in the hIgG1/kappa double expression vector pDCOrig-hIgG1. Each 5' primer was targeted to the starting codon and leader peptide of the defined variable region, with a Kozak consensus immediately 5' of the starting codon. Each 3' primer was designed to be complementary to the joining region of the antibody sequence, to maintain reading frame after cloning of the chain, and to preserve the amino acid sequence usually found at the joining region/constant region junction. All primers were purchased from Eurofins MWG (Ebersberg, Germany).

Heavy Chain Variable Region PCR:

Immunoglobulin heavy chain variable region usage was determined using PCR with a previously published set of primers [60]. Previous results using a mouse mAb isotyping test kit (Serotec, Oxford, UK) had indicated that FG129 were both mouse IgG3 antibodies. Appropriate constant region reverse primers were therefore used to amplify from the constant regions. PCR amplification was carried out with 12 mouse VH region-specific 5' primers and 3' primers specific for previously determined antibody subclass with a hot-start Taq polymerase for 35 cycles (94° C., 5 min followed by 35 cycles of 94° C./1 min, 60° C./1 min, 72° C./2 min; final polishing step of 20 min at 72° C.). Amplified products were assessed by agarose gel electrophoresis. Positive amplifications resulted for the VH4 primer.

Light (κ) Chain Variable Region PCRs:

Immunoglobulin light chain variable region usage was determined using PCR with a previously published set of primers [60]. Previous results using a mouse mAb isotyping test kit had indicated that FG129 used κ light chains. PCR amplification was carried out with mouse Vκ region-specific 5' and 3' mouse Cκ specific primers with a hot-start Taq polymerase for 35 cycles (94° C., 5 mins followed by 35 cycles of 94° C./1 min, 60° C./1 min, 72° C./2 mins; final polishing step of 20 mins at 72° C.). Amplification products were assessed by agarose gel electrophoresis. Positive amplifications resulted with the VK1 and VK2 primers for FG129.

PCR Product Purification and Sequencing:

PCR products were purified using a Qiaquick PCR purification kit (Qiagen, Crawley, UK). The concentration of the resulting DNA was determined by Nanodrop and the purity assessed by agarose gel electrophoresis. PCR products were sequenced using the originating 5' and 3' PCR primers at the University of Nottingham DNA sequencing facility (http://www.nottingham.ac.uk/life-sciences/facilities/dna-sequencing/index.aspx). Sequences were analysed (V region identification, junction analysis) using the IMGT databasesearch facility (http://www.imgt.rg/IMGT_vquest/vquest?livret-0&Option=mouseIg). Sequencing indicated that FG129 had heavy and light chain variable regions from the following families; heavy chain; IGHV6-6*01, IGHJ1*01, light chain; IGKV12-41*01, IGKJ1*01. Sufficient residual constant region was present in the heavy chain sequences to confirm that FG129 was of the mIgG1 subclass.

Cloning Strategy:

The PCR product for cloning was generated using a proof-reading polymerase (Phusion, New England Biolabs) was cloned into a TA vector (pCR2.1; Invitrogen).

FG129 Heavy/Light Chain PCR for Cloning:

PCR amplification was carried out using a proof-reading polymerase (Phusion; NEB) and the cloning primers described above using the FG129 cDNA template previously described for 35 cycles (98° C., 3 min followed by 35 cycles of 98° C./30 sec, 58° C./30 sec, 72° C./45 sec; final polishing step of 3 min at 72° C.). Successful amplification was confirmed by agarose gel electrophoresis.

TOPO Light Chain Cloning:

Amplified FG129 light chain was treated with Taq polymerase (NEB) for 15 min at 72° C. to add 'A' overhangs compatible with TA cloning. Treated PCR product was incubated with the TOPO TA vector pCR2.1(Invitrogen) and transformed into chemically competent TOP10F' cells according to manufacturer's instructions. Transformed bacteria were spread on ampicillin (80 g/ml) supplemented LB agar plates, which were then incubated overnight at 37° C. Colonies were grown in liquid culture (LB supplemented with 80 g/ml ampicillin) and plasmid DNA prepared (spin miniprep kit, Qiagen). Presence of an insert was confirmed by sequential digestion with BsiWI and BamHI and agarose gel electrophoresis. Sequencing was carried out on miniprep DNA from colonies using T7 and M13rev primers. The DNA insert from one such colony had the predicted FG129 light chain sequence; a 300 ml bacterial LB/ampicillin culture was grown overnight and plasmid DNA prepared by maxiprep (plasmid maxi kit, Qiagen). Maxiprep DNA insert was confirmed by sequencing.

TOPO Heavy Chain Cloning:

Amplified FG129 heavy chain was treated with Taq polymerase (NEB) for 15 min at 72° C. to add 'A' overhangs. Treated PCR product was incubated with the TOPO TA vector pCR2.1 and transformed into chemically competent TOP10F' cells as above. Transformed bacteria were spread on ampicillin supplemented LB agar plates which were then incubated overnight at 37° C. Colonies were grown in liquid culture (LB/ampicillin) and plasmid DNA prepared (spin miniprep kit). Presence of an insert was confirmed by digestion with HindIII and AfeI and agarose gel electrophoresis. Sequencing was carried out on miniprep DNA from a number of colonies using T7 and M13rev primers. The DNA insert from one such colony had the predicted FG129 heavy chain sequence; a 300 ml bacterial LB/ampicillin culture was grown overnight and plasmid DNA prepared by maxiprep (plasmid maxi kit, Qiagen). Maxiprep DNA insert was confirmed by sequencing.

pDCOrig-hIgG1 Double Expression Vector Light Chain Cloning:

The FG129 light chain was digested from the TOPO vector pCR2.1 by sequential digestion with BsiWI and BamHI and the 400 bp insert DNA agarose gel purified using a QIAquick gel extraction kit (Qiagen) following manufacturer's recommendations. This insert was ligated into previously prepared pDCOrig-hIgG1 vector (see above) and transformed into chemically competent TOP10F' cells. Transformations were spread on 35 µg/ml Zeocin supplemented LB agar plates which were then incubated overnight at 37° C. Colonies were grown in liquid culture (LB supplemented with 35 g/ml Zeocin) and plasmid DNA prepared (spin miniprep kit, Qiagen). Sequencing was carried out on miniprep DNA from all colonies using a sequencing primer sited in the human kappa constant region. The DNA insert from one of the colonies had the predicted FG129 light chain sequence correctly inserted in pDCOrig-hIgG1; a 300 ml bacterial LB/zeocin culture was grown overnight and plasmid DNA prepared by maxiprep (plasmid maxi kit, Qiagen).

pDCOrig-hIgG1 Double Expression Vector Heavy Chain Cloning:

The FG129 heavy chain insert was digested from the TOPO vector pCR2.1 by digestion with HindIII and AfeI. Vector (pDCOrig-hIgG1-129k) containing the FG129 kappa light chain (prepared above) was also digested with HindIII and AfeI. The vector DNA was then phosphatase treated according to manufacturer's recommendations (Antarctic Phosphatase, NEB). After agarose gel electrophoresis, the 6.5 kb pDCOrig-hIgG1 vector band and 400 bp FG129H insert band were isolated using a QIAquick gel extraction kit (Qiagen) following manufacturer's recommendations. The insert was ligated into the pDCOrig-hIgG1 vector and transformed into chemically competentTOP10F' cells. Transformations were spread on 35 g/ml Zeocin supplemented LB agar plates which were then incubated overnight at 37° C. Colonies were grown in liquid culture (LB supplemented with 35 g/ml Zeocin) and plasmid DNA prepared (spin miniprep kit, Qiagen). Presence of an insert was confirmed by digestion with HindIII and AfeI and agarose gel electrophoresis. Sequencing was carried out on miniprep DNA from a number of the colonies using a sequencing primer sited in the human IgG1 constant region. The DNA insert from one of the colonies had the predicted FG129 heavy chain sequence correctly inserted in pDCOrig-hIgG1; a 300 ml bacterial LB/zeocin culture was grown overnight and plasmid DNA prepared by maxiprep (plasmid maxi kit, Qiagen). Sequencing was used to confirm that both heavy and light chain loci.

Expression, Purification and Characterisation of the Chimeric Antibody Constructs.

The methodology for the expression and purification of chimeric antibody described in the present invention can be achieved using methods well known in the art. Briefly, antibodies can be purified from supernatant collected from transiently, or subsequently stable, transfected cells by protein A or protein G affinity chromatography based on standard protocols, for example Sambrook et al. [61].

Cloning, Expression, Purification and Characterisation of the FG129-scFv

The heavy chain and light chain variable region were incorporated in silico into a single scFv sequence in the orientation; leader; heavy chain variable domain; spacer (3×GGGGS); light chain variable domain; spacer (6×Ala); purification tag (6×His) and synthesised. After cloning into a eukaryotic expression vector, Expi293 cells were transfected and allowed to produce protein transiently (6 days). His-tagged scFv was purified from Expi-293 supernatant using immobilised cobalt chromatography (HiTrap Talon 1 ml columns; GE Healthcare). In the binding assays, a biotinilated anti-His tag antibody was used as a secondary antibody (6×-His Epitope Tag Antibody, Biotin conjugated, clone HIS.H8; Thermo Fisher).

Immunohistochemistry Assessment for FG129:

To determine the therapeutic value of FG129, it was screened on pancreatic, lung, gastric, ovarian, colorectal cancer tissue microarrays by immunohistochemistry (IHC).

Methodology:

Immunohistochemistry was performed using the standard avidin-biotin peroxidase method. Paraffin embedded tissue sections were placed on a 60° C. hot block to melt the paraffin. Tissue sections were deparaffinised with xylene and rehydrated through graded alcohol. The sections were then immersed in 500 ml of citrate buffer (pH6) and heated for 20 min in a microwave (Whirlpool) to retrieve antigens. Endogenous peroxidase activity was blocked by incubating the tissue sections with endogenous peroxidase solution (Dako Ltd, Ely, UK) for 5 min. Normal swine serum (NSS; Vector Labs, CA, USA; 1/50 PBS) was added to each section for 20 min to block non-specific primary antibody binding. All sections were incubated with Avidin D/Biotin blocking kit (Vector Lab) for 15 min each in order to block non-specific binding of avidin and biotin. The sections were re-blocked with NSS (1/50 PBS) for 5 mins. Then tissue sections were incubated with primary antibody at room temperature for an hour. Anti-β-2-microglobulin (Dako Ltd; 1/100 in PBS) mAb and PBS alone were used as positive and negative controls respectively. Tissue sections were washed with PBS and incubated with biotinylated goat anti-mouse/rabbit immunoglobulin (Vector Labs; 1/50 in NSS) for 30 min at room temperature. Tissue sections were washed with PBS and incubated with preformed 1/50 (PBS) streptavidin-biotin/horseradish peroxidase complex (Dako Ltd) for 30 min at room temperature. 3, 3'-Diaminobenzidine tetra hydrochloride (DAB) was used as a substrate. Each section was incubated twice with 100 µl of DAB solution for 5 min. Finally, sections were lightly counterstained with haematoxylin (Sigma-Aldrich, Poole Dorset, UK) before dehydrating in graded alcohols, cleaning by immersing in xylene and mounting the slides with Distyrene, plasticiser, xylene (DPX) mountant (Sigma).

Patient Cohorts:

The study populations include cohorts of a consecutive series of 462 archived colorectal cancer (29) specimens (1994-2000; median follow up 42 months; censored December 2003; patients with lymph node positive disease routinely received adjuvant chemotherapy with 5-flurouracil/folinic acid), 350 ovarian cancer (28) samples (1982-1997; median follow up 192 months: censored November 2005: patients with stage II to IV disease received standard adjuvant chemotherapy which in later years was platinum based), 142 gastric cancer (26) samples (2001-2006; median follow up 66 months; censored January 2009; no chemotherapy) 68 pancreatic and 120 biliary/ampullary cancer (27) samples (1993-2010:median 45 months; censored 2012; 25-46% of patients received adjuvant chemotherapy with 5-fluorouracil/folinic acid and gemcitabine) 220 non small cell lung cancers (01/1996-07/2006: median follow up 36 months censored May 2013; none of the patients received chemotherapy prior to surgery but 11 patients received radiotherapy and 9 patients received at least 1 cycle of adjuvant chemotherapy post surgery) obtained from patients undergoing elective surgical resection of a histologically proven cancer at Nottingham or Derby University Hospitals. No cases were excluded unless the relevant clinico-pathological material/data were unavailable.

Confocal Microscopy:

FG129 and CH129 mAbs were labelled with Alexa-488 fluorophore (A-FG129, A-CH129) according to manufacturer's protocol (Invitrogen). $1.5 \times 10^5$ HCT-15 cells were grown on sterile circular coverslips (22 mm diameter, 0.16-0.19 mm thick) in a 6 well plate for 24 hr in 5% $CO_2$ at 37° C. 24 hours later, cells on coverslips were treated with 5 µg/ml of mAbs for 2 hr at 37° C. in the dark. 2 hours later, excess/unbound mAbs were washed away using PBS. The cells were then fixed using 0.4% paraformaldehyde for 20 min in the dark. 0.4% paraformaldehyde was washed away using PBS. The coverslips were mounted to slides with PBS:glycerol (1:1). The coverslip edge was sealed with clear nail varnish. Localisation of A-FG129 and A-CH129 mAb was visualised under a confocal microscope (Carl Zeiss, Jena, Germany).

ADCC and CDC:

Cells ($5 \times 10^3$) were co-incubated with 100 µl of PBMCs, 10% autologous serum or media alone or with mAbs at a range of concentrations. Spontaneous and maximum releases were evaluated by incubating the labeled cells with medium alone or with 10% Triton X-100, respectively. After 4 hr of incubation, 50 µl of supernatant from each well was transferred to 96 well lumaplates. Plates were allow to dry overnight and counted on a Topcount NXT counter (Perkin Elmer, Cambridge, UK). The mean percentage lysis of target cells was calculated according to the following formula:

$$\text{Mean \% lysis} = 100 \times \frac{\text{mean experimental counts} - \text{mean spontaneous counts}}{\text{mean maximum counts} - \text{mean spontaneous counts}}$$

ADC Assay

ADC was evaluated by measuring the cytotoxicity of immune-complexed mAbs with a mouse Fab-ZAP secondary conjugate (Advanced Targeting Systems) (30). Cells were plated in triplicates overnight into 96-well plates (2,000 cells, 90 µl/well). After preincubation (30 minutes at room temperature) of a concentration range of FG129 or CH129 mAbs with 50 ng of the Fab-ZAP conjugate, 10 µl of conjugate or free mAb was added to the wells and incubated for 72 hours. Control wells, consisted of cells incubated without conjugate, incubated with secondary Fab-ZAP without primary mAb and incubated with a control mAb in the presence of Fab-ZAP. Cell viability was measured by $^3$H-thymidine incorporation during the final 24 hours. Results are expressed as a percentage of $^3$H-thymidine incorporation by cells incubated with conjugate compared with primary mAb only.

To further investigate if CH129 would make a promising ADC candidate in a clinical setting, the mab was chemically conjugated to different payload/linker constructs that were pre-clinically and clinically validated. Thus, three CH129 constructs were produced by ADC Biotechnology: one with the auristatin MMAE linked via a cleavable dipeptide valine-citruline linker and a para-aminobenzylalcohol (PABA) self-immolative spacer, one with the DM4 maytansinoid linked via the intermediately cleavable hindered disulphide linker SPDB and one with the DM1 maytansinoid linked through the non-cleavable SMCC linker. A matched set of control ADC constructs was also produced using the non-targeting mab Rituximab, to be used in relevant assay controls.

The cytotoxic effect of the CH129-ADC constructs was assessed by using the water-soluble tetrazolium salt WST-8 (Sigma) to measure the activity of hydrogenases which is directly proportional with the number of viable cells. Cells were plated in 96-well plates at a density of 2000 cells/90 µl/well in 10% FBS-RPMI with Penicillin-Streptomycin (Sigma) and incubated overnight at 37° C., 5% CO2. The ADC constructs were then added to the cells at different concentrations in a final volume of 10 µl/well and the plates were incubated at 37° C., 5% CO2 for 72 h with the antibody constructs. The WST-8 was then added (10 µl/well) and the plates were further incubated 37° C., 5% CO2 for 3 h. After the 3 h incubation, the plates were read at 450 nm by Tecan Infinite F50. Results are expressed as percentages of control wells, consisting of cells only without any antibody. Cytotoxicity was studied on two colorectal cell lines Colo205 and HCT-15 that express high cell surface densities of the targeted antigen sialyl-lewis-a.

Example 1

Generation and Initial Characterisation of FG129 mAbs

FG129 was produced by immunising Balb/c mice with plasma membrane lipid extracts from LS180 cells (colorectal cell line) incorporated into liposomes, at two-week intervals over a period of 2 months, alpha-galactosylceramide was used as an adjuvant in the first, third and fourth immunisation and anti-CD40 mAb used during the second immunisation.

Analysis of antibody response to immunisations: Antibody titres were initially monitored by lipid enzyme-linked immunosorbent assay (ELISA). Flow cytometry analysis (FACS) was also carried out using LS 180 tumour cells and Western blot using LS180. The mouse considered to have the best response, compared to the pre-bleed serum control, was boosted intravenously (i.v.) with LS180 plasma membrane lipid extract prior to fusion. 8 days after fusion, supernatants were collected and screened against fresh L S 1 8 0 tumour cells by flow cytometry. Hybridomas which demonstrated cell surface binding, using an indirect immunofluorescence assay, were harvested, washed in complete media and spread across 96 well plates at 0.3 cells per well to acquire a clone. The plate was then screened for positive wells and these grown on until a sufficient number of cells was obtained to spread across a 96 well plate at 0.3 cells per well for a second time. If the resulting number of colonies equalled ~30 and all hybridomas were positive, the hybridoma was considered a clone. Methods for clonal expansion, bulk culture and antibody purification of antibodies or antibody fragments are available using conventional techniques known to those skilled in the art.

Example 2

Chimerisation of FG129

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody. Chimeric (or humanised) antibodies of the present invention can be prepared based on the sequence of a murine mAb prepared as described above. The amino acid and nucleotide sequence for the variable and constant regions of the heavy (FIG. 1a) and light chains (FIG. 1b) of the FG129 mAb are shown in FIG. 1. Numbers refer to the standardised IMGT system for the numbering of antibody sequences [49]. The CDR1, CDR 2 and CDR 3 regions are indicated. The FG129 heavy chain belongs to the mouse heavy chain family IGHV10-1*02 (IGHD1-1*01, IGHJ4*01), with three mutations compared to the parental germline gene. The FG129 light chain belongs to the mouse kappa chain family IGKV8-19*01 (IGKJ4*01), with two mutations compared to the parental germline gene.

FG129 heavy and light chain variable regions were cloned into a human IgG1 expression vector. This was transfected into CHO-S or HEK293 cells and human antibody purified on protein G. The chimeric mAbs CH129 bound to the colorectal cell line, Colo205. The amino acid and nucleotide sequence for the heavy and light chains of the human ch129 mAb are shown in FIGS. 2a and 2b respectively.

Example 3

Defining the Epitopes Recognised by FG129 and CH129 mAbs

MAb FG129 is a mouse IgG1k isotype that was generated by immunising Balb/c mice with glycolipid extracts from colorectal cell line LS180. Glycan profiling analysis done by CFG on ≥600 natural and synthetic glycans shows a high specificity of FG129 binding sialyl-di-Lewis$^a$ (100%) and sialyl-Lewis$^{a-x}$ (89%). It can also bind to mono-sialyl-Lewis$^a$ (89%), but only if presented on a long carrier (sp8) and not on a short carrier (sp0), suggesting that it requires at least 4 carbohydrates or sufficient space to allow the three carbohydrate residues to insert into the antibody sequence presented in the correct conformation to bind (FIG. 3a).

Figure 3B:
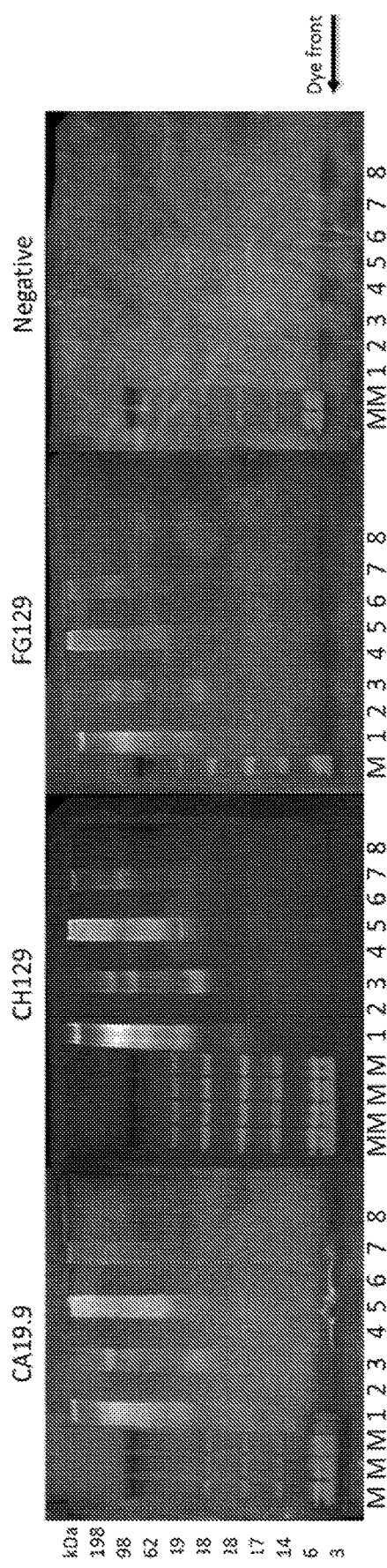
FIG. 3b: Indirect Western blot analysis of the antigens recognised by mAb FG129 and mAb ch 129 (1 µg/ml). Lane M: molecular marker (in red); Lane 1: Colo205 cell lysates ($1 \times 10^5$ cells); Lane 2: Colo205 TGL ($1 \times 10^6$ cells); Lane 3: HCT-15 cell lysates ($1 \times 10^5$ cells); Lane 4: HCT-15 TGL ($1 \times 10^6$ cells); Lane 5: BxPc3 cell lysates ($1 \times 10^5$ cells); Lane 6: BxPc3 TGL ($1 \times 10^6$ cells); Lane 7: LS180 cell lysates ($1 \times 10^5$ cells); Lane 8: LS180 TGL ($1 \times 10^6$ cells). Negative control consisted of omission of primary antibody. CA19.9 was used as positive control recognising sialyl-Lewis$^a$ on glycolipids as well as glycoproteins.

To analyse if these glycans' were expressed on glycoproteins or glycolipids from tumour cell lines FG129 binding was assessed by Western blotting (FIG. 3b). Tumour lysates or tumour glycolipid extracts from colorectal (Colo205 HCT-15 and LS180) and pancreatic cells lines (BxPc3), were blotted with FG129, CH129 mAb, secondary antibody alone or CA19.9 (anti-sialyl lewis a Mab). FG129 and CH129 bound to a wide range of glycoproteins in Colo205 and HCT-15 lysate and to a smaller number of glycoproteins in BxPc3 and LS180 lystates. FG129 failed to bind to any of the tumour glycolipid extracts. In contrast, CA19.9 showed binding to a wider range of glycoproteins in BxPc3, Colo205 and LS180 and to glycolipids from BxPc3 and HCT-15 cells. These results suggest that FG129 prefers to bind to six carbohydrate residues and prefers sialyl-di-Lewis$^a$ which is predominantly expressed on proteins. In contrast, CA19.9 which prefers the 3 carbohydrate residue glycan, sialyl-Lewis$^a$, binds to both lipids and proteins.

As mAbs require strong affinity to localise within tumours the affinity of FG129 mAb was assessed by Biacore and ELISA. Affinity measurements using SPR (Biacore X or 3000) on a sialyl-Lewis$^a$ (as sialyl-di-Lewis$^a$ is unavailable) coupled chip revealed two possible functional affinities—a dominant one ($K_d$~$10^{-7}$M) accounting for 80% of the population and another very high affinity ($K_d$~$10^{-13}$M) with fast association (~$10^4$ 1/Ms) and very slow dissociation rate ($K_d$-$10^{-8}$ 1/s) (Table 1a). In particular, the affinity measurements revealed subnanomolar functional affinity for FG129 and nanomolar affinity for CH129, both showing relatively fast on-rates and slow off-rates for sialyl-Lewis-a binding (Table 1b). The monovalent binding affinity of the scFv129 was lower ($10^{-7}$M), with a slower on-rate but similar off-rate, suggesting bivalent binding on the chip by FG129 and CH129.

TABLE 1a

Determination of kinetic sialyl-Lewis$^a$ binding parameters by SPR

| Equilibrium dissociation constant $K_d$ (M) | Association rate $k_a$ (1/Ms) | Dissociation rate $k_d$ (1/s) |
|---|---|---|
| Major $K_{d1}$ (80%)~1.3 × $10^{-7}$ | $k_{a1}$~1.97 × $10^4$ | $k_{d1}$~2.57 × $10^{-3}$ |
| Minor $K_{d2}$ (20%)~1.4 × $10^{-13}$ | $k_{a2}$~8.85 × $10^4$ | $k_{d2}$~1.35 × $10^{-8}$ |

TABLE 1b

Determination of kinetic sialyl-Lewis-a binding parameters by SPR

| | SPR Real-time sialyl Le$^a$-HSA binding | | |
|---|---|---|---|
| mAb | Association Rate $k_{on}$ (1/Ms) | Dissociation Rate $k_{off}$ (1/s) | Dissociation Constant Kd (M) |
| FG129 | 6.2 × $10^5$ | 1.1 × $10^{-4}$ | 0.2 × $10^{-9}$ |
| CH129 | 1.3 × $10^5$ | 2.6 × $10^{-4}$ | 2.1 × $10^{-9}$ |
| FG129-scFv | 3.0 × $10^3$ | 5.0 × $10^{-4}$ | 1.7 × $10^{-7}$ |

Figure 4:
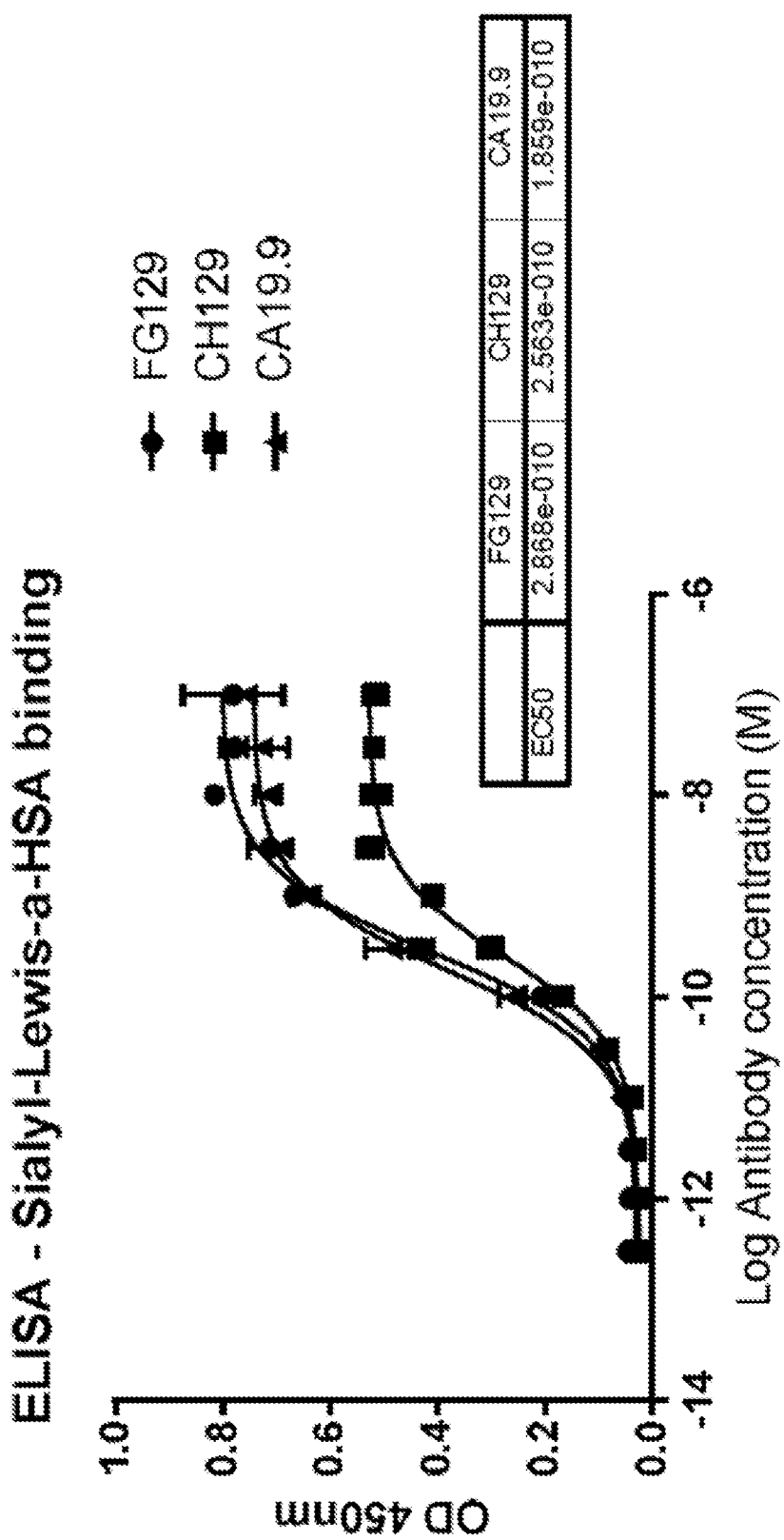
FIG. 4: ELISA analysis of FG129 and CH129 binding to sialyl-Lewis$^a$-HSA. CA19.9 was used as positive control recognising sialyl-Lewis$^a$ on glycolipids as well as glycoproteins. Negative controls consisted of an isotype antibody that does not recognise sialyl-Lewis$^a$, HSA coated wells, uncoated wells where the antigen was omitted, and wells where FG129 was omitted. Error bars represent the mean±SD of duplicate wells.

Additionally, antigen binding was assessed by ELISA using sialyl-Lewis$^a$-HSA which revealed a FG129 and CH129 dose dependent response, confirmed specific sialyl-Lewis$^a$ binding with a subnanomolar Ec$_{50}$ (~$10^{-10}$M) and also showed no binding to HSA and plastic (FIG. 4).

Example 4

Immunohistochemistry Assessment of FG129 and CH129 mAbs.

To determine the therapeutic value of FG129, it was screened on colorectal, gastric, pancreatic, lung, and ovarian tumour tissue microarrays (TMAs) by immunohistochemistry (IHC).

The tumour tissue binding of FG129 was assessed by IHC on tumour TMAs. The mAb bound to 74% (135/182) of pancreatic tumours, 50% (46/92) of gastric tumours, 36% (100/281) of colorectal tumours, 27% (89/327) of ovarian and 21% (42/201) of NSCLC tumours (Table 1).

TABLE 2

Binding of FG129 (1 µg/ml) by IHC to gastric, colorectal, pancreatic, ovarian and lung TMAs by staining intensity

| Staining | Gastric | | Colorectal | | Pancreatic + biliary/ ampullary | | Ovarian | | Lung (adeno- carcinoma) | |
|---|---|---|---|---|---|---|---|---|---|---|
| | Number | % | Number | % | Number | % | Number | % | Number | % |
| Negative | 46 | 50 | 181 | 64 | 45 | 25 | 238 | 73 | 159 | 79 |
| Weak | 25 | 27 | 72 | 26 | 37 | 21 | 63 | 19 | 21 | 10 |
| Moderate | 10 | 11 | 25 | 9 | 61 | 34 | 21 | 6 | 9 | 4 |
| Strong | 11 | 12 | 3 | 1 | 37 | 21 | 5 | 2 | 12 | 6 |

Figure 5A:
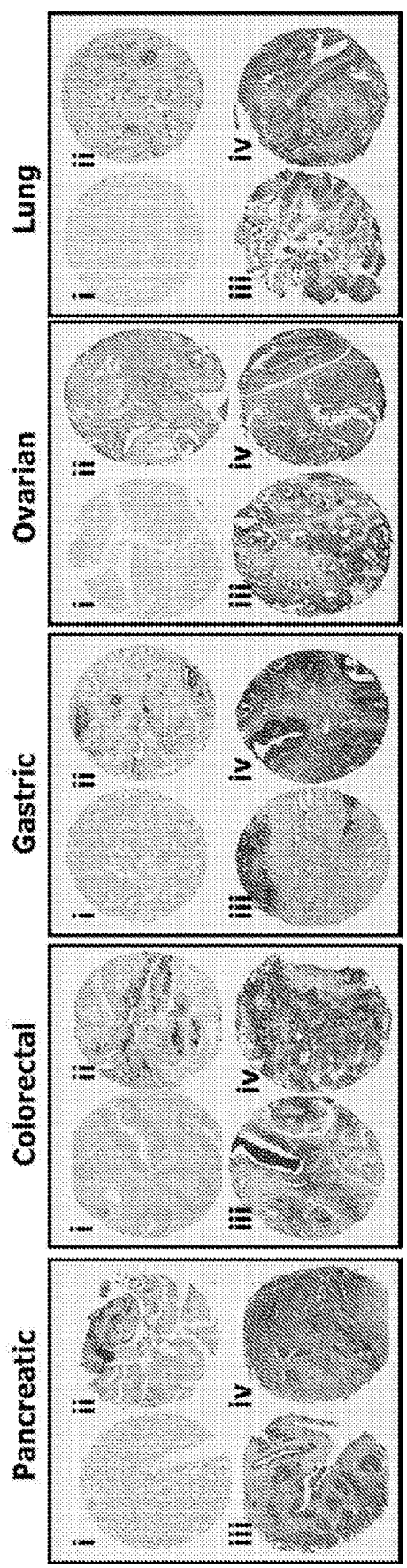
FIG. 5a: Binding of FG129 (1 µg/ml) by IHC to colorectal, pancreatic, gastric, ovarian and lung TMAs. Representative images of different staining levels are shown i) negative, ii) weak, iii) moderate and iv) strong (magnification ×20).
Figure 5B:
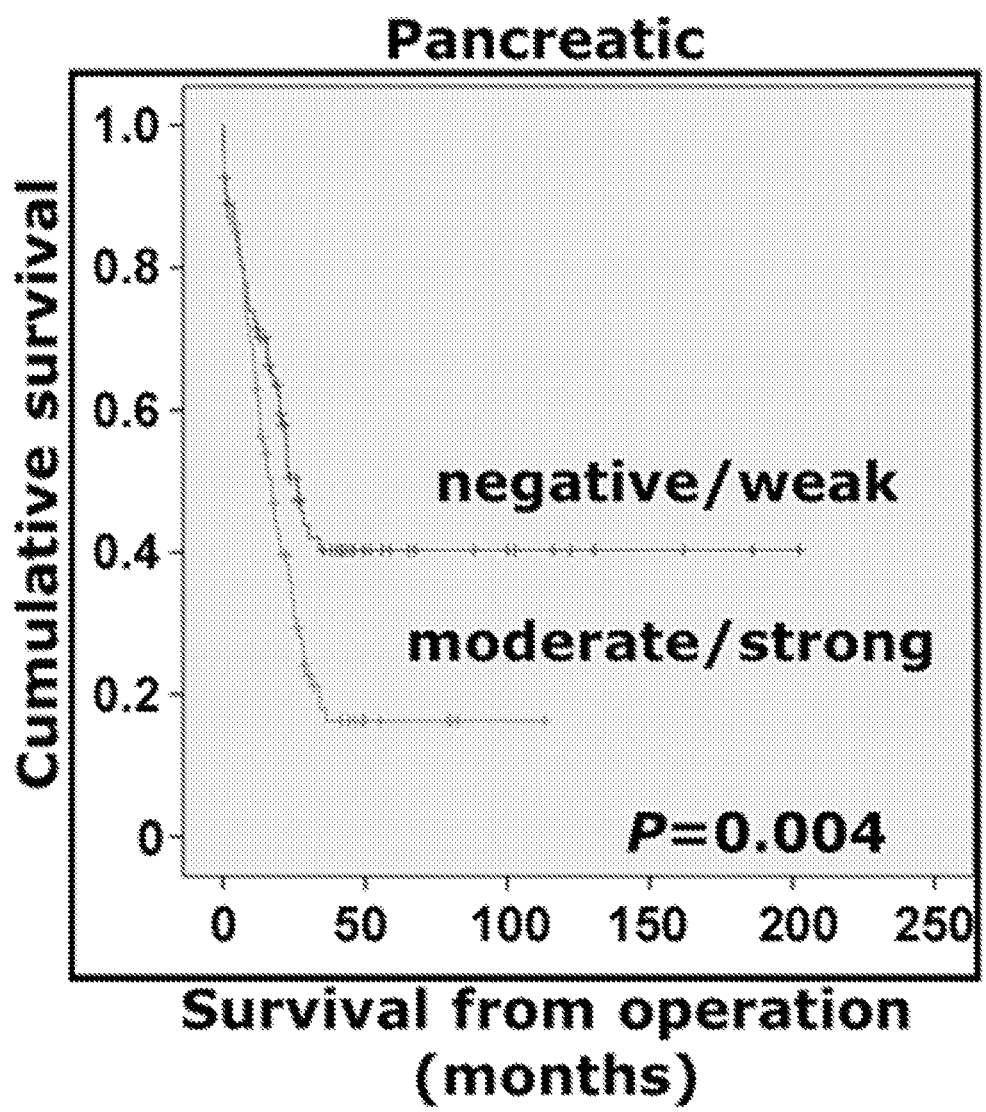
FIG. 5b: Kaplan-Meier analysis of disease-free survival of pancreatic patients staining with FG129 mAb. Cut-off for high versus low was determined by X-tile.

Representatives of different staining levels of tumour tissues with FG129 are shown in FIG. 5a. In pancreatic cancer cohort, Kaplan-Meier analysis of disease-free survival of pancreatic patients revealed a significantly lower mean survival time in the high FG129 binding group (mean survival: 30 months (n=94)) compared to the lower FG129 binding group (mean survival: 90 months (n=82)), p=0.004, Log-Rank test. On multivariate analysis using Cox regression, high FG129 antigen expression in pancreatic cancer was a marker for poor prognosis which was independent of perineural invasion (p=0.00$^3$) (FIG. 5b).

Figure 5C:
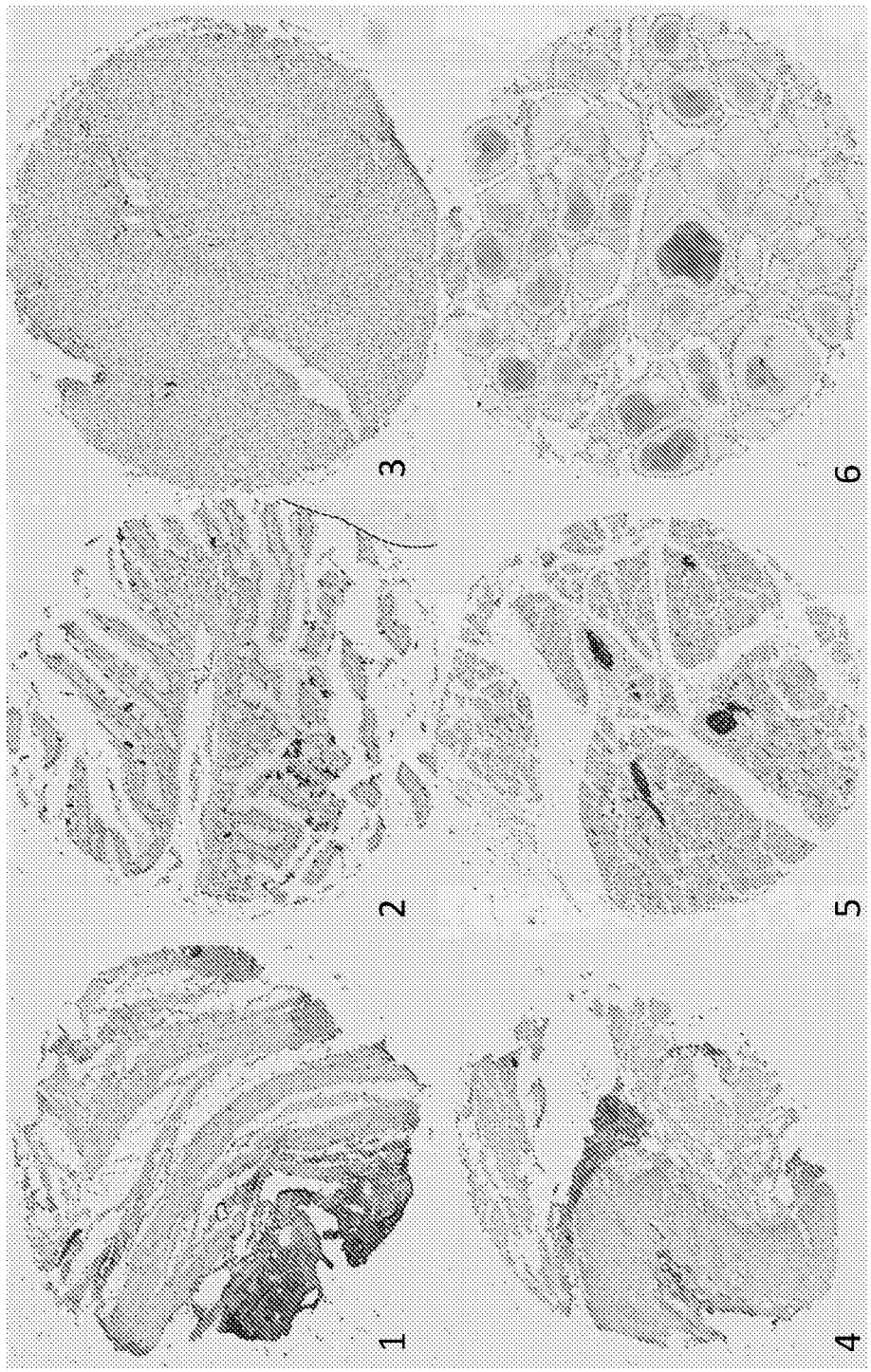
FIG. 5c: Normal human tissue (AMSBIO) binding of FG129, showing very limited binding in 1) Gallbladder; 2) Ileum; 3) Liver; 4) Oesophagus; 5) Pancreas; 6)Thyroid (magnification ×20).

In normal tissue, FG129 had a very restricted binding pattern and did not bind most normal tissues like heart, brain, stomach, and kidney (table 1). Very limited binding was seen in gallbladder (weak), ileum (1%), liver (1%), oesophagus (5%), pancreas (10%), and thyroid (weak: FIG. 5c). This is in direct contrast to CA19.9 mAb which recognizes sialyl Lewis$^a$ on both lipids and proteins. It binds strongly (3+) to oesophagus, gallbladder and liver, moderately (2+) to breast and weakly (1+) to rectum. FG129 displays strong tumour tissue binding with low normal tissue reactivity, and is associated with poor prognosis in pancreatic cancer patients.

TABLE 3

Summary of FG129 and CA19.9 binding to a panel of normal tissues using paraffin-fixed sections. Intensity of staining is shown as 0, 1, 2 or 3, relating to negative, weak, moderate or strong binding.

| Tissue Type | FG129 | CA19.9 |
|---|---|---|
| Oesophagus | 0 | 3 |
| Oesophagus | 1 | 3 |
| Rectum | 0 | 1 |
| Rectum | 0 | 1 |
| Gallbladder | 1 | 3 |
| Gallbladder | 1 | 1 |
| Skin | 0 | 0 |
| Skin | 0 | 0 |
| Adipose | 0 | 0 |
| Adipose | 0 | 0 |
| Heart | 0 | 0 |
| Heart | 0 | 0 |
| Skeletal | 0 | 0 |
| Skeletal | 0 | 0 |
| Bladder | 0 | 0 |
| Bladder | 0 | 0 |
| Ileum | 1 | 0 |
| Ileum | 1 | 0 |
| Spleen | 0 | 0 |
| Spleen | 0 | 0 |
| Brain | 0 | 0 |
| Brain | 0 | 0 |
| Jejunum | 0 | 0 |
| Jejunum | 0 | 0 |
| Stomach | 0 | 0 |
| Stomach | 0 | 0 |
| Breast | 0 | 2 |
| Breast | 0 | 2 |
| Kidney | 0 | 0 |
| Kidney | 0 | 0 |
| Testis | 0 | 0 |
| Testis | 0 | 0 |
| Cerebellum | 0 | 0 |
| Cerebellum | 0 | 0 |
| Liver | 3% at 1 | 3 |
| Liver | 3% at 1 | 3 |
| Thymus | 0 | 1 |
| Thymus | 0 | 2 |
| Cervix | 0 | 0 |
| Cervix | 0 | 0 |
| Lung | 0 | 0 |
| Lung | 0 | 0 |
| Smooth Muscle | 0 | 0 |
| Smooth Muscle | 0 | 0 |
| Colon | 0 | 2 |
| Colon | 0 | 1 |
| Ovary | 0 | 0 |
| Ovary | 0 | 0 |
| Tonsil | 0 | 1 |
| Tonsil | 0 | 0 |
| Diaphragm | 0 | 0 |

TABLE 3-continued

Summary of FG129 and CA19.9 binding to a panel of normal tissues using paraffin-fixed sections. Intensity of staining is shown as 0, 1, 2 or 3, relating to negative, weak, moderate or strong binding.

| Tissue Type | FG129 | CA19.9 |
|---|---|---|
| Diaphragm | 0 | 0 |
| Pancreas | 1 | 3 |
| Pancreas | 1 | 2 |
| Uterus | 0 | 0 |
| Uterus | 0 | 0 |
| Duodenum | 0 | 0 |
| Duodenum | 0 | 0 |
| Thyroid | 1 | 0 |
| Thyroid | 1 | 0 |

In normal tissue, CH129 had a very restricted binding pattern and did not bind most normal tissues like heart, brain, stomach, and kidney (table 1). Very limited binding was seen in gallbladder (weak), ileum (1%), liver (1%), oesophagus (5%), pancreas (10%), and thyroid (weak: FIG. 5a).

Example 5

FG129 and CH129 mAbs Binding Studies

Figure 6A:
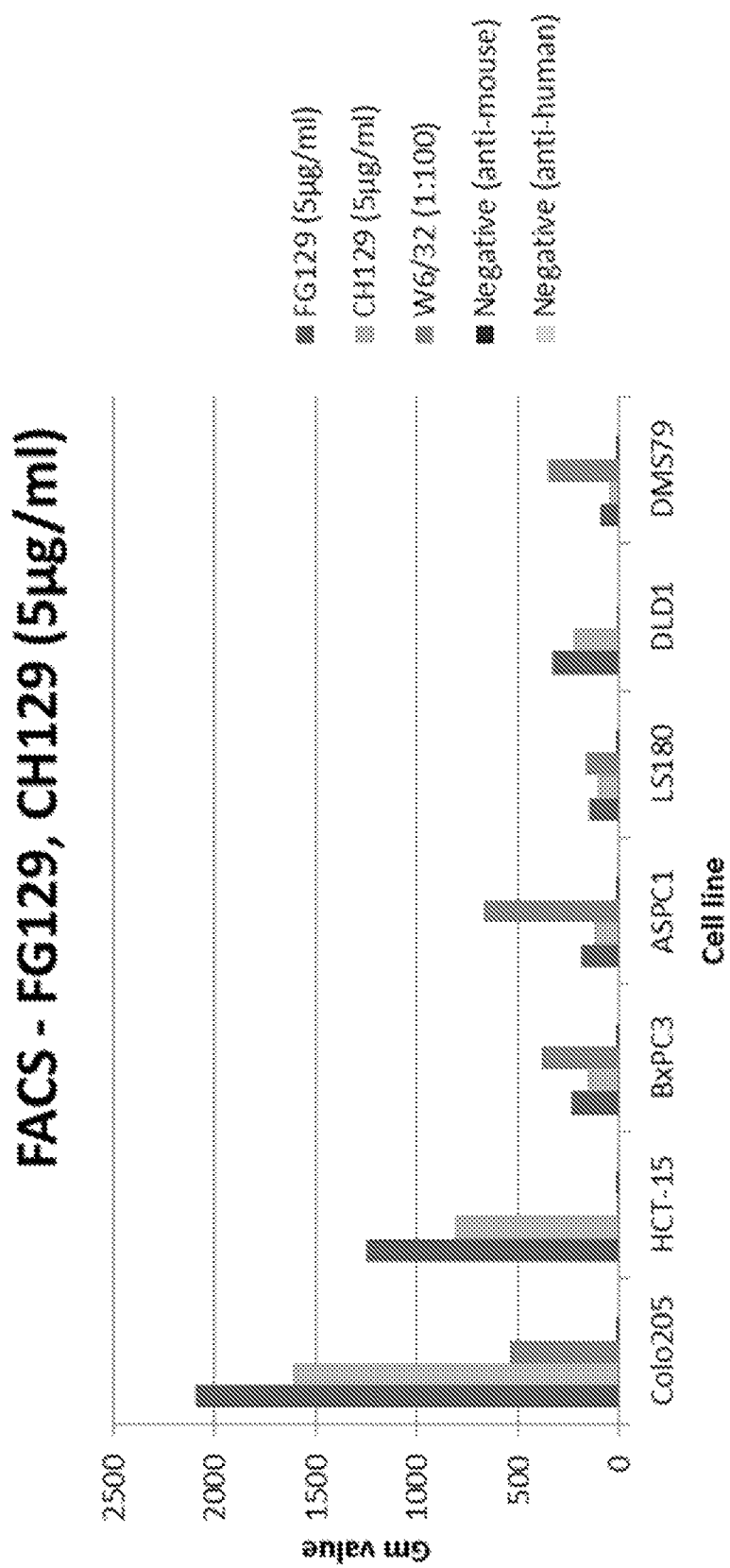
FIG. 6a: Indirect immunofluorescence staining and flow cytometric analysis of FG129 and CH129 (5 g/ml) mAb binding to the cell surface of tumour cell lines.
Figure 6B:
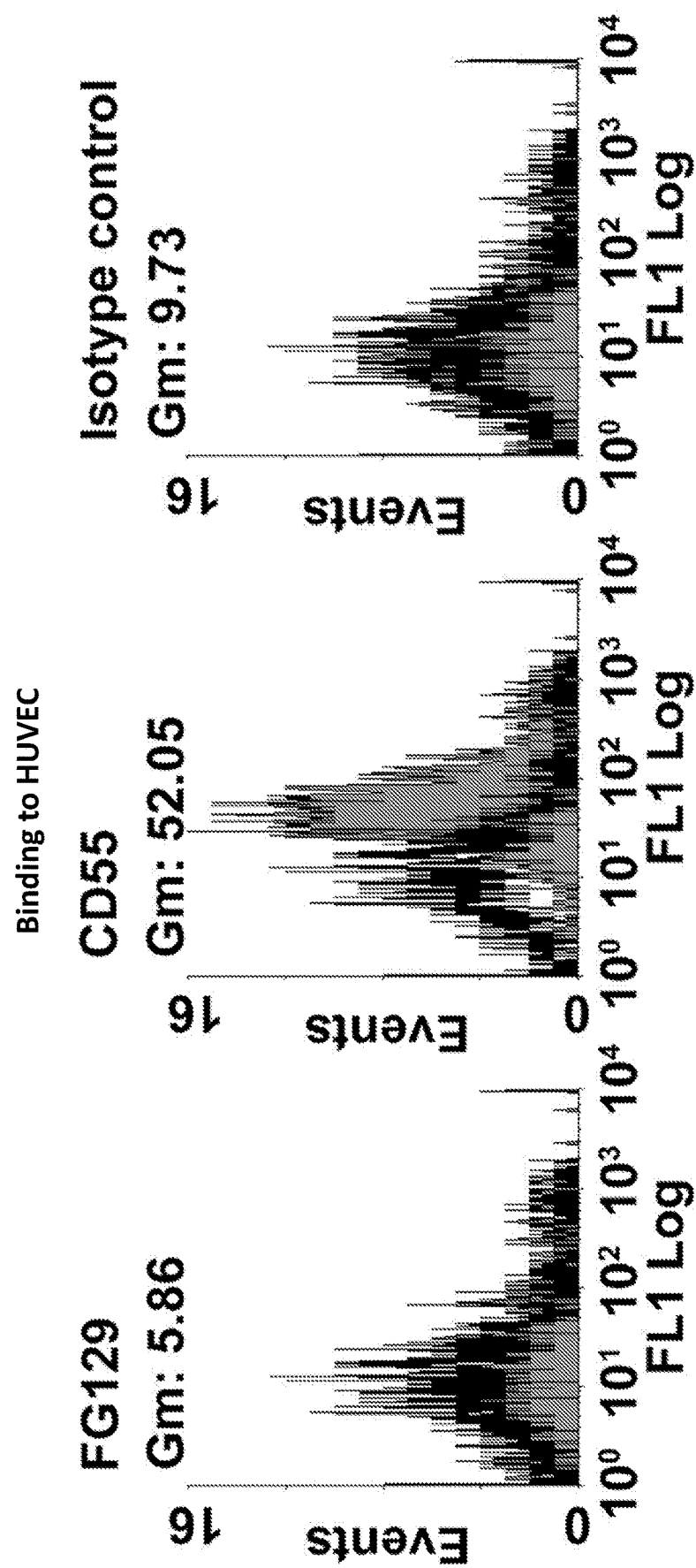
FIG. 6b: Indirect immunofluorescence staining and flow cytometric analysis of FG129 (5 µg/ml) mAb binding to the cell surface of HUVEC normal umbilical cells. An anti-CD55 mAb was used as a positive control and an anti-IgG isotype antibody as a negative control.
Figure 6C:
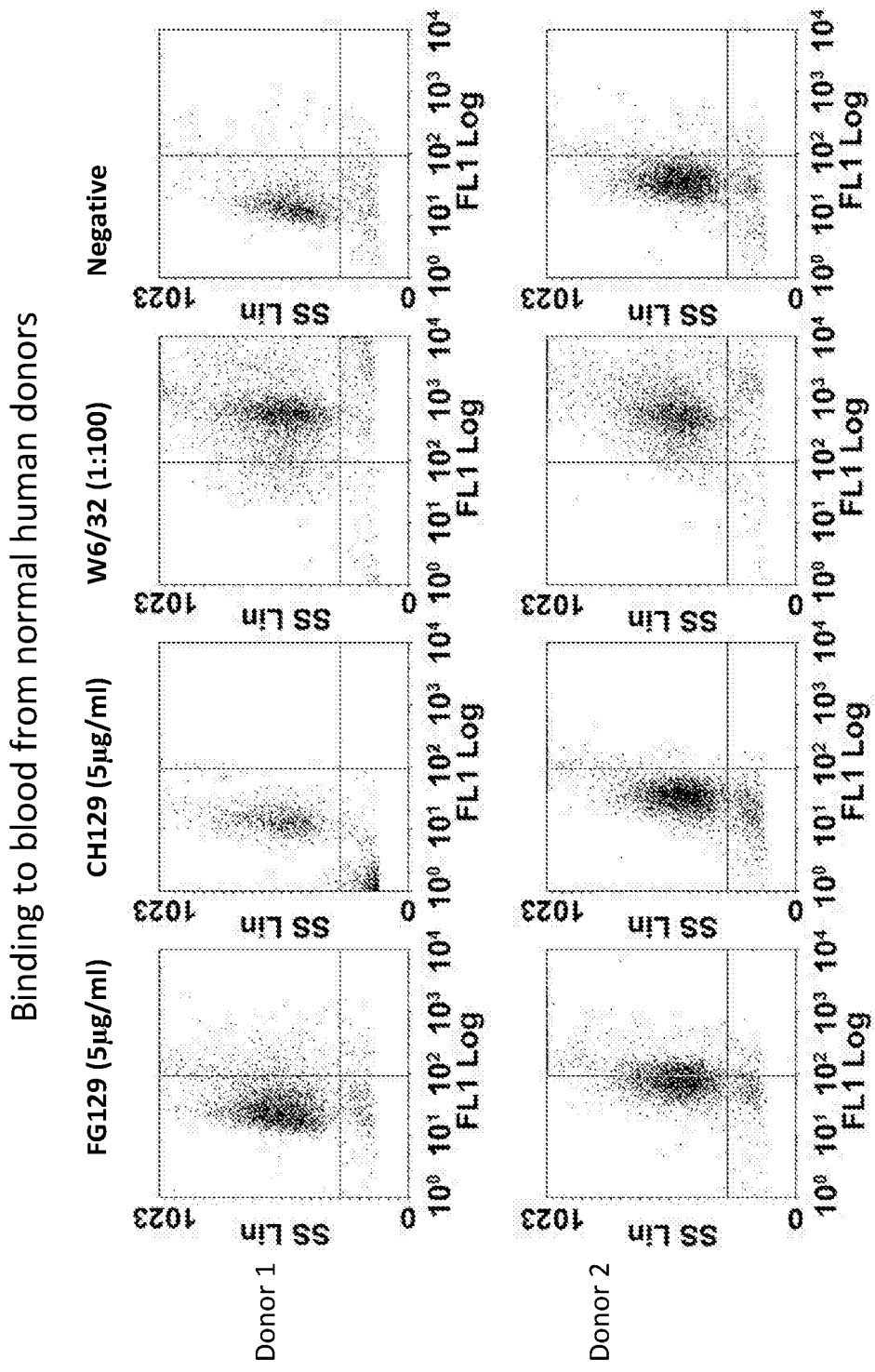
FIG. 6c: Indirect immunofluorescence staining and flow cytometric analysis of FG129 and ch129 (5 g/ml) mAbs binding to whole blood. An anti-HLA mAb w6/32 was used as a positive control and an anti-IgG isotype antibody as a negative control.

To determine if any cell line is a good model for tumours expressing sialyl-di-Lewis$^a$ a range of cell lines and normal cells were screened for cell surface binding of FG129. FG129 and CH129 showed strong binding (geometric mean (Gm)≥1000) to tumour cell lines HCT-15, Colo205, moderate binding (Gm ~100) to BxPc3, ASPC1, LS180, DLD1, and DMS79 and no binding to AGS, SW480, EKVX, MCF-7, LoVo, DU4475, OVCAR3, OVCAR4 and OVCA433. This suggests that HCT-15, Colo205, ASPC1, BxPc3, LS180, DLD1, and DMS79 would be good models for assessing the sensitivity of tumour cells with different cell densities of sialyl-Lewis$^a$ to FG129 therapy (FIG. 6a). FG129 failed to bind to normal HUVEC cells (FIG. 6b). For comparison, an anti-CD55 mAb was used as a positive control and an anti-IgG isotype antibody as a negative control. Importantly, FG129 and CH129 did not bind to PBMCs from a range of healthy donors (FIG. 6c). These results identified several cell lines as models of human tumours for in vitro studies and showed that FG129 did not bind to normal blood or endothelial cells suggesting that they would not prevent FG129 localising within tumours.

The antigen density (SABC) was calculated to be 985,813 and 1,570,563 for HCT-15 and COLO205, respectively. Moderately binding cells included BxPc3 and LS180 (SABC: 300,036 and 469,272 respectively).

Figure 7:
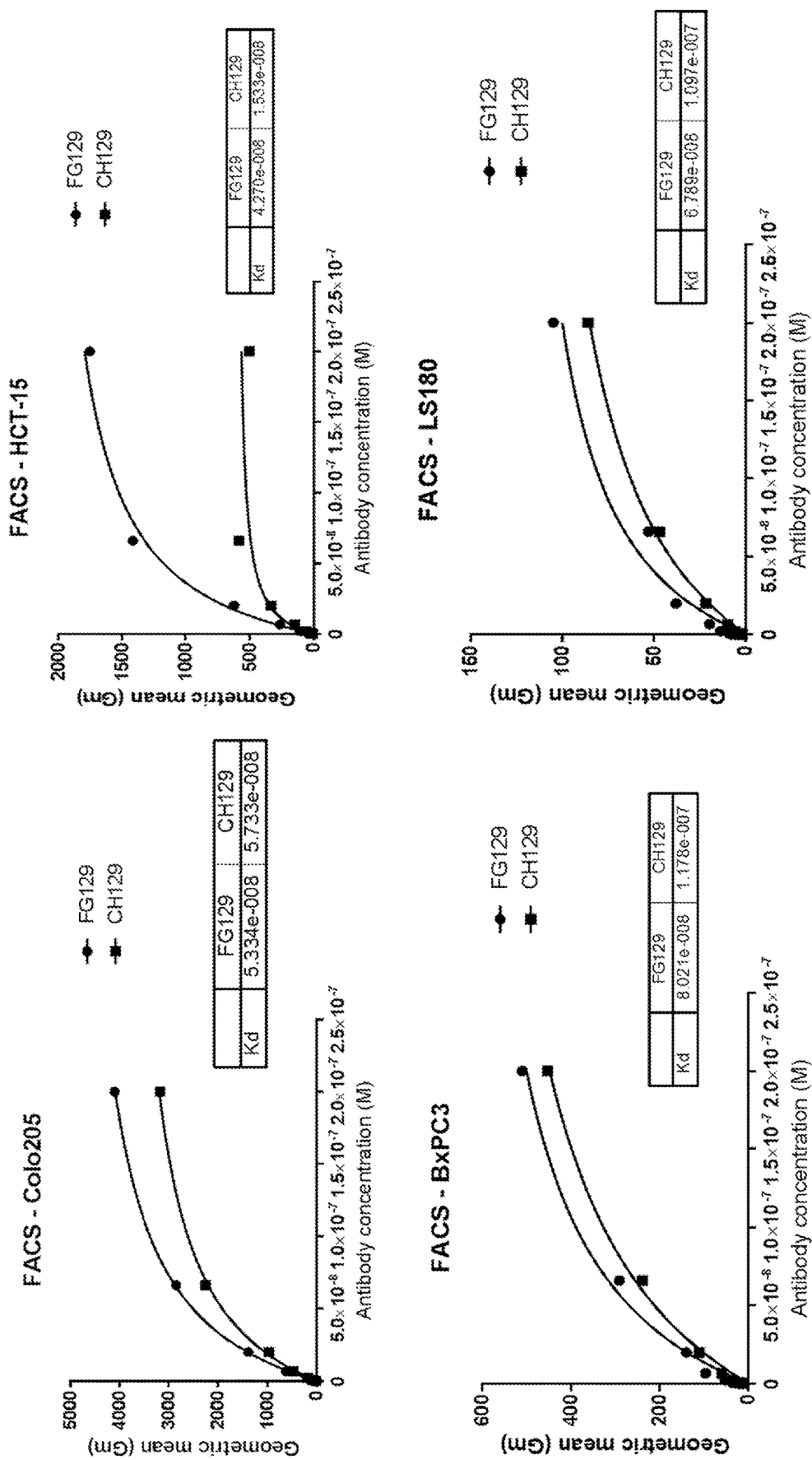
FIG. 7: Indirect immunofluorescence staining and flow cytometric analysis of titrations of FG129 mAb and CH129 mAb binding to the cell surface of Colo205 (7a), HCT-15 (7b), BxPc3 (7c) and LS180 (7d) cells.

To estimate the affinity of binding to tumour cell lines, varying concentration of FG129 and CH129 mAbs were added to Colo205, HCT-15, BxPC3 and LS180 and binding was detected by indirect immunofluorescence analysis and flow cytometric analysis (FIG. 7). Both FG129 and CH129 bound to the high expressing cell lines with Kd of 6-20 nM and to low expressing cell lines with a Kd of 30-50 nM. This is higher than binding to sialyl lewis$^a$-HSA and probably reflects the complexity of glycan expression on the cell surface.

The antigen density (SABC) was calculated to be 985,813 and 1,570,563 for HCT-15 and COLO205, respectively. Moderately binding cells included BxPc3 and LS180 (SABC: 300,036 and 469,272 respectively).

Example 6

In Vitro Anti-Tumour Activity of FG129 and CH129

Figure 8:
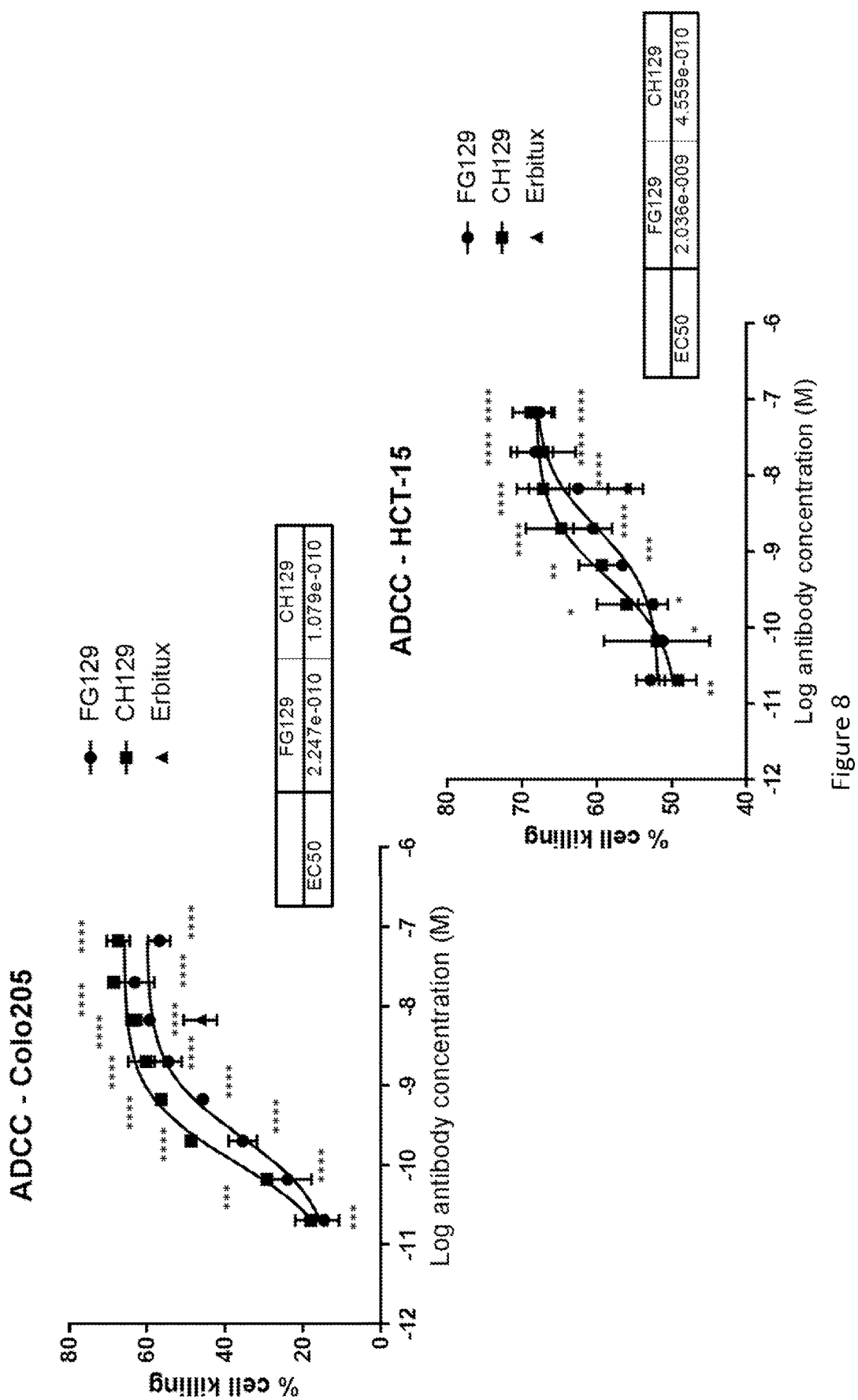
FIG. 8: ADCC killing of Colo205 (8a) and HCT-15 (8b) by FG129 and CH129. Erbitux was used as positive control, while PBMCs and cells alone were used as negative controls. Anova test performed using GraphPad Prism6 shows the significant difference between each concentration and the negative control consisting of cells with PBMCs only.
Figure 9:
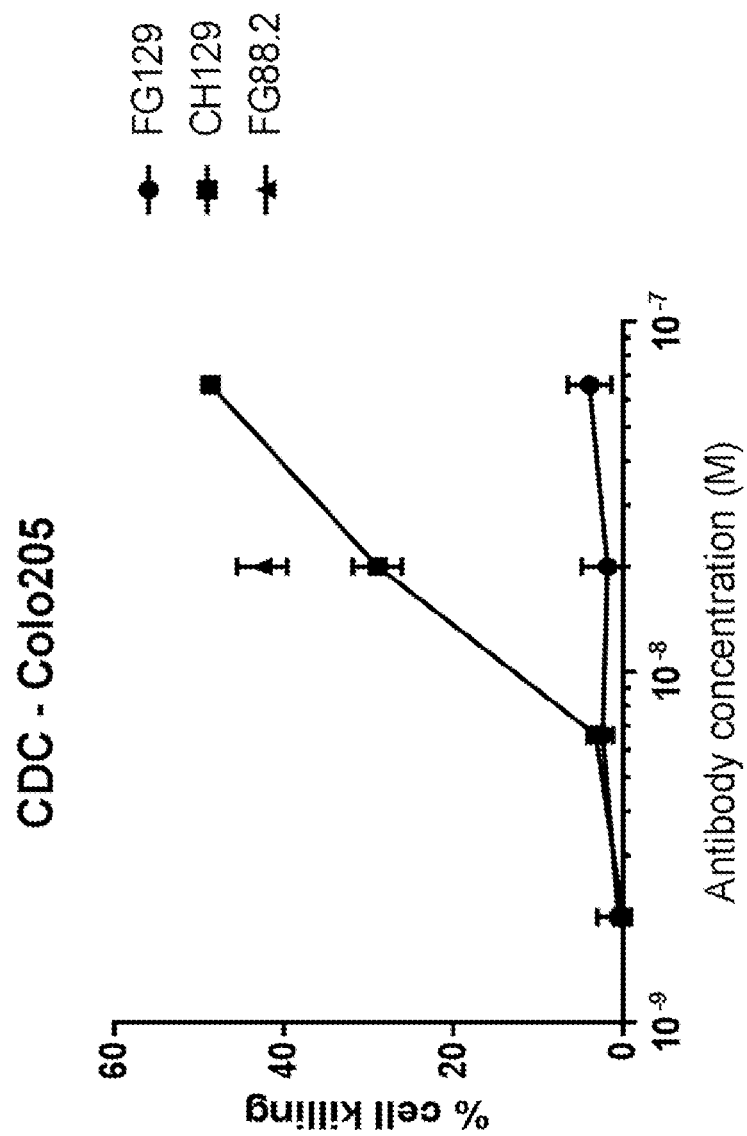
FIG. 9: CDC killing of Colo205 by FG129 and CH129. Erbitux was used as positive control, while PBMCs and cells alone were used as negative controls. Anova test performed using GraphPad Prism6 shows the significant difference between each concentration and the negative control consisting of cells with PBMCs only.

The ability of FG129 and CH129 to induce Colo205 and HCT-15 tumor cell death in the presence of human PBMCs through ADCC was investigated. Both the mouse FG129 and chimeric CH129 mAb induced potent cell lysis of both cell lines in a concentration-dependent manner. CH129 had 2-4 increase in killing when compared to the mouse mAb with an $EC_{50}$ value of ~$10^{-10}$M (FIG. 8). The ability of FG129 and CH129 to induce Colo205, tumor cell death in the presence of complement through CDC was investigated. Chimeric but not mouse mabs showed good CDC (FIG. 9).

Example 7

Internalisation and ADC (Antibody Dependent Drug Cytotoxicity)

Figure 10A:
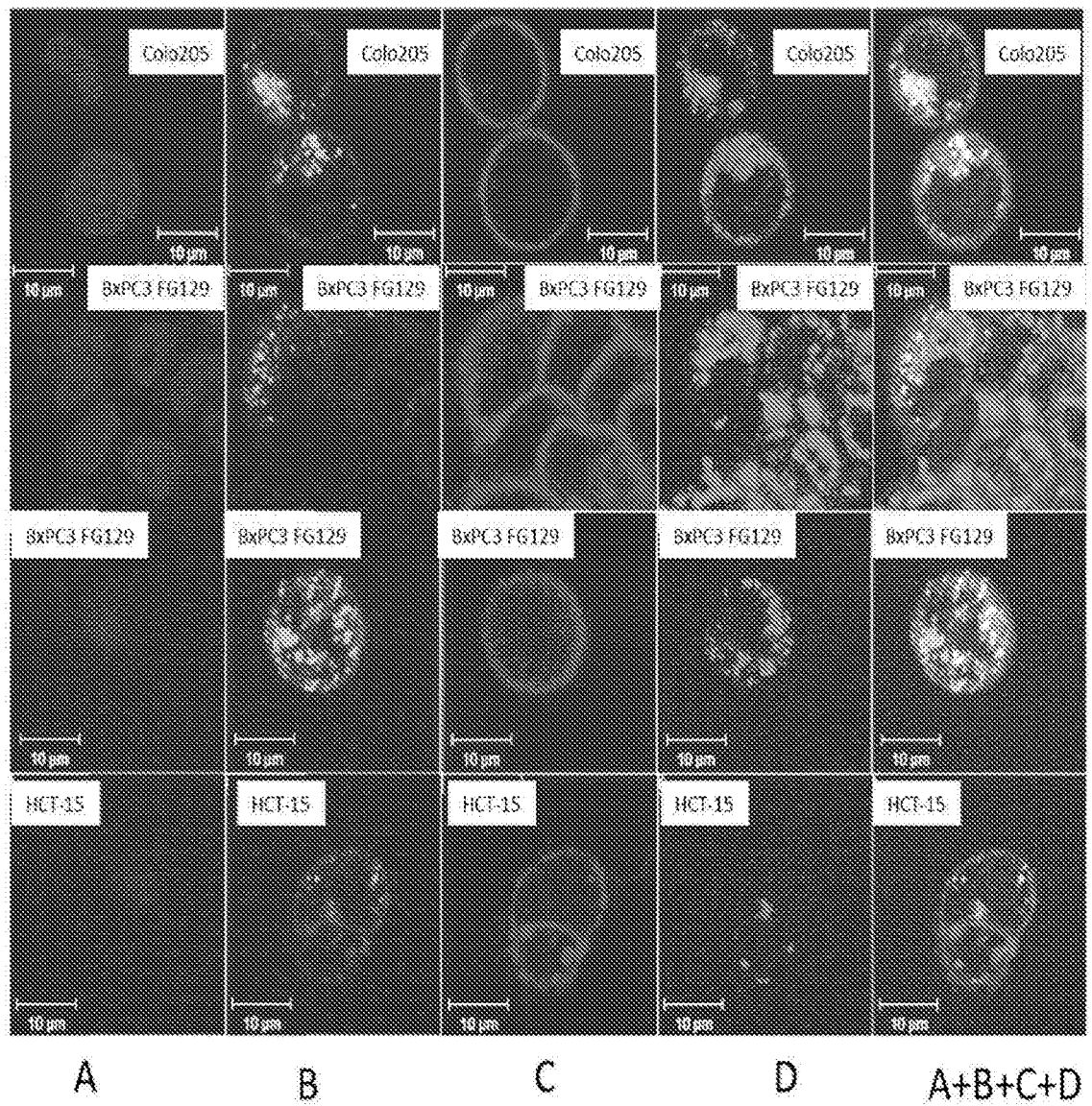
FIG. 10: Z-stack confocal microscopy of Alexa Fluor® 488 (green) labelled FG129 (panel 10a) and CH129 (panel 10b) internalising in live Colo205, BxPC3 and HCT-15 showing co-localisation with lysosomes. The plasma membrane was labelled with CellMask™ Orange (red/C), the lysosomes with LysoTracker® Deep Red (purple/D) and the nucleus with Hoechst 33258 (blue/A) (magnification ×60).
Figure 10B:
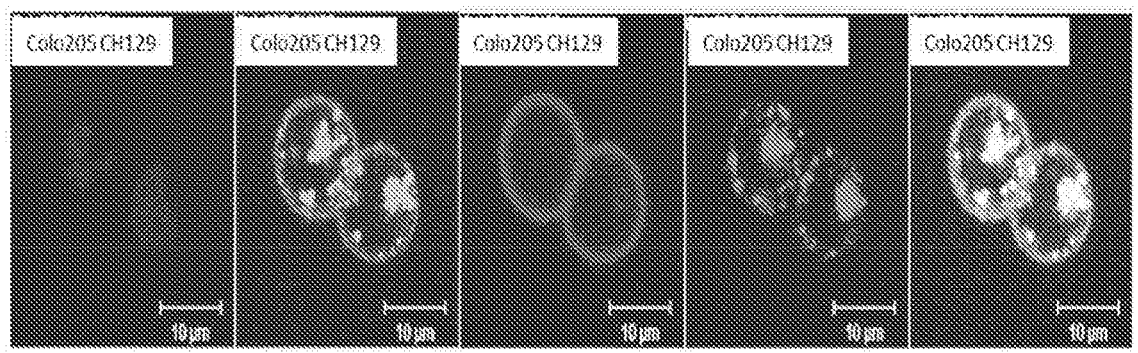

To further determine the therapeutic ability of the FG129 and CH129 the mAbs were screened for their ability to act as a drug carrier by internalising and delivering drug to lysosomes. Cellular internalisation was assessed by confocal microscopy, which showed internalisation of both 129 mAbs over a period of 90 minutes and co-localisation within the lysosomes. The nucleus was stained in blue, plasma membrane in red, lysosomal compartments in purple and the 129 antibodies in green. Internalisation is seen on high cell surface antigen density colorectal cell lines Colo205 and HCT-15 and on pancreatic cell line BxPC3 (FIGS. 10a and b).

Figures 11A, 11B:
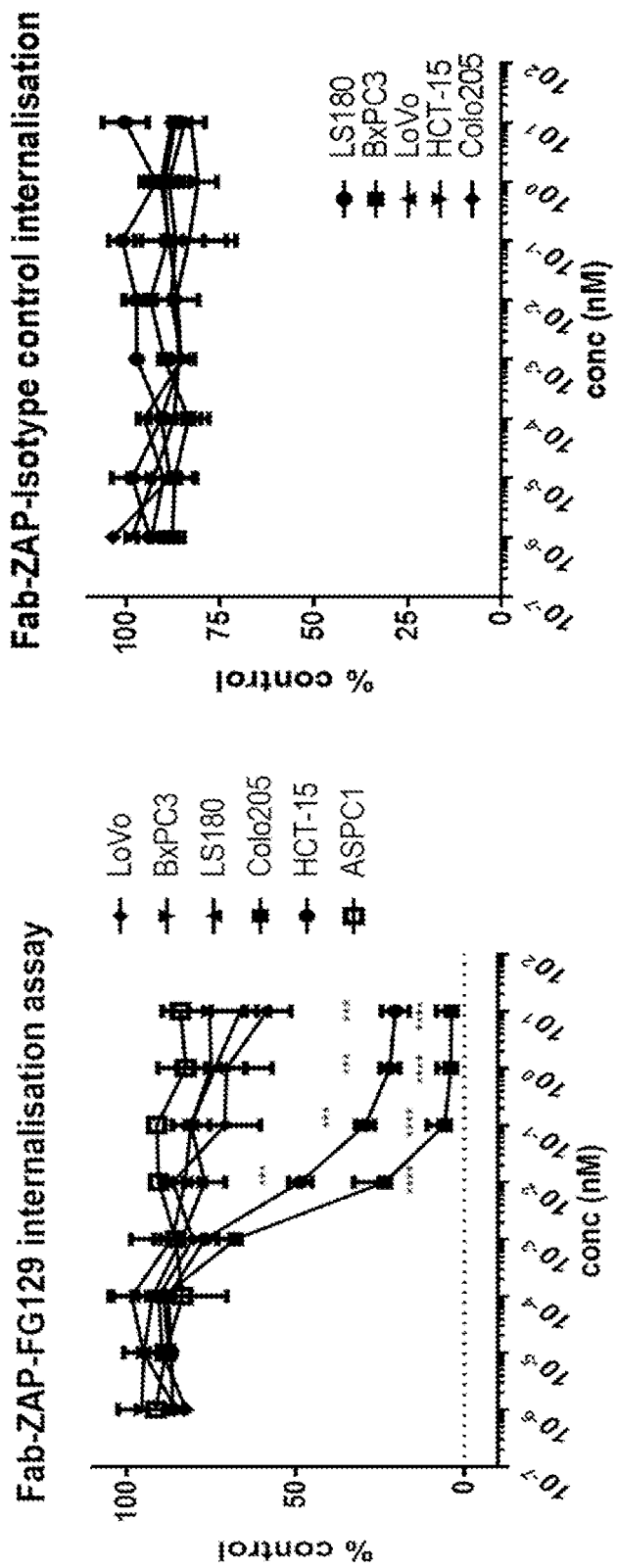
FIG. 11a: Cytotoxicity of Fab-ZAP-FG129 in antigen positive (HCT15, Colo205, BxPC3, ASPC1) and negative (LoVo, LS180) cancer cell lines. The cytotoxicity of internalised FG129 pre-incubated with saporin-linked anti-mouse IgG Fab fragment was evaluated using $^3$H-thymidine incorporation. Results are presented as percentage of proliferation of cells treated with the primary mAb only. Error bars show the mean±SD from four independent experiments.
FIG. 11b: Fab-ZAP-IgG Isotype internalisation assay. Results are presented normalised, as percentage of proliferation of cells treated with the primary mAb only. Error bars show the mean±SD from three independent experiments.
Figures 11C, 11D:
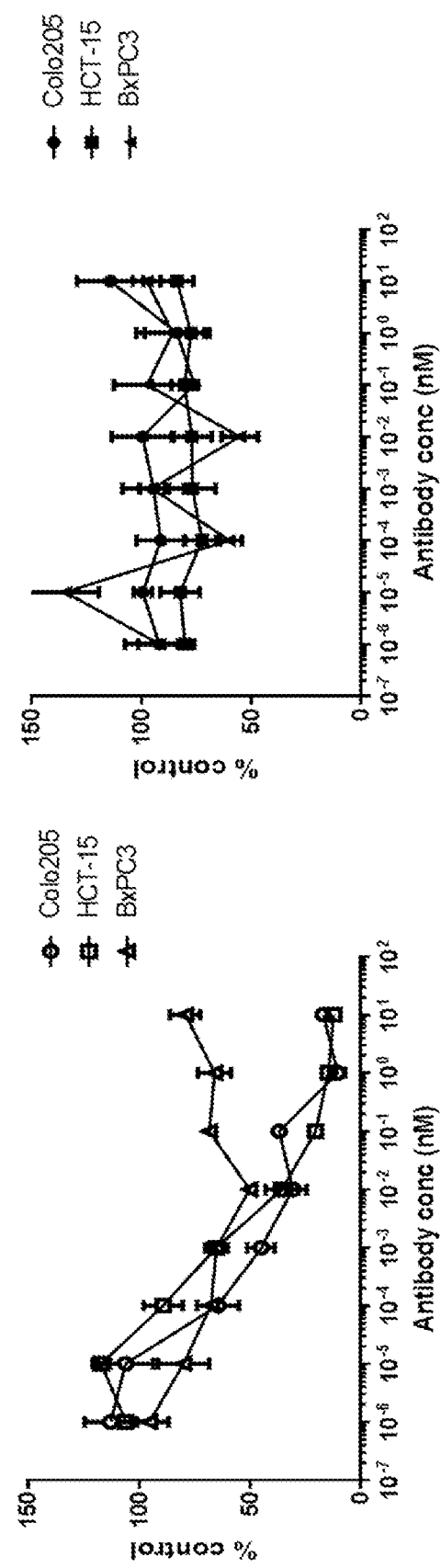
FIG. 11c: Cytotoxicity of Fab-ZAP-CH129 Against HCT15, Colo205, BxPC3 cancer Cell lines. The cytotoxicity of internalised CH129 pre-incubated with saporin-linked anti-human IgG Fab fragment was evaluated using $^3$H-thymidine incorporation. Results are presented normalised, as percentage of proliferation of cells treated with the primary mAb only. Error bars show the mean±SD from four independent experiments.
FIG. 11d: Fab-ZAP-IgG Isotype internalisation assay. Results are presented normalised, as percentage of proliferation of cells treated with the primary mAb only. Error bars show the mean±SD from three independent experiments.

Internalisation was confirmed by ADC assays using Fab-ZAP, an anti-mouse IgG or anti-human IgG linked to the ribosome inactivating protein saporin, which killed the cells that internalised the Fab-ZAP-FG129/CH129 immune complex, but left the cells that did not internalise unaffected. Internalisation of Fab-ZAP-FG129 or CH129 led to a dose-dependent decrease in cell viability (Ic50~$10^{-12}$M) on high binding cells Colo205 and HCT-15 but not BxPc3 or ASPC1 (FIGS. 11a and 11c). No killing of low expressing cell lines LS180 or antigen negative cell line LoVo was observed (FIG. 11a). Fab-ZAP alone or Fab-ZAP pre-incubated with an isotype-matched IgG1 antibody against an antigen not expressed by cells, did not kill the cells (FIGS. 11b and 11d).

Additionally, to investigate if CH129 would make a promising ADC candidate in a clinical setting, the mab was chemically conjugated to different payload/linker constructs that were pre-clinically and clinically validated. Thus, three CH129 constructs were produced by ADC Biotechnology: one with the auristatin MMAE linked via a cleavable dipeptide valine-citruline linker and a para-aminobenzylalcohol (PABA) self-immolative spacer (CH129-vcE), one with the DM4 maytansinoid linked via the intermediately cleavable hindered disulphide linker SPDB (CH129-DM4) and one with the DM1 maytansinoid linked through the non-cleavable SMCC linker (CH129-DM1). A matched set of control ADC constructs was also produced using the non-targeting mab Rituximab, to be used in relevant assay controls. Cytotoxicity was studied on two colorectal cell lines Colo205 and HCT-15 that express high cell surface densities of the targeted antigen sialyl-lewis-a.

Figures 11E, 11F:
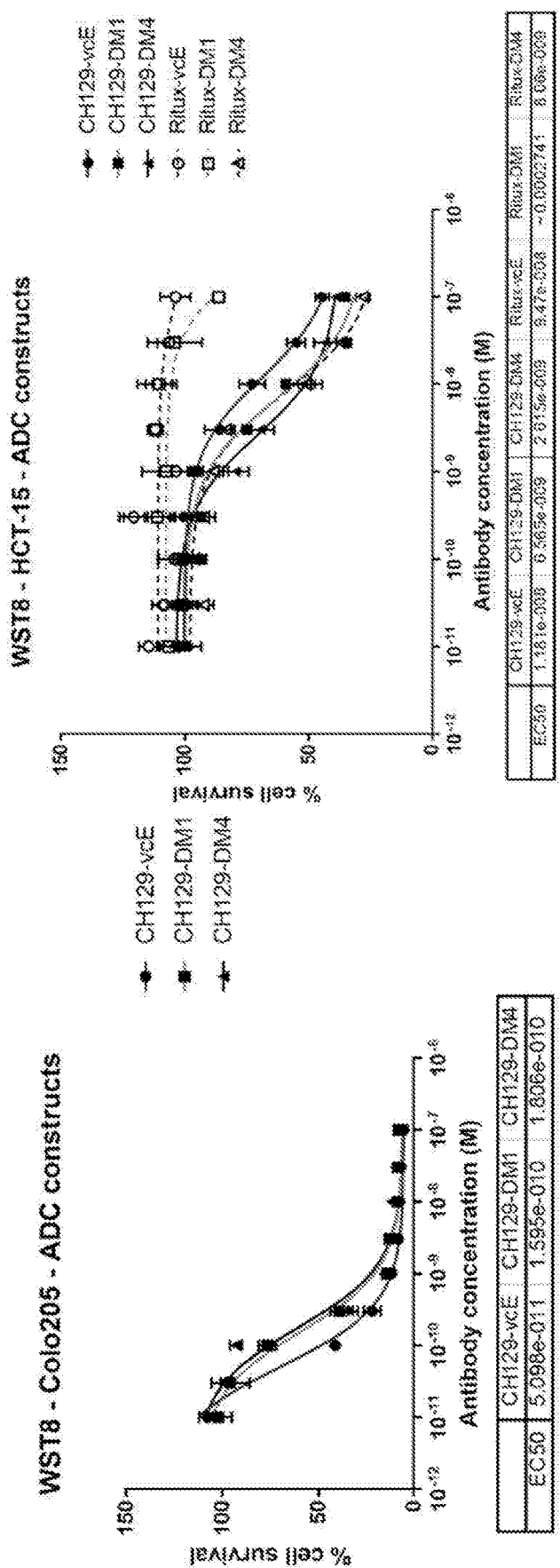
FIG. 11e: WST8 cytotoxicity assay showing in vitro efficacy of CH129-ADC constructs on Colo205. All three CH129-ADC constructs gave 100% cell killing with the vcE construct giving the highest efficacy (Ec50~$10^{-11}$M) followed by the DM1 and DM4 constructs showing similar efficacy (Ec50s~$10^{-10}$M).
FIG. 11f: WST8 cytotoxicity assay showing in vitro efficacy of CH129-ADC constructs on HCT-15. CH129 constructs show 50-60% cell killing. Rituximab-ADC constructs were used as controls for specific killing. Ritux-vcE and Ritux-DM1 do not show cell killing. Ritux-DM4 shows similar killing activity to the CH129 constructs, indicating non-specific cell killing.

CH129-ADC constructs give high in vitro target dependant efficacy. Results show a dose dependant decrease in cell death directly related with the decrease in antibody concentration on both cell lines. Cell killing was also target dependent, with higher killing being seen on the higher antigen expressing cell line Colo205, compared to HCT-15. On Colo205 (FIG. 11e) all three CH129-ADC constructs gave 100% cell killing with the vcE construct giving the highest efficacy (Ec50~$10^{-11}$M) followed by the DM1 and DM4 constructs showing similar efficacy (Ec50s~$10^{-10}$M).

On HCT-15 (FIG. 11f) only 50-60% of the cells were killed at the highest concentrations, with CH129-DM4 giving the best Ec50 of $2\times10^{-9}$M, while DM1 gave an Ec50 of $6\times10^{-9}$M and vcE giving an Ec50 of $10^{-8}$M. Matched Rituximab-ADC constructs which did not bind the cell line were used as controls to assess the specificity of the killing. The absence of activity of the vcE and DM1 Rituximab constructs, indicates that the activity seen with the targeted constructs is specific, and not due to systemic release of free drug. However, Rituximab-DM4 shows similar activity to the CH129 constructs, suggesting non-specific killing.

In order to determine if the ADCs with cleavable linkers would kill antigen negative cells from the surroundings of antigen positive cells, the ADC constructs were tested on a mixture of antigen positive and antigen negative cells, and as well on cell lines with heterogeneous tumour antigen expression.

ADCs with Cleavable Linkers Give Bystander Killing Compared with Uncleavable Linkers.

Figure 11I:
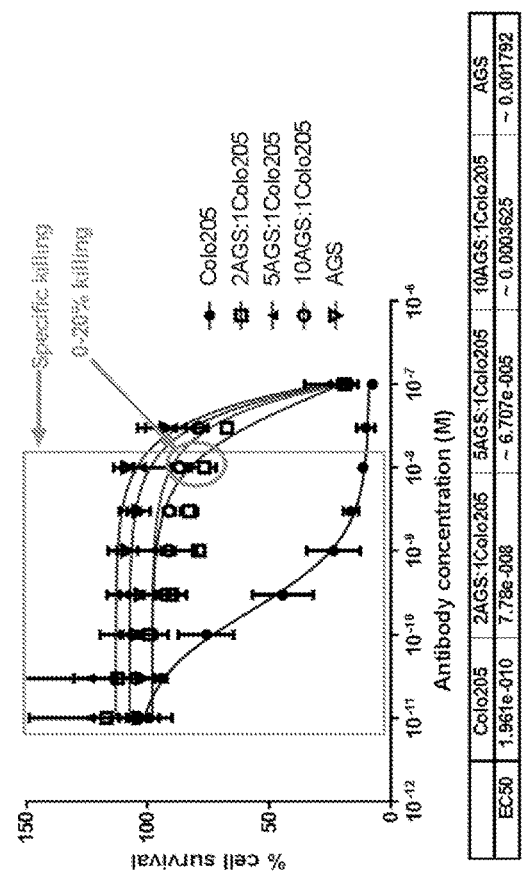
FIG. 11i: WST8 cytotoxicity assay showing bystander killing of the CH129-DM1 construct.
Figure 11G:
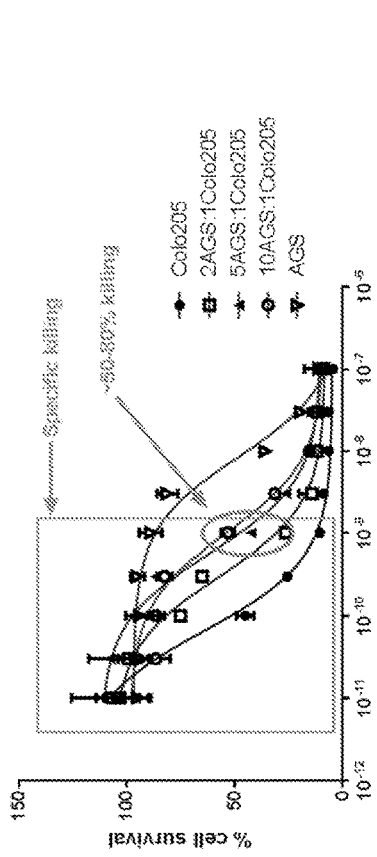
FIG. 11g: WST8 cytotoxicity assay showing bystander killing of the CH129-vcE construct.
Figure 11H:
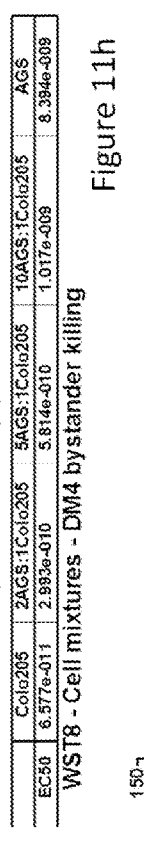
FIG. 11h: WST8 cytotoxicity assay showing bystander killing of the CH129-DM4 construct.

The bystander killing effect of the ADC constructs was evaluated on different cell ratio mixtures of high tumour antigen expressing cells Colo205 with cells that do not express the antigen—AGS. Cells were mixed at ratios of 2:1, 5:1 and 10:1 AGS to Colo205. Colo205 only, and AGS only were used as positive and negative controls respectively. Since AGS is an antigen negative cell line, the killing see on this cell line is non-specific, therefore concentrations at which killing is observed on AGS were not considered when assessing bystander killing. Specific killing is shown in FIGS. 11g, 11h and 11i highlighted by the rectangle. DM1 was the most stable in this aspect, as it showed killing at concentrations higher than 10 nM, while DM4 at 3 nM and vcE were less stable showing non-specific killing from 1 nM.

As DM1 is linked with a non-cleavable linker, it consisted the negative control for bystander killing. The difference between the killing given by DM1 and DM4/vcE at the circled concentrations could be due to bystander killing. Thus, DM4 gave a specific killing of ~90%, vcE of ~50-80% while DM1 of ~20% of the cells.

Example 8

Figure 12A:
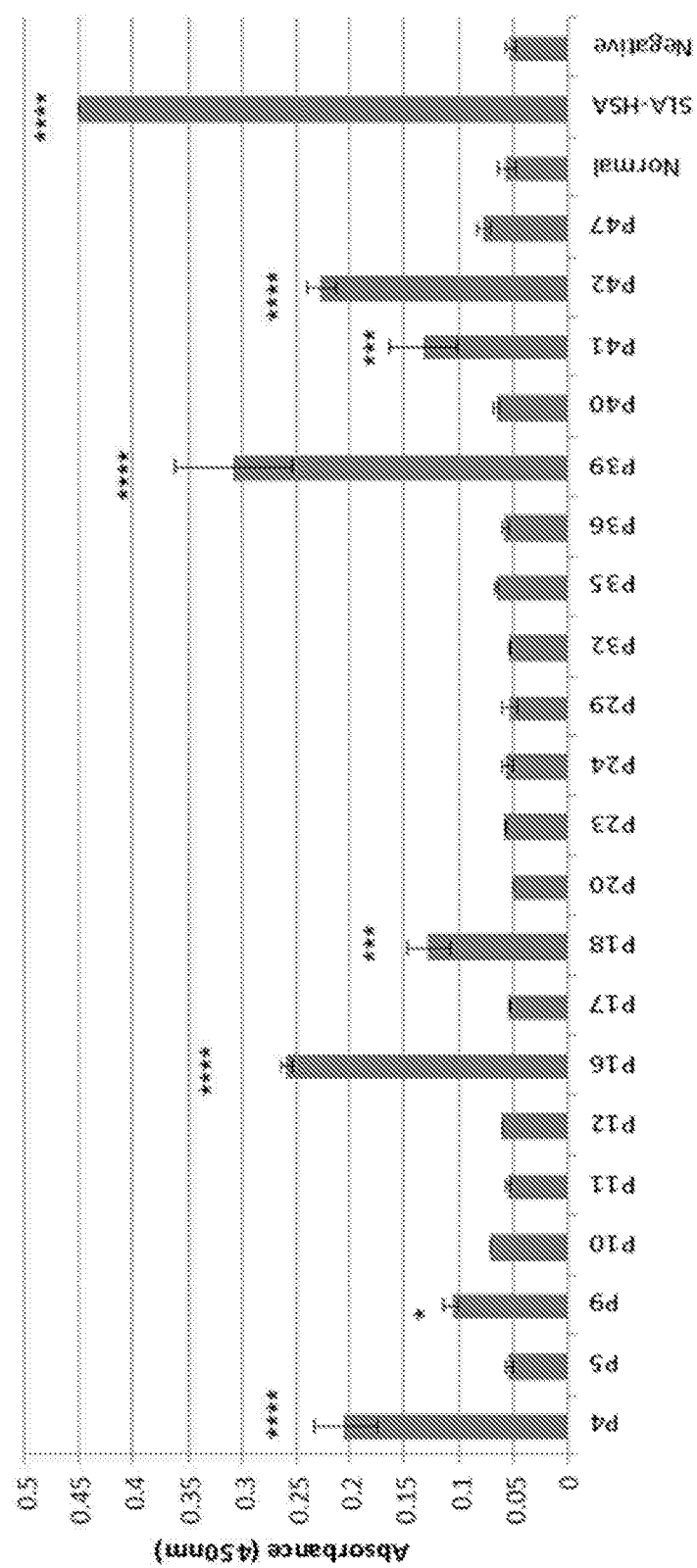
FIG. 12a: Sandwich ELISA using FG129 for the detection of secreted sialyl-Lewis$^a$ in sera from pancreatic cancer patients. Negative controls consisted of a normal serum sample from a healthy donor, and 2% BSA-PBS alone. Sialyl-Lewis$^a$-HSA was used as a positive control.

Expression of Sialyl-Lewis A on Secreted Antigens within Sera from Cancer Patients The presence of secreted FG129 antigen in pancreatic patients sera was investigated by sandwich ELISA, which showed that FG129 bound to 33% (7/21) of sera (FIG. 12a). When tumours from these patients were analysed by IHC for binding of sialyl-di-Lewis$^a$ on the tumour cells or within the stroma, all but one tumour was positive but only 6 tumours displayed stromal staining. The presence of secreted antigen was significantly associated with stromal tissue staining from tumours resected from these patients (p=0.023, correlation coefficient=0.621) suggesting that staining of resected tumours could predict patients in whom antigen may be present in the serum (Table 4).

TABLE 4

Tumour and stromal H score by IHC and pancreatic serum binding by sandwich ELISA of FG129

|     | Tumor H score | Stromal H score | Sandwich ELISA Panc serum binding to FG129 OD |
| --- | --- | --- | --- |
| P4  | 200 | 100 | 0.2 |
| P5  | 180 | 0   | 0.05 |
| P9  | 285 | 150 | 0.11 |
| P10 | 120 | 0   | 0.07 |
| P11 | 60  | 0   | 0.05 |
| P12 | 150 | 100 | 0.06 |
| P18 | 250 | 40  | 0.13 |
| P20 | 0   | 0   | 0.05 |
| P23 | 260 | 0   | 0.06 |
| P32 | 110 | 0   | 0.05 |
| P36 | 120 | 0   | 0.06 |
| P40 | 280 | 25  | 0.06 |
| P41 | 130 | 70  | 0.13 |

Figure 12B:
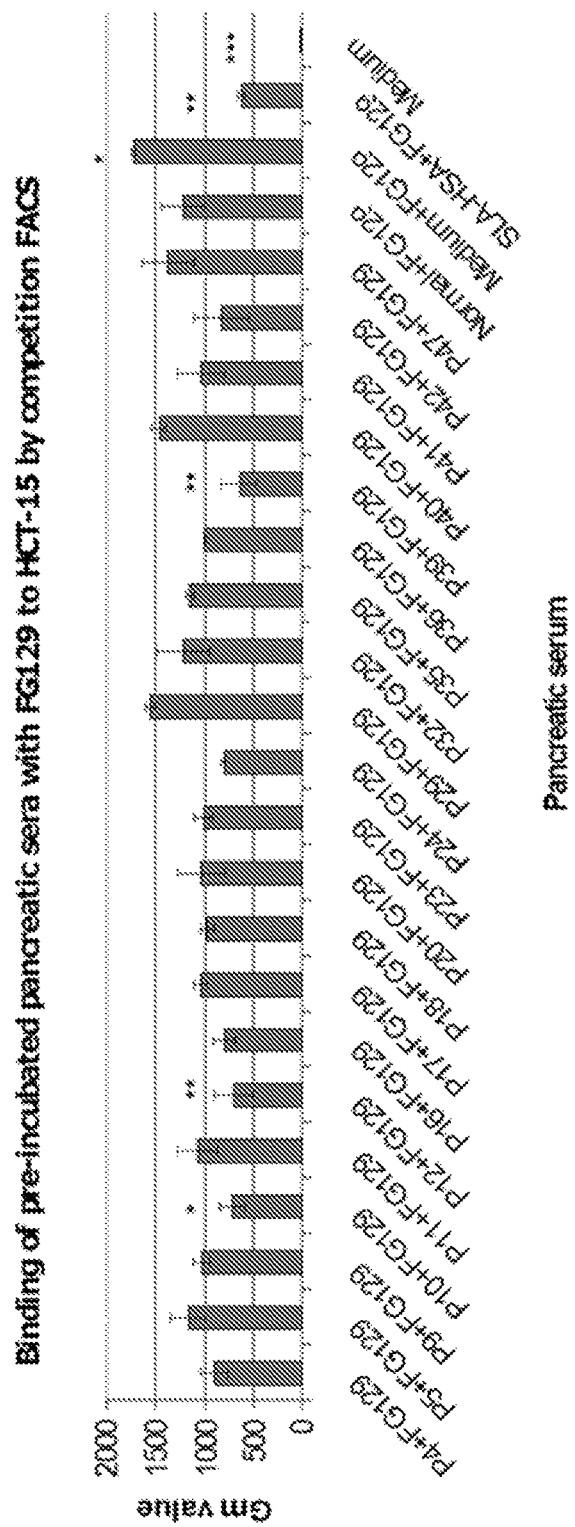
FIG. 12b: Competition FACS assay showing binding to HCT-15 cell line of pre-incubated FG129 with sera from patients from the pancreatic TMA cohort. Positive controls consisted of normal sera samples from five healthy donors (shown as average between the five), and 2% BSA-PBS pre-incubated with FG129. Negative controls consisted of sialyl-Lewis$^a$-HSA pre-incubated with FG129 and 2% BSA-PBS alone.

In order to mimic the in vivo setting, it was investigated if at 37° C. FG129 would bind preferentially to secreted antigen or to tumour cell surface. Binding of FG129 to secreted antigen or tumour cells was analysed in a competition FACS assay on HCT-15 cells at 37° C. All serum reduced binding to HCT-15 cells but there was no association with secreted sialyl-Lewis$^a$ antigen suggesting the viscosity of the serum reduced the kinetics of mAb binding. Serum from a normal donor which did not have secreted sialyl-Lewis$^a$ antigen also showed a reduction in binding to HCT-15 cells (Gm x to 1200). Antigen positive patient sera also reduced binding (Gm 600-1000) as did antigen negative patent sera (Gm 650-1500). Even though FG129 was pre-incubated with the pancreatic sera, the mAb showed a strong preference for binding to the cells and not to the secreted antigen from the sera (FIG. 12b). This suggests that secreted antigen should not prevent FG129 from localising within tumours.

Example 9

Cloning, Expression, Purification and Characterization of the FG129-scFv

With its limited normal tissue binding and the very high tumour tissue binding, the FG129 antibody makes an attractive candidate to be used in the context of a chimeric antigen receptor (CAR) as a scFv in order to induce anti-tumour T cell responses.

To determine if the scFv would maintain the binding characteristics of the FG129 full antibody, the heavy chain and light chain variable region were incorporated in silico into a single scFv sequence in the orientation: leader, heavy chain variable domain, spacer (3×GGGGS), light chain variable domain, spacer (6×Ala); purification tag (6×His) and synthesized (FIG. 13a). After cloning into a eukaryotic expression vector, Expi293 cells were transfected and allowed to produce protein transiently (6 days). His-tagged scFv was purified from Expi-293 supernatant using immobilised cobalt chromatography. The scFv was then characterised in terms of its binding properties to the sialyl-Lewis-a antigen or to cells expressing the antigen.

Figure 13C:
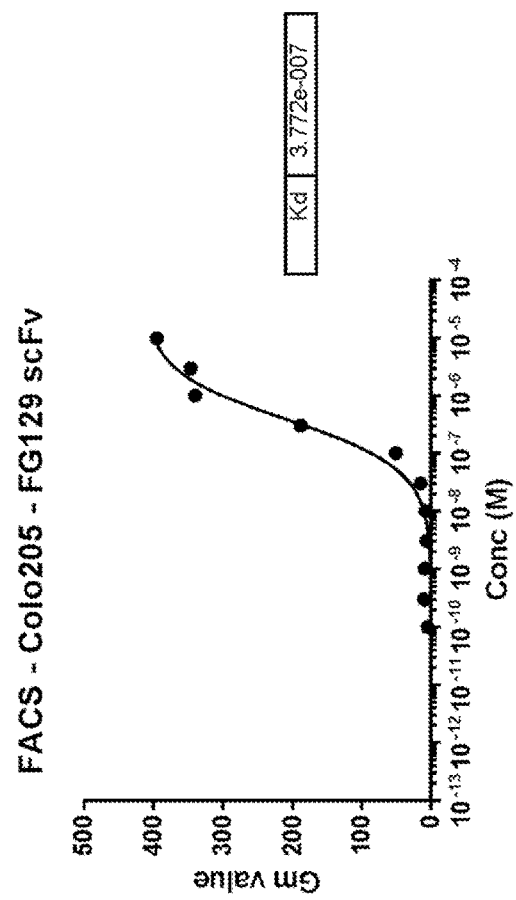
FIG. 13c: Indirect immunofluorescence staining and flow cytometric analysis of titrations of FG129-scFv binding to the cell surface of Colo205.
Figure 13B:
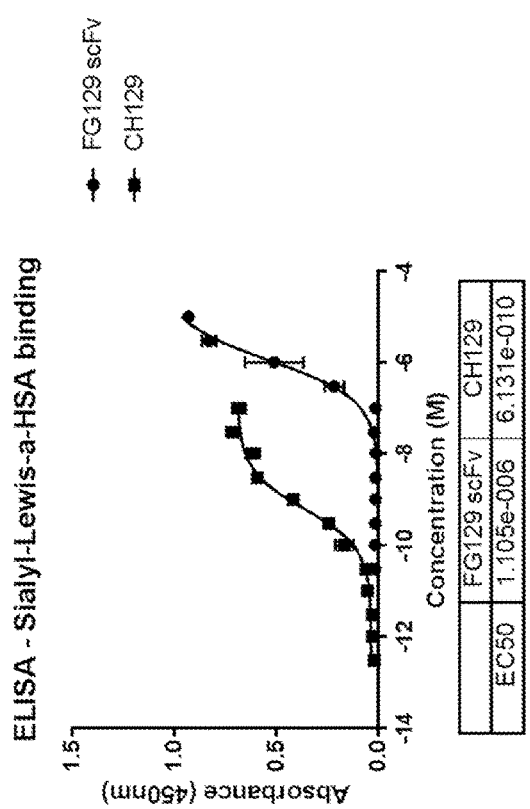
FIG. 13b: ELISA analysis of FG129-scFv and CH129 binding to sialyl-Lewis$^a$-HSA. Error bars represent the mean±SD of duplicate wells.

The antigen binding affinity of the FG129-scFv was measured by SPR and by ELISA on sialyl-Lewis-a. In antigen binding assay by ELISA, the FG129-scFv showed specific sialyl-Lewis-a binding that titrated down with decrease in scFv concentration (Ec50=$10^{-6}$M) (FIG. 13b). Antigen binding affinity was also measured by SPR which gave a Kd of $10^{-7}$M (Table 1). In cell binding assays, on Colo205, the FG129-scFv showed a high binding (Gm ~400) and gave a dose dependent response with a submicromolar Kd ($10^{-7}$M) (FIG. 13c). Therefore the FG129-scFv maintains a high specific binding comparable to the binding of the full antibody and also displays a high binding affinity (Kd~$10^{-7}$M) despite having only one binding instead of the two binding arms of the full FG129 mab.

The Sequence Listing is submitted as an ASCII text file in the form of the file named Sequence_Listing.txt, which was created on Feb. 23, 2018, and is 21,700 bytes, which is incorporated by reference herein.

Sequences (SEQ ID NO: 8)
Mouse FG129/29 IgG1 heavy chain.
```
atg ctg ttg ggg ctg aag tgg gtt ttc ttt gtt gtt ttt tat caa ggt gtg cat tgt gag gtg cag ctt gtt gag tct ggt gga ... gga ttg gtg cag cct aaa ggg tca ttg aaa ctc tca tgt gca gcc tct gga ttc acc ttc ... ... ... ... aat acc tac gcc atg aac tgg gtc cgc cag gct cca gga aag ggt ttg gaa tgg gtt gct cgc ata aga agt aaa agt aat aat tat gca aca tat tat gcc gat tca gtg aaa ... gac agg ttc acc ata tcc aga gat gat tca caa agc atg ctc tat ctg caa atg aac aac ttg aaa aag gag gac aca gcc atg tat tac tgt gta ggg tac ggt agt ggg gga aac tac tgg ggt caa gga ... ... ...

acc tca gtc acc gtc tcc tca gcc aaa acg aca ccc cca tct gtc tat cca ctg gcc cct gga tct gct gcc caa act aac tcc atg gtg acc ctg gga tgc ctg gtc aag ggc tat ttc cct gag cca gtg aca gtg acc tgg aac tct gga tcc ctg tcc agc ggt gtg cac acc ttc cca gct gtc ctg gag tct gac ctc tac act ctg agc agc tca gtg act gtc ccc tcc agc cct cgg ccc agc gag acc gtc acc tgc aac gtt gcc cac ccg gcc agc agc acc aag gtg gac aag aaa att gtg ccc agg gat tgt ggt tgt aag cct tgc ata tgt aca gtc cca gaa gta tca tct gtc ttc atc ttc ccc cca aag ccc aag gat gtg ctc acc att act ctg act cct aag gtc acg tgt gtt gtg gta gac atc agc aag gat gat ccc gag gtc cag ttc agc tgg ttt gta gat gat gtg gag gtg cac aca gct cag acg caa ccc cgg gag gag cag ttc aac agc act ttc cgc tca gtc agt gaa ctt ccc atc atg cac cag gac tgg ctc aat ggc aag gag ttc aaa tgc agg gtc aac agt gca gct ttc cct gcc ccc atc gag aaa acc atc tcc aaa acc aaa ggc aga ccg aag gct cca cag gtg tac acc att cca cct ccc aag gag cag atg gcc aag gat aaa gtc agt ctg acc tgc atg ata aca gac ttc ttc cct gaa gac att act gtg gag tgg cag tgg aat ggg cag cca gcg gag aac tac aag aac act cag ccc atg atg aac acg aat ggc tct tac ttc gtc tac agc aag ctc aat gtg cag aag agc aac tgg gag gca gga aat act ttc acc tgc tct gtg tta cat gag ggc ctg cac aac cac cat act gag aag agc ctc tcc cac tct cct ggt aaa
```

(SEQ ID NO: 9)
Mouse FG129/29 kappa chain.
atg gaa tca cag act cag gtc ctc atg tcc ctg ctg ttc tgg gta tct acc tgt ggg gac att gtg atg aca cag tct cca tcc tcc ctg act gtg aca gca gga gag aag gtc act atg agc tgc aag tcc agt cag agt ctg tta aac agt gga aat caa aag aac tac ttg acc tgg tac cag cag aaa cca ggg cag cct cct aaa gtg ttg atc tac tgg gca ... ... ...

... ... ... ... tcc act agg gaa tct ggg gtc cct ... gat cgc ttc aca ggc agt gga ... ... tct gga aca gat ttc act ctc acc atc agc agt gtg cag gct gaa gac ctg gca gtt tat tac tgt cag aat gat tat agt tct cca ttc acg ttc ggc tcg ggg aca aag ttg gaa ata aaa cgg gct gat gct gca cca act gta tcc atc ttc cca cca tcc agt gag cag tta aca tct gga ggt gcc tca gtc gtg tgc ttc ttg aac aac ttc tac ccc aaa gac atc aat gtc aag tgg aag att gat ggc agt gaa cga caa aat ggc gtc ctg aac agt tgg act gat cag gac agc aaa gac agc acc tac agc atg agc agc acc ctc acg ttg acc aag gac gag tat gaa cga cat aac agc tat acc tgt gag gcc act cac aag aca tca act tca ccc att gtc aag agc ttc aac agg aat gag tgt (SEQ ID NO: 10)
Mouse FG129/29 heavy chain chimerised to hIgG1 constant region
atg ctg ttg ggg ctg aag tgg gtt ttc ttt gtt gtt ttt tat caa ggt gtg cat tgt gag gtg cag ctt gtt gag tct ggt gga ... gga ttg gtg cag cct aaa ggg tca ttg aaa ctc tca tgt gca gcc tct gga ttc acc ttc ... ... ... ... aat acc tac gcc atg aac tgg gtc cgc cag gct cca gga aag ggt ttg gaa tgg gtt gct cgc ata aga agt aaa agt aat aat tat gca aca tat tat gcc gat tca gtg aaa ... gac agg ttc acc ata tcc aga gat gat tca caa agc atg ctc tat ctg caa atg aac aac ttg aaa aag gag gac aca gcc atg tat tac tgt gta ggg tac ggt agt ggg gga aac tac tgg ggt caa gga ... ... ...

acc tca gtc acc gtc tcc agc gct tcc acc aag ggc cca tcg gtc ttc ccc ctg gca ccc tcc tcc aag agc acc tct ggg ggc aca gcg gcc ctg ggc tgc ctg gtc aag gac tac ttc ccc gaa ccg gtg acg gtg tcg tgg aac tca ggc gcc ctg acc agc ggc gtg cac acc ttc ccg gct gtc cta cag tcc tca gga ctc tac tcc ctc agc agc gtg gtg acc gtg ccc tcc agc agc ttg ggc acc cag acc tac atc tgc aac gtg aat cac aag ccc agc aac acc aag gtg gac aag aaa gtt gag ccc aaa tct tgt gac aaa act cac aca tgc cca ccg tgc cca gca cct gaa ctc ctg ggg gga ccg tca gtc ttc ctc ttc ccc cca aaa ccc aag gac acc ctc atg atc tcc cgg acc cct gag gtc aca -continued

```
tgc gtg gtg gtg gac gtg agc cac gaa gac cct gag gtc aag ttc aac tgg tac gtg gac ggc gtg gag gtg cat aat gcc aag aca aag ccg cgg gag gag cag tac aac agc acg tac cgt gtg gtc agc gtc ctc acc gtc ctg cac cag gac tgg ctg aat ggc aag gag tac aag tgc aag gtc tcc aac aaa gcc ctc cca gcc ccc atc gag aaa acc atc tcc aaa gcc aaa ggg cag ccc cga gaa cca cag gtg tac acc ctg ccc cca tcc cgg gat gag ctg acc aag aac cag gtc agc ctg acc tgc ctg gtc aaa ggc ttc tat ccc agc gac atc gcc gtg gag tgg gag agc aat ggg cag ccg gag aac aac tac aag acc acg cct ccc gtg ctg gac tcc gac ggc tcc ttc ttc ctc tac agc aag ctc acc gtg gac aag agc agg tgg cag cag ggg aac gtc ttc tca tgc tcc gtg atg cat gag gct ctg cac aac cac tac acg cag aag agc ctc tcc ctg tct ccg ggt aaa
```

(SEQ ID NO: 11)
Mouse FG129/29 kappa chain chimerised to hIgk constant region

```
atg gaa tca cag act cag gtc ctc atg tcc ctg ctg ttc tgg gta tct acc tgt ggg gac att gtg atg aca cag tct cca tcc tcc ctg act gtg aca gca gga gag aag gtc act atg agc tgc aag tcc agt cag agt ctg tta aac agt gga aat caa aag aac tac ttg acc tgg tac cag cag aaa cca ggg cag cct cct aaa gtg ttg atc tac tgg gca ... ... ...

... ... ... ... tcc act agg gaa tct ggg gtc cct ... gat cgc ttc aca ggc agt gga ... ... tct gga aca gat ttc act ctc acc atc agc agt gtg cag gct gaa gac ctg gca gtt tat tac tgt cag aat gat tat agt tct cca ttc acg ttc ggc tcg ggg aca aag ttg gaa ata aaa cgt acg gta gcg gcc cca tct gtc ttc atc ttc ccg cca tct gat gag cag ttg aaa tct gga act gcc tct gtt gtg tgc ctg ctg aat aac ttc tat ccc aga gag gcc aaa gta cag tgg aag gtg gat aac gcc ctc caa tcg ggt aac tcc cag gag agt gtc aca gag cag gac agc aag gac agc acc tac agc ctc agc agc acc ctg acg ctg agc aaa gca gac tac gag aaa cac aaa gtc tac gcc tgc gaa gtc acc cat cag ggc ctg agc tcg ccc gtc aca aag agc ttc aac agg gga gag tgt
```

FIG. 1a: Complete amino acid sequence of mouse F129/29 IgG1 heavy chain. (SEQ ID NO: 12)

```
 -19 MLLGLKWVFFVVFYQGVHC

1 EVQLVESGGGLVQPKGSLKLSCAASGFTF

31 NTYAMNWVRQAPGKGLEWVARIRSKS

61 NNYATYYADSVKDRFTISRDDSQSMLYLQ

91 MNNLKKEDTAMYYCVGYGSGGNYWGQG

121 TSVTVSSAKTTPPSVYPLAPGSAAQTNSMV

151 TLGCLVKGYFPEPVTVTWNSGSLSSGVHTF

181 PAVLESDLYTLSSSVTVPSSPRPSETVTCN

211 VAHPASSTKVDKKIVPRDCGCKPCICTVPE

241 VSSVFIFPPKPKDVLTITLTPKVTCVVVDI

271 SKDDPEVQFSWFVDDVEVHTAQTQPREEQF

301 NSTFRSVSELPIMHQDWLNGKEFKCRVNSA

331 AFPAPIEKTISKTKGRPKAPQVYTIPPPKE
```

```
361 QMAKDKVSLTCMITDFFPEDITVEWQWNGQ
391 PAENYKNTQPIMNTNGSYFVYSKLNVQKSN
421 WEAGNTFTCSVLHEGLHNHHTEKSLSHSPG
451 K
```

FIG. 1b: Complete amino acid sequence of mouse F129/29 kappa chain. (SEQ ID NO: 13)

```
-19 MESQTQVLMSLLFWVSTCG
  1 DIVMTQSPSSLTVTAGEKVTMSCKSSQSLL
 31 NSGNQKNYLTWYQQKPGQPPKVLIYWA
 61 STRESGVPDRFTGSGSGTDFTLT
 91 ISSVQAEDLAVYYCQNDYSSPFTFGSGTKL
121 EIKRADAAPTVSIFPPSSEQLTSGGASVVC
151 FLNNFYPKDINVKWKIDGSERQNGVLNSWT
181 DQDSKDSTYSMSSTLTLTKDEYERHNSYTC
211 EATHKTSTSPIVKSFNRNEC
```

FIG. 2a: Complete amino acid sequence of mouse FG129/29 heavy chain variable region chimerised to human IgG1 heavy chain constant region. (SEQ ID NO: 14)

```
-19 MLLGLKWVFFVVFYQGVHC
  1 EVQLVESGGGLVQPKGSLKLSCAASGFTF
 31 NTYAMNWVRQAPGKGLEWVARIRSKS
 61 NNYATYYADSVKDRFTISRDDSQSMLYLQ
 91 MNNLKKEDTAMYYCVGYGSGGNYWGQG
121 TSVTVSSASTKGPSVFPLAPSSKSTSGGTA
151 ALGCLVKDYFPEPVTVSWNSGALTSGVHTF
181 PAVLQSSGLYSLSSVVTVPSSSLGTQTYIC
211 NVNHKPSNTKVDKKVEPKSCDKTHTCPPCP
241 APELLGGPSVFLFPPKPKDTLMISRTPEVT
271 CVVVDVSHEDPEVKFNWYVDGVEVHNAKTK
301 PREEQYNSTYRVVSVLTVLHQDWLNGKEYK
331 CKVSNKALPAPIEKTISKAKGQPREPQVYT
361 LPPSRDELTKNQVSLTCLVKGFYPSDIAVE
391 WESNGQPENNYKTTPPVLDSDGSFFLYSKL
421 TVDKSRWQQGNVFSCSVMHEALHNHYTQKS
451 LSLSPGK
```

FIG. 2b: Complete amino acid sequence of mouse FG129/29 kappa chain variable region chimerised to human kappa chain constant region. (SEQ ID NO: 15)

```
-19 MESQTQVLMSLLFWVSTCG
  1 DIVMTQSPSSLTVTAGEKVTMSCKSSQSLL
 31 NSGNQKNYLTWYQQKPGQPPKVLIYWA
 61 STRESGVPDRFTGSGSGTDFTLT
 91 ISSVQAEDLAVYYCQNDYSSPFTFGSGTKL
121 EIKRTVAAPSVFIFPPSDEQLKSGTASVVC
151 LLNNFYPREAKVQWKVDNALQSGNSQESVT
181 EQDSKDSTYSLSSTLTLSKADYEKHKVYAC
211 EVTHQGLSSPVTKSFNRGEC
```

REFERENCES CITED IN THE DESCRIPTION

1. Hakomori S. Glycosylation defining cancer malignancy: new wine in an old bottle. Proc Natl Acad Sci USA. 2002; 99:10231-3.
2. Fuster M M, Esko J D. The sweet and sour of cancer: glycans as novel therapeutic targets. Nat Rev Cancer. 2005; 5:526-42.
3. Varki A, Kannagi R, Toole B P. Glycosylation Changes in Cancer. In: Varki A, Cummings R D, Esko J D, et al., editors. Essentials of Glycobiology. 2010/03/20 ed: Cold Spring Harbor (N.Y.); 2009.
4. Pour P M, Tempero M M, Takasaki H, Uchida E, Takiyama Y, Burnett D A, et al. Expression of blood group-related antigens ABH, Lewis A, Lewis B, Lewis X, Lewis Y, and CA 19-9 in pancreatic cancer cells in comparison with the patient's blood group type. Cancer Res. 1988; 48:5422-6.
5. Rabu C, McIntosh R, Jurasova Z, Durrant L. Glycans as targets for therapeutic antitumor antibodies. Future Oncol. 2012; 8:943-60.
6. Tang H, Singh S, Partyka K, Kletter D, Hsueh P, Yadav J, et al. Glycan motif profiling reveals plasma sialyl-lewis x elevations in pancreatic cancers that are negative for sialyl-lewis a. Molecular & cellular proteomics: MCP. 2015; 14:1323-33.
7. Inagaki H, Sakamoto J, Nakazato H, Bishop A E, Yura J. Expression of Lewis(a), Lewis(b), and sialated Lewis(a) antigens in early and advanced human gastric cancers. J Surg Oncol. 1990; 44:208-13.
8. Sakamoto J, Furukawa K, Cordon-Cardo C, Yin B W, Rettig W J, Oettgen H F, et al. Expression of Lewis$^a$, Lewisb, X, and Y blood group antigens in human colonic tumors and normal tissue and in human tumor-derived cell lines. Cancer Res. 1986; 46:1553-61.
9. Hakomori S, Andrews H D. Sphingoglycolipids with Leb activity, and the co-presence of Lea-, Leb-glycolipids in human tumor tissue. Biochim Biophys Acta. 1970; 202: 225-8.
10. Koprowski H, Steplewski Z, Mitchell K, Herlyn M, Herlyn D, Fuhrer P. Colorectal carcinoma antigens detected by hybridoma antibodies. Somatic cell genetics. 1979; 5:957-71.
11. Stanley P, Cummings R D. Structures Common to Different Glycans. In: Varki A, Cummings R D, Esko J D, et al., editors. Essentials of Glycobiology. 2010/03/20 ed: Cold Spring Harbor (N.Y.); 2009.
12. Kannagi R. Carbohydrate antigen sialyl Lewis a—its pathophysiological significance and induction mechanism in cancer progression. Chang Gung medical journal. 2007; 30:189-209.
13. Kishimoto T, Ishikura H, Kimura C, Takahashi T, Kato H, Yoshiki T. Phenotypes correlating to metastatic properties of pancreas adenocarcinoma in vivo: the importance of surface sialyl Lewis(a) antigen. International journal of cancer Journal international du cancer. 1996; 69:290-4.
14. Sato M, Narita T, Kimura N, Zenita K, Hashimoto T, Manabe T, et al. The association of sialyl Lewis(a) antigen with the metastatic potential of human colon cancer cells. Anticancer research. 1997; 17:3505-11.
15. Matsui T, Kojima H, Suzuki H, Hamajima H, Nakazato H, Ito K, et al. Sialyl Lewisa expression as a predictor of the prognosis of colon carcinoma patients in a prospective randomized clinical trial. Japanese journal of clinical oncology. 2004; 34:588-93.
16. Nakayama T, Watanabe M, Katsumata T, Teramoto T, Kitajima M. Expression of sialyl Lewis(a) as a new prognostic factor for patients with advanced colorectal carcinoma. Cancer. 1995; 75:2051-6.
17. O'Brien D P, Sandanayake N S, Jenkinson C, Gentry-Maharaj A, Apostolidou S, Fourkala E O, et al. Serum CA19-9 is significantly upregulated up to 2 years before diagnosis with pancreatic cancer: implications for early disease detection. Clinical cancer research: an official journal of the American Association for Cancer Research. 2015; 21:622-31.
18. Sawada R, Sun S M, Wu X, Hong F, Ragupathi G, Livingston P O, et al. Human monoclonal antibodies to sialyl-Lewis (CA19.9) with potent CDC, ADCC, and antitumor activity. Clinical cancer research: an official journal of the American Association for Cancer Research. 2011; 17:1024-32.
19. Huehls A M, Coupet T A, Sentman C L. Bispecific T-cell engagers for cancer immunotherapy. Immunology and cell biology. 2015; 93:290-6.
20. Kontermann R E. Dual targeting strategies with bispecific antibodies. mAbs. 2012; 4:182-97.
21. Ward E S, Gussow D, Griffiths A D, Jones P T, Winter G. Binding activities of a repertoire of single immunoglobulin variable domains secreted from *Escherichia coli*. Nature. 1989; 341:544-6.
22. Bird R E, Hardman K D, Jacobson J W, Johnson S, Kaufman B M, Lee S M, et al. Single-chain antigen-binding proteins. Science. 1988; 242:423-6.
23. Huston J S, Levinson D, Mudgett-Hunter M, Tai M S, Novotny J, Margolies M N, et al. Protein engineering of antibody binding sites: recovery of specific activity in an anti-digoxin single-chain Fv analogue produced in *Escherichia coli*. Proc Natl Acad Sci USA. 1988; 85:5879-83.
24. Holliger P, Prospero T, Winter G. "Diabodies": small bivalent and bispecific antibody fragments. Proc Natl Acad Sci USA. 1993; 90:6444-8.
25. Holliger P, Winter G. Engineering bispecific antibodies. Current opinion in biotechnology. 1993; 4:446-9.
26. Traunecker A, Lanzavecchia A, Karjalainen K. Bispecific single chain molecules (Janusins) target cytotoxic lymphocytes on HIV infected cells. The EMBO journal. 1991; 10:3655-9.
27. Karlin S, Altschul S F. Methods for assessing the statistical significance of molecular sequence features by using general scoring schemes. Proc Natl Acad Sci USA. 1990; 87:2264-8.
28. Karlin S, Altschul S F. Applications and statistics for multiple high-scoring segments in molecular sequences. Proc Natl Acad Sci USA. 1993; 90:5873-7.
29. Altschul S F, Gish W, Miller W, Myers E W, Lipman D J. Basic local alignment search tool. Journal of molecular biology. 1990; 215:403-10.
30. Altschul S F, Madden T L, Schaffer A A, Zhang J, Zhang Z, Miller W, et al. Gapped BLAST and PSI-BLAST: a new generation of protein database search programs. Nucleic acids research. 1997; 25:3389-402.
31. Myers E W, Miller W. Approximate matching of regular expressions. Bulletin of mathematical biology. 1989; 51:5-37.
32. Torelli A, Robotti C A. ADVANCE and ADAM: two algorithms for the analysis of global similarity between homologous informational sequences. Computer applications in the biosciences: CABIOS. 1994; 10:3-5.
33. Pearson W R, Lipman D J. Improved tools for biological sequence comparison. Proc Natl Acad Sci USA. 1988; 85:2444-8.
34. Marks J D, Griffiths A D, Malmqvist M, Clackson T P, Bye J M, Winter G. By-passing immunization: building high affinity human antibodies by chain shuffling. Bio/technology. 1992; 10:779-83.
35. Stemmer W P. Rapid evolution of a protein in vitro by DNA shuffling. Nature. 1994; 370:389-91.
36. Gram H, Marconi L A, Barbas C F, 3rd, Collet T A, Lerner R A, Kang A S. In vitro selection and affinity maturation of antibodies from a naive combinatorial immunoglobulin library. Proc Natl Acad Sci USA. 1992; 89:3576-80.
37. Barbas C F, 3rd, Hu D, Dunlop N, Sawyer L, Cababa D, Hendry R M, et al. In vitro evolution of a neutralizing human antibody to human immunodeficiency virus type 1 to enhance affinity and broaden strain cross-reactivity. Proc Natl Acad Sci USA. 1994; 91:3809-13.
38. Schier R, McCall A, Adams G P, Marshall K W, Merritt H, Yim M, et al. Isolation of picomolar affinity anti-c-erbB-2 single-chain Fv by molecular evolution of the complementarity determining regions in the center of the antibody binding site. Journal of molecular biology. 1996; 263:551-67.
39. Sidman K R, Steber W D, Schwope A D, Schnaper G R. Controlled release of macromolecules and pharmaceuticals from synthetic polypeptides based on glutamic acid. Biopolymers. 1983; 22:547-56.
40. Langer R, Brem H, Tapper D. Biocompatibility of polymeric delivery systems for macromolecules. Journal of biomedical materials research. 1981; 15:267-77.
41. R. P. R. Remington's Pharmaceutical Sciences. 16th ed: Mack Pub. Co; 1980.
42. Stewart J M. Solid Phase Peptide Synthesis. 2nd ed: Pierce Chemical Co; 1984.
43. Miklos Bodanszky A B, Barry M. Trost The Practice of Peptide Synthesis 1984.
44. Pluckthun A. Antibody engineering: advances from the use of *Escherichia coli* expression systems. Bio/technology. 1991; 9:545-51.
45. Reff M E. High-level production of recombinant immunoglobulins in mammalian cells. Current opinion in biotechnology. 1993; 4:573-6.
46. Trill J J, Shatzman A R, Ganguly S. Production of monoclonal antibodies in COS and CHO cells. Current opinion in biotechnology. 1995; 6:553-60.
47. Sambrook J. Molecular Cloning: A Laboratory Manual. 2nd ed; 1989.
48. Ausubel F M. Short Protocols in Molecular Biology; 1992.
49. Lefranc M P, Giudicelli V, Ginestoux C, Jabado-Michaloud J, Folch G, Bellahcene F, et al. IMGT, the international ImMunoGeneTics information system. Nucleic acids research. 2009; 37:D1006-12.

50. Jones S T, Bendig M M. Rapid PCR-cloning of full-length mouse immunoglobulin variable regions. Bio/technology. 1991; 9:579.
51. Simpson J A, Al-Attar A, Watson N F, Scholefield J H, Ilyas M, Durrant L G. Intratumoral T cell infiltration, MHC class I and STAT1 as biomarkers of good prognosis in colorectal cancer. Gut. 2010; 59:926-33.
52. Duncan T J, Rolland P, Deen S, Scott I V, Liu D T, Spendlove I, et al. Loss of IFN gamma receptor is an independent prognostic factor in ovarian cancer. Clinical cancer research: an official journal of the American Association for Cancer Research. 2007; 13:4139-45.
53. Abdel-Fatah T, Arora A, Gorguc I, Abbotts R, Beebeejaun S, Storr S, et al. Are DNA repair factors promising biomarkers for personalized therapy in gastric cancer?Antioxidants & redox signaling. 2013; 18:2392-8.
54. Storr S J, Zaitoun A M, Arora A, Durrant L G, Lobo D N, Madhusudan S, et al. Calpain system protein expression in carcinomas of the pancreas, bile duct and ampulla. BMC cancer. 2012; 12:511.
55. Kohls M D, Lappi D A. Mab-ZAP: a tool for evaluating antibody efficacy for use in an immunotoxin. BioTechniques. 2000; 28:162-5.

The invention claimed is:

1. An isolated antibody or antibody fragment specific for sialyl-di-Lewis$^a$, sialyl-Lewis$^{a-x}$, and mono-sialyl-Lewis$^a$ bound to a glycoprotein and which does not bind to mono-sialyl-Lewis$^a$ bound to a glycolipid, wherein the antibody or antibody fragment comprises the following six CDRs:
   a) QSLLNSGNQKNY (Light chain CDR1) (SEQ ID NO: 5), WAS (Light chain CDR2), and QNDYSSPFT (Light chain CDR3) (SEQ ID NO: 6); and
   b) GFTFNTYA (Heavy chain CDR1) (SEQ ID NO: 1), IRSKSNNYAT (Heavy chain CDR2) (SEQ ID NO: 2), and VGYGSGGNY (Heavy chain CDR3) (SEQ ID NO: 3).

2. The antibody or antibody fragment according to claim claim 1, wherein the mono-sialyl-Lewis$^a$ is linked to the glycoprotein by a glycan chain comprising at least 4 glycan monomer units.

3. The antibody or antibody fragment according to claim 1, wherein the antibody has:
   (i) a heavy chain amino acid sequence of:
   MLLGLKWVFFVVFYQGVHCEVQLVESGGGLVQPKGSLKLSCAASGFTFNTY AMNWVRQAPGKGLEWVARIRSKSNNYATYYADSVKDRFTISRDDSQSMLYLQMNN LKKEDTAMYYCVGYGSGGNYWGQGTSVTVSSAKTTPPSVYPLAPGSAAQTNSMVTL GCLVKGYFPEPVTVTWNSGSLSSGVHTFPAVLESDLYTLSSSVTVPSSPRPSETVTCNV AHPASSTKVDKKIVPRDCGCKPCICTVPEVSSVFIFPPKPKDVLTITLTPKVTCVVVDIS KDDPEVQFSWFVDDVEVHTAQTQPREEQFNSTFRSVSELPIMHQDWLNGKEFKCRVN SAAFPAPIEKTISKTKGRPKAPQVYTIPPPKEQMAKDKVSLTCMITDFFPEDITVEWQW NGQPAENYKNTQPIMNTNGSYFVYSKLNVQKSNWEAGNTFTCSVLHEGLHNHHTEK SLSHSPGK (SEQ ID NO: 12); and
   a light chain amino acid sequence of:
   MESQTQVLMSLLFWVSTCGDIVMTQSPSSLTVTAGEKVTMSCKSSQSLL NSGNQKNYLTWYQQKPGQPPKVLIYWASTRESGVPDRFTGSGSGTDFTLT ISSVQAEDLAVYYCQNDYSSPFTFGSGTKLEIKRADAAPTVSIFPPSSEQLTSGG ASVVCFLNNFYPKDINVKWKIDGSERQNGVLNSWTDQDSKDSTYSMSSTLTLTKDEY ERHNSYTCEATHKTSTSPIVKSFNRNEC (SEQ ID NO: 13); or
   (ii) a heavy chain amino acid sequence of:
   MLLGLKWVFFVVFYQGVHCEVQLVESGGGLVQPKGSLKLSCAASGFTF NTYAMNWVRQAPGKGLEWVARIRSKSNNYATYYADSVKDRFTISRDDSQSM LYLQMNNLKKEDTAMYYCVGYGSGGNYWGQGTSVTVSSASTKGPSVFPLAPSSKST SGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFLFPPKPKDTL MISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKNQVS LTCLVKGFYPSDIAVEWESNGQPENNYKTTPPVLDSDGSFFLYSKLTVDKSRWQQGN VFSCSVMHEALHNHYTQKSLSLSPGK (SEQ ID NO: 14); and
   a light chain amino acid sequence of:
   MESQTQVLMSLLFWVSTCGDIVMTQSPSSLTVTAGEKVTMSCKSSQSLL NSGNQKNYLTWYQQKPGQPPKVLIYWASTRESGVPDRFTGSGSGTDFTLT ISSVQAEDLAVYYCQNDYSSPFTFGSGTKLEIKRTVAAPSVFIFPPSDEQLKSGT ASVVCLLNNFYPREAKVQWKVDNALQSGNSQESVTEQDSKDSTYSLSSTLTLSKADY EKHKVYACEVTHQGLSSPVTKSFNRGEC (SEQ ID NO: 15).

4. The antibody or antibody fragment according to claim 1, wherein the antibody or antibody fragment is bispecific.

5. The antibody or antibody fragment according to claim 4, wherein the bispecific antibody or antibody fragment is additionally specific for CD3.

6. The antibody or antibody fragment according to claim 1, wherein the antibody or antibody fragment comprises:
   a light chain variable sequence comprising QSLLNSGNQKNY (Light chain CDR1) (SEQ ID NO: 5), WAS (Light chain CDR2), and QNDYSSPFT (Light chain CDR3) (SEQ ID NO: 6); and
   a heavy chain variable sequence comprising GFTFNTYA (Heavy chain CDR1) (SEQ ID NO: 1), IRSKSNNYAT (Heavy chain CDR2) (SEQ ID NO: 2), and VGYGSGGNY (Heavy chain CDR3) (SEQ ID NO: 3).

7. The antibody or antibody fragment according to claim 6, wherein the CDRs are carried by a human antibody framework.

8. The antibody or antibody fragment according to claim 6, wherein the antibody or antibody fragment comprises a VH domain comprising residues 1 to 117 (SEQ ID NO: 4) of the amino acid sequence of FIG. 1a or 2a, and/or a VL domain comprising residues 1 to 114 (SEQ ID NO: 7) of the amino acid sequence of FIG. 1b or 2b.

9. The antibody or antibody fragment according to claim 1, wherein the antibody or antibody fragment comprises a human antibody constant region.

10. The antibody or antibody fragment according to claim 1, wherein the antibody fragment is a Fab, (Fab')2, scFv, Fv, Fd or a diabody or wherein the antibody or antibody fragment is provided in the form of a chimeric antigen receptor (CAR).

11. The antibody or antibody fragment according to claim 10, wherein the antibody or antibody fragment is an scFv:
- (a) comprising in the following order: 1) leader sequence, 2) heavy chain variable region, 3) 3×GGGGS (SEQ ID NO: 18) spacer, 4) light chain variable region, and 5) poly-Ala and a 6×His tag for purification;
- (b) comprising in the following order: 1) leader sequence, 2) light chain variable region, 3) 3×GGGGS (SEQ ID NO: 18) spacer, and 4) heavy chain variable region, optionally further comprising either 5' or 3' purification tags, in the listed order; and/or
- (c) in the form of a chimeric antigen receptor (CAR) either in the heavy chain-light chain orientation or the light chain-heavy chain orientation.

12. The antibody or antibody fragment according to claim 1, wherein the antibody or antibody fragment is:
- (a) a monoclonal antibody;
- (b) a humanised, chimeric or veneered antibody; and/or
- (c) a drug conjugate, such as an antibody-drug conjugate (ADC).

13. A pharmaceutical composition comprising the antibody or antibody fragment according to claim 1, and a pharmaceutically acceptable carrier.

14. The pharmaceutical composition according to claim 13, further comprising at least one other active ingredient.

15. A nucleic acid comprising a sequence encoding the antibody or antibody fragment according to claim 1.

16. The nucleic acid according to claim 15, wherein the nucleic acid is a construct in the form of a plasmid, vector, transcription or expression cassette.

17. A recombinant host cell which comprises the nucleic acid according to claim 15.

\* \* \* \* \*

SEQUENCE LISTING

<160> NUMBER OF SEQ ID NOS: 18

<210> SEQ ID NO 1
<211> LENGTH: 8
<212> TYPE: PRT
<213> ORGANISM: Mus musculus

<400> SEQUENCE: 1

Gly Phe Thr Phe Asn Thr Tyr Ala
1               5

<210> SEQ ID NO 2
<211> LENGTH: 10
<212> TYPE: PRT
<213> ORGANISM: Mus musculus

<400> SEQUENCE: 2

Ile Arg Ser Lys Ser Asn Asn Tyr Ala Thr
1               5                   10

<210> SEQ ID NO 3
<211> LENGTH: 9
<212> TYPE: PRT
<213> ORGANISM: Mus musculus

<400> SEQUENCE: 3

Val Gly Tyr Gly Ser Gly Gly Asn Tyr
1               5

<210> SEQ ID NO 4
<211> LENGTH: 117
<212> TYPE: PRT
<213> ORGANISM: Mus musculus

<400> SEQUENCE: 4

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Lys Glu Asp Thr Ala Met Tyr
                85                  90                  95

Tyr Cys Val Gly Tyr Gly Ser Gly Gly Asn Tyr Trp Gly Gln Gly Thr
            100                 105                 110

Ser Val Thr Val Ser
            115

<210> SEQ ID NO 5
<211> LENGTH: 12
<212> TYPE: PRT
<213> ORGANISM: Mus musculus

<400> SEQUENCE: 5

Gln Ser Leu Leu Asn Ser Gly Asn Gln Lys Asn Tyr
1               5                   10

<210> SEQ ID NO 6
<211> LENGTH: 9
<212> TYPE: PRT
<213> ORGANISM: Mus musculus

<400> SEQUENCE: 6

Gln Asn Asp Tyr Ser Ser Pro Phe Thr
1               5

<210> SEQ ID NO 7
<211> LENGTH: 114
<212> TYPE: PRT
<213> ORGANISM: Mus musculus

<400> SEQUENCE: 7

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Val Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Ser Pro Phe Thr Phe Gly Ser Gly Thr Lys Leu Glu Ile
            100                 105                 110

Lys Arg

<210> SEQ ID NO 8
<211> LENGTH: 1383
<212> TYPE: DNA
<213> ORGANISM: Mus musculus

<400> SEQUENCE: 8
atgctgttgg ggctgaagtg ggttttcttt gttgtttttt atcaaggtgt gcattgtgag      60
gtgcagcttg ttgagtctgg tggaggattg gtgcagccta aagggtcatt gaaactctca     120
tgtgcagcct ctggattcac cttcaatacc tacgccatga actgggtccg ccaggctcca     180
ggaaagggtt tggaatgggt tgctcgcata agaagtaaaa gtaataatta tgcaacatat     240
tatgccgatt cagtgaaaga caggttcacc atatccagag atgattcaca aagcatgctc     300
tatctgcaaa tgaacaactt gaaaaaggag gacacagcca tgtattactg tgtagggtac     360
ggtagtgggg gaaactactg gggtcaagga acctcagtca ccgtctcctc agccaaaacg     420

| | |
|---|---|
| acacccccat ctgtctatcc actggcccct ggatctgctg cccaaactaa ctccatggtg | 480 |
| accctgggat gcctggtcaa gggctatttc cctgagccag tgacagtgac ctggaactct | 540 |
| ggatccctgt ccagcggtgt gcacaccttc ccagctgtcc tggagtctga cctctacact | 600 |
| ctgagcagct cagtgactgt cccctccagc cctcggccca gcgagaccgt cacctgcaac | 660 |
| gttgcccacc cggccagcag caccaaggtg gacaagaaaa ttgtgcccag ggattgtggt | 720 |
| tgtaagcctt gcatatgtac agtcccagaa gtatcatctg tcttcatctt cccccccaaag | 780 |
| cccaaggatg tgctcaccat tactctgact cctaaggtca cgtgtgttgt ggtagacatc | 840 |
| agcaaggatg atcccgaggt ccagttcagc tggtttgtag atgatgtgga ggtgcacaca | 900 |
| gctcagacgc aaccccggga ggagcagttc aacagcactt tccgctcagt cagtgaactt | 960 |
| cccatcatgc accaggactg gctcaatggc aaggagttca aatgcagggt caacagtgca | 1020 |
| gctttccctg cccccatcga gaaaaccatc tccaaaacca aggcagacc gaaggctcca | 1080 |
| caggtgtaca ccattccacc tcccaaggag cagatggcca aggataaagt cagtctgacc | 1140 |
| tgcatgataa cagacttctt ccctgaagac attactgtgg agtggcagtg gaatgggcag | 1200 |
| ccagcggaga actacaagaa cactcagccc atcatgaaca cgaatggctc ttacttcgtc | 1260 |
| tacagcaagc tcaatgtgca gaagagcaac tgggaggcag gaaatacttt cacctgctct | 1320 |
| gtgttacatg agggcctgca caaccaccat actgagaaga gcctctccca ctctcctggt | 1380 |
| aaa | 1383 |

<210> SEQ ID NO 9
<211> LENGTH: 717
<212> TYPE: DNA
<213> ORGANISM: Mus musculus

<400> SEQUENCE: 9

| | |
|---|---|
| atggaatcac agactcaggt cctcatgtcc ctgctgttct gggtatctac ctgtggggac | 60 |
| attgtgatga cacagtctcc atcctccctg actgtgacag caggagagaa ggtcactatg | 120 |
| agctgcaagt ccagtcagag tctgttaaac agtggaaatc aaaagaacta cttgacctgg | 180 |
| taccagcaga aaccagggca gcctcctaaa gtgttgatct actgggcatc cactaggaa | 240 |
| tctggggtcc ctgatcgctt cacaggcagt ggatctggaa cagatttcac tctcaccatc | 300 |
| agcagtgtgc aggctgaaga cctggcagtt tattactgtc agaatgatta tagttctcca | 360 |
| ttcacgttcg gctcggggac aaagttggaa ataaaacggg ctgatgctgc accaactgta | 420 |
| tccatcttcc caccatccag tgagcagtta acatctggag gtgcctcagt cgtgtgcttc | 480 |
| ttgaacaact ctaccccaa agacatcaat gtcaagtgga agattgatgg cagtgaacga | 540 |
| caaaatggcg tcctgaacag ttggactgat caggacagca agacagcac ctacagcatg | 600 |
| agcagcaccc tcacgttgac caaggacgag tatgaacgac ataacagcta cctgtgagag | 660 |
| gccactcaca agacatcaac ttcacccatt gtcaagagct caacaggaa tgagtgt | 717 |

<210> SEQ ID NO 10
<211> LENGTH: 1401
<212> TYPE: DNA
<213> ORGANISM: Mus musculus

<400> SEQUENCE: 10

| | |
|---|---|
| atgctgttgg ggctgaagtg ggttttcttt gttgtttttt atcaaggtgt gcattgtgag | 60 |
| gtgcagcttg ttgagtctgg tggaggattg gtgcagccta agggtcatt gaaactctca | 120 |
| tgtgcagcct ctggattcac cttcaatacc tacgccatga ctgggtccg ccaggctcca | 180 |

| | |
|---|---|
| ggaaagggtt tggaatgggt tgctcgcata agaagtaaaa gtaataatta tgcaacatat | 240 |
| tatgccgatt cagtgaaaga caggttcacc atatccagag atgattcaca aagcatgctc | 300 |
| tatctgcaaa tgaacaactt gaaaaaggag gacacagcca tgtattactg tgtagggtac | 360 |
| ggtagtgggg gaaactactg gggtcaagga acctcagtca ccgtctccag cgcttccacc | 420 |
| aagggcccat cggtcttccc cctggcaccc tcctccaaga gcacctctgg gggcacagcg | 480 |
| gccctgggct gcctggtcaa ggactacttc cccgaaccgg tgacggtgtc gtggaactca | 540 |
| ggcgccctga ccagcggcgt gcacaccttc ccggctgtcc tacagtcctc aggactctac | 600 |
| tccctcagca gcgtggtgac cgtgccctcc agcagcttgg gcacccagac ctacatctgc | 660 |
| aacgtgaatc acaagcccag caacaccaag gtggacaaga agttgagcc caaatcttgt | 720 |
| gacaaaactc acacatgccc accgtgccca gcacctgaac tcctgggggg accgtcagtc | 780 |
| ttcctcttcc ccccaaaacc caaggacacc ctcatgatct cccggacccc tgaggtcaca | 840 |
| tgcgtggtgg tggacgtgag ccacgaagac cctgaggtca agttcaactg gtacgtggac | 900 |
| ggcgtggagg tgcataatgc caagacaaag ccgcgggagg agcagtacaa cagcacgtac | 960 |
| cgtgtggtca gcgtcctcac cgtcctgcac caggactggc tgaatggcaa ggagtacaag | 1020 |
| tgcaaggtct ccaacaaagc cctcccagcc cccatcgaga aaaccatctc caaagccaaa | 1080 |
| gggcagcccc gagaaccaca ggtgtacacc ctgcccccat cccgggatga gctgaccaag | 1140 |
| aaccaggtca gcctgacctg cctggtcaaa ggcttctatc ccagcgacat cgccgtggag | 1200 |
| tgggagagca atgggcagcc ggagaacaac tacaagacca cgcctcccgt gctggactcc | 1260 |
| gacggctcct tcttcctcta cagcaagctc accgtggaca agagcaggtg gcagcagggg | 1320 |
| aacgtcttct catgctccgt gatgcatgag gctctgcaca accactacac gcagaagagc | 1380 |
| ctctccctgt ctccgggtaa a | 1401 |

<210> SEQ ID NO 11
<211> LENGTH: 717
<212> TYPE: DNA
<213> ORGANISM: Mus musculus

<400> SEQUENCE: 11

| | |
|---|---|
| atggaatcac agactcaggt cctcatgtcc ctgctgttct gggtatctac ctgtggggac | 60 |
| attgtgatga cacagtctcc atcctccctg actgtgacag caggagagaa ggtcactatg | 120 |
| agctgcaagt ccagtcagag tctgttaaac agtggaaatc aaaagaacta cttgacctgg | 180 |
| taccagcaga aaccagggca gcctcctaaa gtgttgatct actgggcatc cactaggaa | 240 |
| tctggggtcc ctgatcgctt cacaggcagt ggatctggaa cagatttcac tctcaccatc | 300 |
| agcagtgtgc aggctgaaga cctggcagtt tattactgtc agaatgatta tagttctcca | 360 |
| ttcacgttcg gctcggggac aaagttggaa ataaaacgta cggtagcggc cccatctgtc | 420 |
| ttcatcttcc cgccatctga tgagcagttg aaatctggaa ctgcctctgt tgtgtgcctg | 480 |
| ctgaataact tctatcccag agaggccaaa gtacagtgga aggtggataa cgccctccaa | 540 |
| tcgggtaact cccaggagag tgtcacagag caggacagca aggacagcac ctacagcctc | 600 |
| agcagcaccc tgacgctgag caaagcagac tacgagaaac acaaagtcta cgcctgcgaa | 660 |
| gtcacccatc agggcctgag ctcgcccgtc acaaagagct tcaacagggg agagtgt | 717 |

<210> SEQ ID NO 12
<211> LENGTH: 461
<212> TYPE: PRT

<213> ORGANISM: Mus musculus

<400> SEQUENCE: 12

Met Leu Leu Gly Leu Lys Trp Val Phe Phe Val Phe Tyr Gln Gly
1               5                   10                  15

Val His Cys Glu Val Gln Leu Val Glu Ser Gly Gly Gly Leu Val Gln
            20                  25                  30

Pro Lys Gly Ser Leu Lys Leu Ser Cys Ala Ala Ser Gly Phe Thr Phe
            35                  40                  45

Asn Thr Tyr Ala Met Asn Trp Val Arg Gln Ala Pro Gly Lys Gly Leu
    50                  55                  60

Glu Trp Val Ala Arg Ile Arg Ser Lys Ser Asn Asn Tyr Ala Thr Tyr
65                  70                  75                  80

Tyr Ala Asp Ser Val Lys Asp Arg Phe Thr Ile Ser Arg Asp Asp Ser
                85                  90                  95

Gln Ser Met Leu Tyr Leu Gln Met Asn Asn Leu Lys Lys Glu Asp Thr
            100                 105                 110

Ala Met Tyr Tyr Cys Val Gly Tyr Gly Ser Gly Gly Asn Tyr Trp Gly
            115                 120                 125

Gln Gly Thr Ser Val Thr Val Ser Ser Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Glu Ser Asp Leu Tyr Thr Leu Ser Ser Ser Val Thr Val Pro
        195                 200                 205

Ser Ser Pro Arg Pro Ser Glu Thr Val Thr Cys Asn Val Ala His Pro
210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
        275                 280                 285

Phe Ser Trp Phe Val Asp Asp Val Glu Val His Thr Ala Gln Thr Gln
290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365

Lys Glu Gln Met Ala Lys Asp Lys Val Ser Leu Thr Cys Met Ile Thr
370                 375                 380

Asp Phe Phe Pro Glu Asp Ile Thr Val Glu Trp Gln Trp Asn Gly Gln
385                 390                 395                 400

```
Pro Ala Glu Asn Tyr Lys Asn Thr Gln Pro Ile Met Asn Thr Asn Gly
                405                 410                 415

Ser Tyr Phe Val Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
        435                 440                 445

His His Thr Glu Lys Ser Leu Ser His Ser Pro Gly Lys
    450                 455                 460

<210> SEQ ID NO 13
<211> LENGTH: 239
<212> TYPE: PRT
<213> ORGANISM: Mus musculus

<400> SEQUENCE: 13

Met Glu Ser Gln Thr Gln Val Leu Met Ser Leu Leu Phe Trp Val Ser
1               5                   10                  15

Thr Cys Gly Asp Ile Val Met Thr Gln Ser Pro Ser Ser Leu Thr Val
            20                  25                  30

Thr Ala Gly Glu Lys Val Thr Met Ser Cys Lys Ser Ser Gln Ser Leu
        35                  40                  45

Leu Asn Ser Gly Asn Gln Lys Asn Tyr Leu Thr Trp Tyr Gln Gln Lys
    50                  55                  60

Pro Gly Gln Pro Pro Lys Val Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Ser Pro Phe Thr Phe Gly Ser Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

<210> SEQ ID NO 14
<211> LENGTH: 467
<212> TYPE: PRT
<213> ORGANISM: Mus musculus

<400> SEQUENCE: 14

Met Leu Leu Gly Leu Lys Trp Val Phe Phe Val Val Phe Tyr Gln Gly
1               5                   10                  15

Val His Cys Glu Val Gln Leu Val Glu Ser Gly Gly Gly Leu Val Gln
            20                  25                  30
```

-continued

```
Pro Lys Gly Ser Leu Lys Leu Ser Cys Ala Ala Ser Gly Phe Thr Phe
            35                  40                  45

Asn Thr Tyr Ala Met Asn Trp Val Arg Gln Ala Pro Gly Lys Gly Leu
 50                  55                  60

Glu Trp Val Ala Arg Ile Arg Ser Lys Ser Asn Asn Tyr Ala Thr Tyr
 65                  70                  75                  80

Tyr Ala Asp Ser Val Lys Asp Arg Phe Thr Ile Ser Arg Asp Asp Ser
                 85                  90                  95

Gln Ser Met Leu Tyr Leu Gln Met Asn Asn Leu Lys Lys Glu Asp Thr
            100                 105                 110

Ala Met Tyr Tyr Cys Val Gly Tyr Gly Ser Gly Gly Asn Tyr Trp Gly
            115                 120                 125

Gln Gly Thr Ser Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
            210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
```

```
            450                 455                 460

Pro Gly Lys
465

<210> SEQ ID NO 15
<211> LENGTH: 239
<212> TYPE: PRT
<213> ORGANISM: Mus musculus

<400> SEQUENCE: 15

Met Glu Ser Gln Thr Gln Val Leu Met Ser Leu Leu Phe Trp Val Ser
1               5                   10                  15

Thr Cys Gly Asp Ile Val Met Thr Gln Ser Pro Ser Ser Leu Thr Val
            20                  25                  30

Thr Ala Gly Glu Lys Val Thr Met Ser Cys Lys Ser Ser Gln Ser Leu
        35                  40                  45

Leu Asn Ser Gly Asn Gln Lys Asn Tyr Leu Thr Trp Tyr Gln Gln Lys
    50                  55                  60

Pro Gly Gln Pro Pro Lys Val Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Ser Pro Phe Thr Phe Gly Ser Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 16
<211> LENGTH: 19
<212> TYPE: DNA
<213> ORGANISM: Mus musculus

<400> SEQUENCE: 16
ttagcacccc tggccaagg                                                    19

<210> SEQ ID NO 17
<211> LENGTH: 21
<212> TYPE: DNA
<213> ORGANISM: Mus musculus

<400> SEQUENCE: 17
cttactccct tggaggccat g                                                 21
```

```
<210> SEQ ID NO 18
<211> LENGTH: 5
<212> TYPE: PRT
<213> ORGANISM: Artificial Sequence
<220> FEATURE:
<223> OTHER INFORMATION: Spacer sequence

<400> SEQUENCE: 18

Gly Gly Gly Gly Ser
1               5
```